US012731663B2

(12) United States Patent
Lee

(10) Patent No.: US 12,731,663 B2
(45) Date of Patent: Sep. 8, 2026

(54) SYSTEM FOR PROVIDING MEDICAL RECORD SERVICE FOR ANIMAL WITH HEART DISEASE

(71) Applicant: Seung Gon Lee, Seoul (KR)

(72) Inventor: Seung Gon Lee, Seoul (KR)

(*) Notice: Subject to any disclaimer, the term of this patent is extended or adjusted under 35 U.S.C. 154(b) by 0 days.

(21) Appl. No.: 18/496,943

(22) Filed: Oct. 30, 2023

(65) Prior Publication Data

US 2024/0233893 A1 Jul. 11, 2024

(30) Foreign Application Priority Data

Oct. 28, 2022 (KR) ........................ 10-2022-0141183

(51) Int. Cl.
*G16H 10/60* (2018.01)
*G16H 10/20* (2018.01)
*G16H 50/20* (2018.01)

(52) U.S. Cl.
CPC ............. *G16H 10/60* (2018.01); *G16H 10/20* (2018.01); *G16H 50/20* (2018.01)

(58) Field of Classification Search
CPC ........ G16H 10/60; G16H 10/20; G16H 50/20; G16H 40/67; Y02A 40/70
See application file for complete search history.

(56) References Cited

U.S. PATENT DOCUMENTS 11,348,689 B1 * 5/2022 Gonzales, Jr. ......... G16H 10/60
2006/0110049 A1 * 5/2006 Liang ........................ G06T 7/20 382/224
2014/0123912 A1 * 5/2014 Menkes ............... A01K 27/001 119/859
2020/0381119 A1 * 12/2020 Gibbs .................... G16H 40/67
2023/0062081 A1 * 3/2023 Kuperman ............. G16H 30/40

FOREIGN PATENT DOCUMENTS

JP 2016224777 A * 12/2016
KR 20160012112 2/2016
KR 20180110762 10/2018
(Continued)

OTHER PUBLICATIONS

KR102411321B English Translation (Year: 2022).*
(Continued)

*Primary Examiner* — Mamon Obeid
(74) *Attorney, Agent, or Firm* — JCIPRNET

(57) ABSTRACT

Provided is a system for providing a medical record service for diagnosing a companion animal with a heart disease or internal disease. The system includes a user terminal configured to register a companion animal and then answer at least one question and a checklist for noting an abnormality, measuring a sleeping respiratory rate (SRR), recording a status, and recording syncope and seizures, a veterinary hospital terminal configured to output records written through the user terminal, and a medical record service providing server including a basic information part configured to allow the user terminal to record basic information of the companion animal when the user terminal registers the companion animal, an abnormality note part configured to display and store the abnormality note and a time in a messenger form when the abnormality note is written through the user terminal.

9 Claims, 55 Drawing Sheets

(56) References Cited

FOREIGN PATENT DOCUMENTS

| | | | | |
|---|---|---|---|---|
| KR | 20180135338 | | | 12/2018 |
| KR | 20210026960 | | | 3/2021 |
| KR | 20210026960 | A | * | 3/2021 |
| KR | 20220026644 | A | * | 3/2022 |
| KR | 20220029536 | | | 3/2022 |
| KR | 102411321 | B1 | * | 6/2022 |
| KR | 20220091652 | A | * | 7/2022 |

OTHER PUBLICATIONS

KR20210026960A English Translation (Year: 2021).*
KR20220026644A English Translation (Year: 2022).*
KR20220091652A English Translation (Year: 2022).*
JP2016224777A English Translation (Year: 2016).*
Ravikumar et al (Insight into the Internet of Medical Things (IoMT): Health Services and Applications) (Year: 2022).*

* cited by examiner

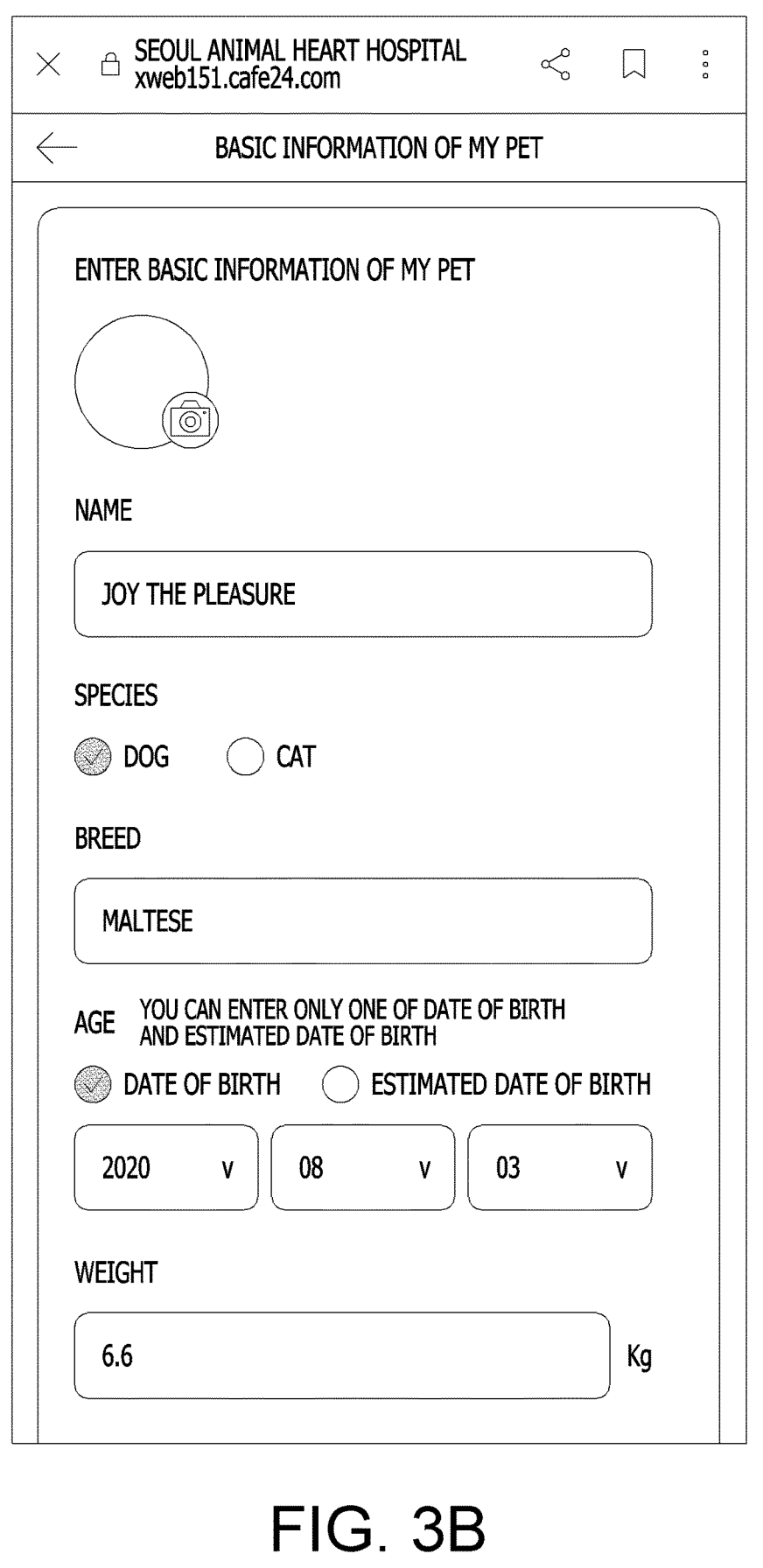

SEOUL ANIMAL HEART HOSPITAL
xweb151.cafe24.com

BASIC INFORMATION OF MY PET

ENTER BASIC INFORMATION OF MY PET

NAME

JOY THE PLEASURE

SPECIES

DOG CAT

BREED

MALTESE

AGE YOU CAN ENTER ONLY ONE OF DATE OF BIRTH AND ESTIMATED DATE OF BIRTH

DATE OF BIRTH ESTIMATED DATE OF BIRTH 2020 v 08 v 03 v

WEIGHT 6.6 Kg

FIG. 3B

Figure 3C:
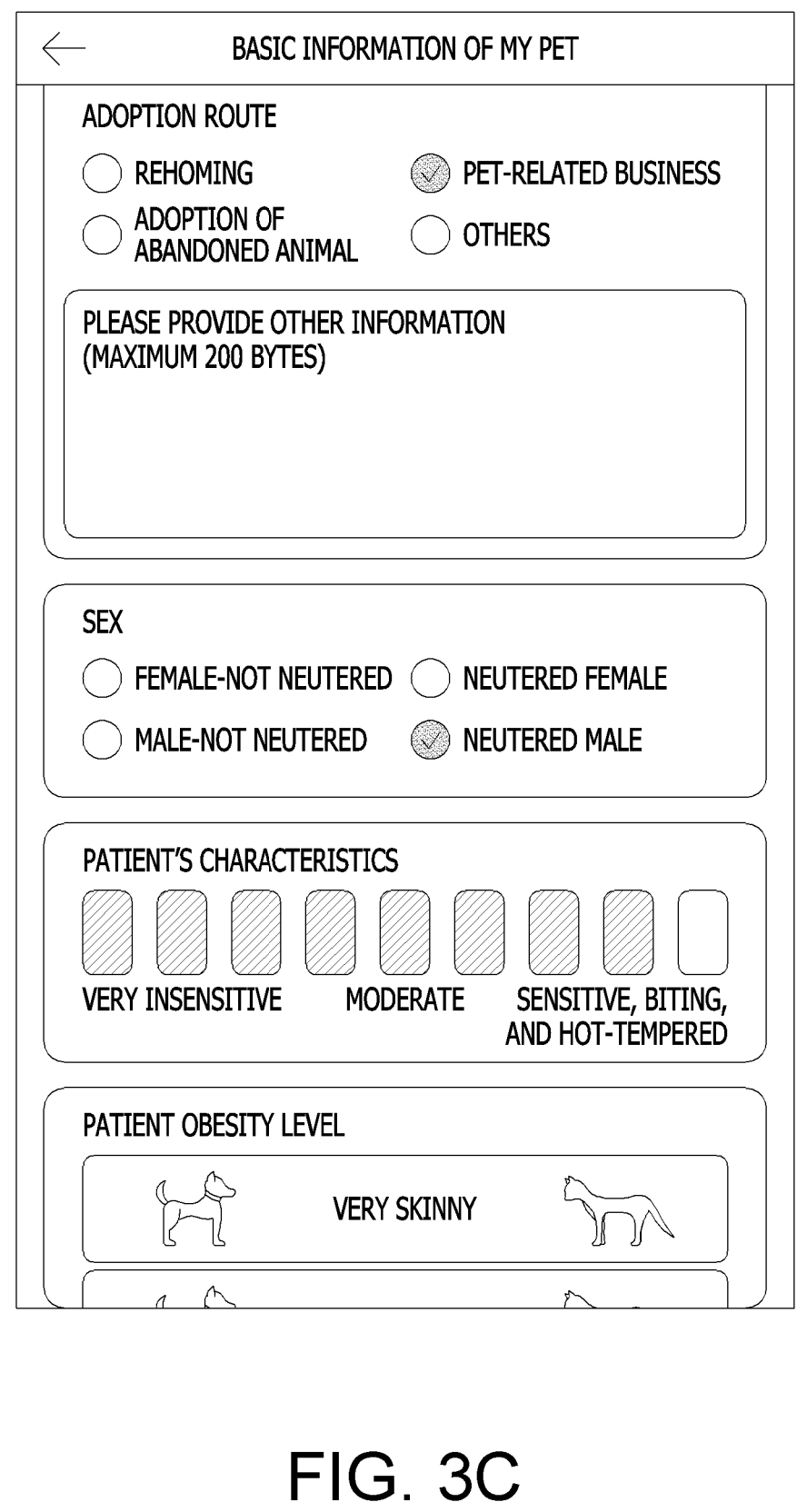

BASIC INFORMATION OF MY PET

ADOPTION ROUTE

REHOMING
PET-RELATED BUSINESS
ADOPTION OF ABANDONED ANIMAL
OTHERS

PLEASE PROVIDE OTHER INFORMATION (MAXIMUM 200 BYTES)

SEX

FEMALE-NOT NEUTERED
NEUTERED FEMALE
MALE-NOT NEUTERED
NEUTERED MALE

PATIENT'S CHARACTERISTICS

VERY INSENSITIVE
MODERATE
SENSITIVE, BITING, AND HOT-TEMPERED

PATIENT OBESITY LEVEL

VERY SKINNY

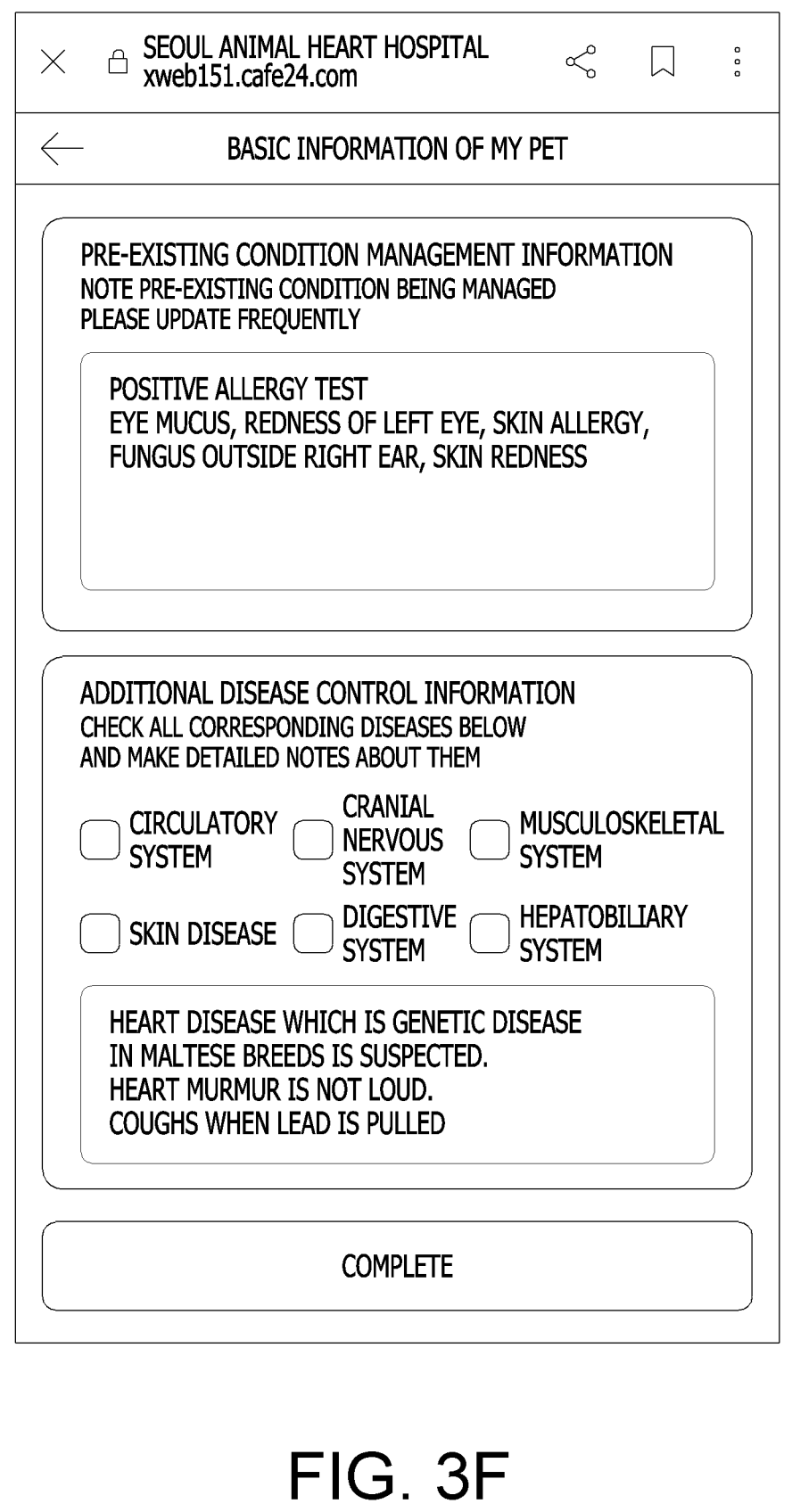

SEOUL ANIMAL HEART HOSPITAL
xweb151.cafe24.com

BASIC INFORMATION OF MY PET

PRE-EXISTING CONDITION MANAGEMENT INFORMATION
NOTE PRE-EXISTING CONDITION BEING MANAGED
PLEASE UPDATE FREQUENTLY

POSITIVE ALLERGY TEST
EYE MUCUS, REDNESS OF LEFT EYE, SKIN ALLERGY,
FUNGUS OUTSIDE RIGHT EAR, SKIN REDNESS

ADDITIONAL DISEASE CONTROL INFORMATION
CHECK ALL CORRESPONDING DISEASES BELOW
AND MAKE DETAILED NOTES ABOUT THEM

- [ ] CIRCULATORY SYSTEM
- [ ] CRANIAL NERVOUS SYSTEM
- [ ] MUSCULOSKELETAL SYSTEM
- [ ] SKIN DISEASE
- [ ] DIGESTIVE SYSTEM
- [ ] HEPATOBILIARY SYSTEM

HEART DISEASE WHICH IS GENETIC DISEASE
IN MALTESE BREEDS IS SUSPECTED.
HEART MURMUR IS NOT LOUD.
COUGHS WHEN LEAD IS PULLED

COMPLETE

FIG. 3F

FIG. 3H
SEOUL ANIMAL HEART HOSPITAL
xweb151.cafe24.com
IMMEDIATE NOTE
SATURDAY OCTOBER 8, 2022
COUGHS WHEN TOUCHED BELOW THROAT.
AIRWAY NARROWING OR
HEART PROBLEM IS SUSPECTED
2022-10-08 12:25:58
ENTER MESSAGE
SEND

Figure 3J:
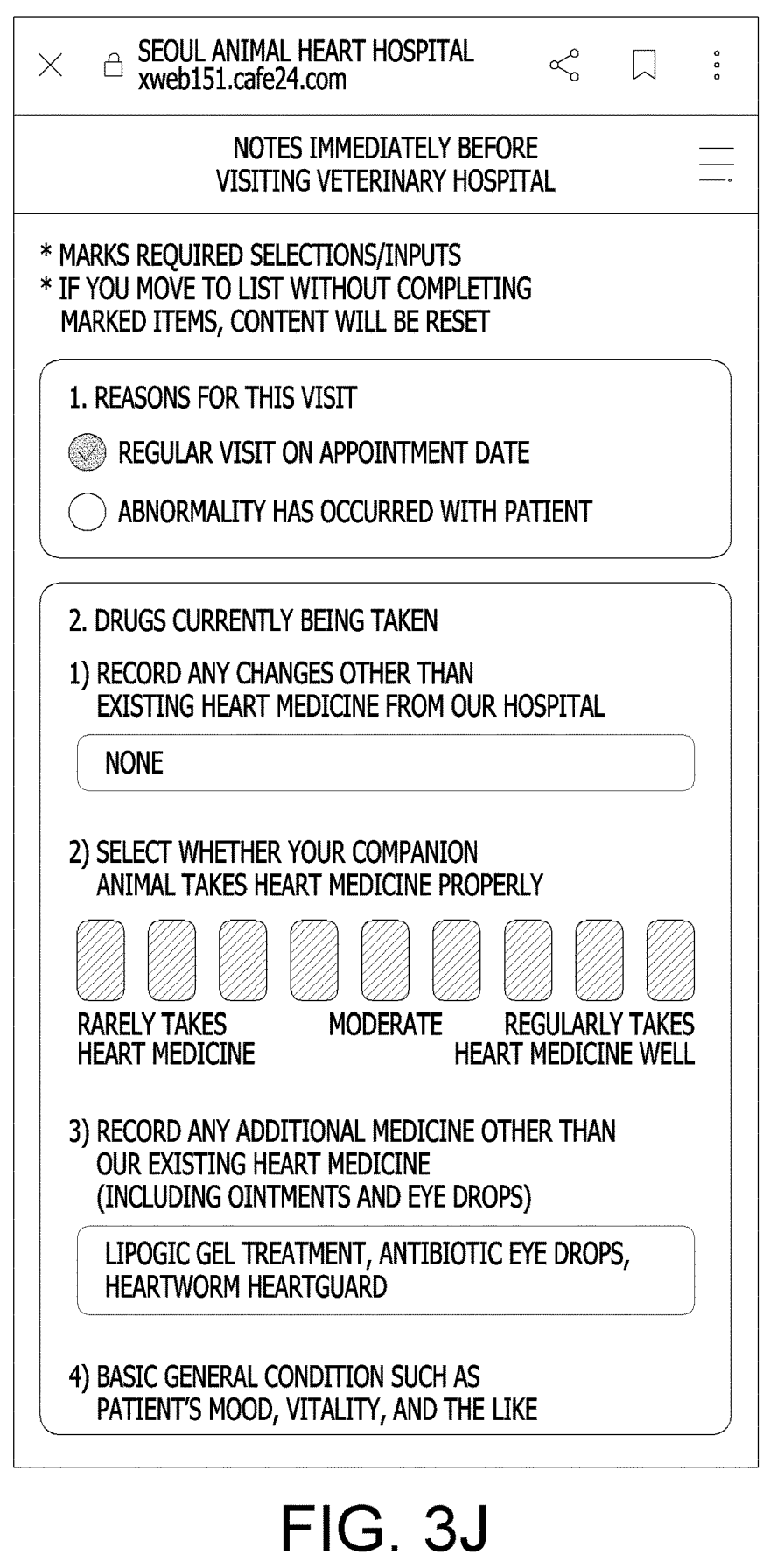

SEOUL ANIMAL HEART HOSPITAL
xweb151.cafe24.com

NOTES IMMEDIATELY BEFORE
VISITING VETERINARY HOSPITAL

* MARKS REQUIRED SELECTIONS/INPUTS
* IF YOU MOVE TO LIST WITHOUT COMPLETING MARKED ITEMS, CONTENT WILL BE RESET

1. REASONS FOR THIS VISIT

REGULAR VISIT ON APPOINTMENT DATE

ABNORMALITY HAS OCCURRED WITH PATIENT

2. DRUGS CURRENTLY BEING TAKEN

1) RECORD ANY CHANGES OTHER THAN EXISTING HEART MEDICINE FROM OUR HOSPITAL

NONE

2) SELECT WHETHER YOUR COMPANION ANIMAL TAKES HEART MEDICINE PROPERLY

RARELY TAKES HEART MEDICINE

MODERATE

REGULARLY TAKES HEART MEDICINE WELL

3) RECORD ANY ADDITIONAL MEDICINE OTHER THAN OUR EXISTING HEART MEDICINE (INCLUDING OINTMENTS AND EYE DROPS)

LIPOGIC GEL TREATMENT, ANTIBIOTIC EYE DROPS, HEARTWORM HEARTGUARD

4) BASIC GENERAL CONDITION SUCH AS PATIENT'S MOOD, VITALITY, AND THE LIKE

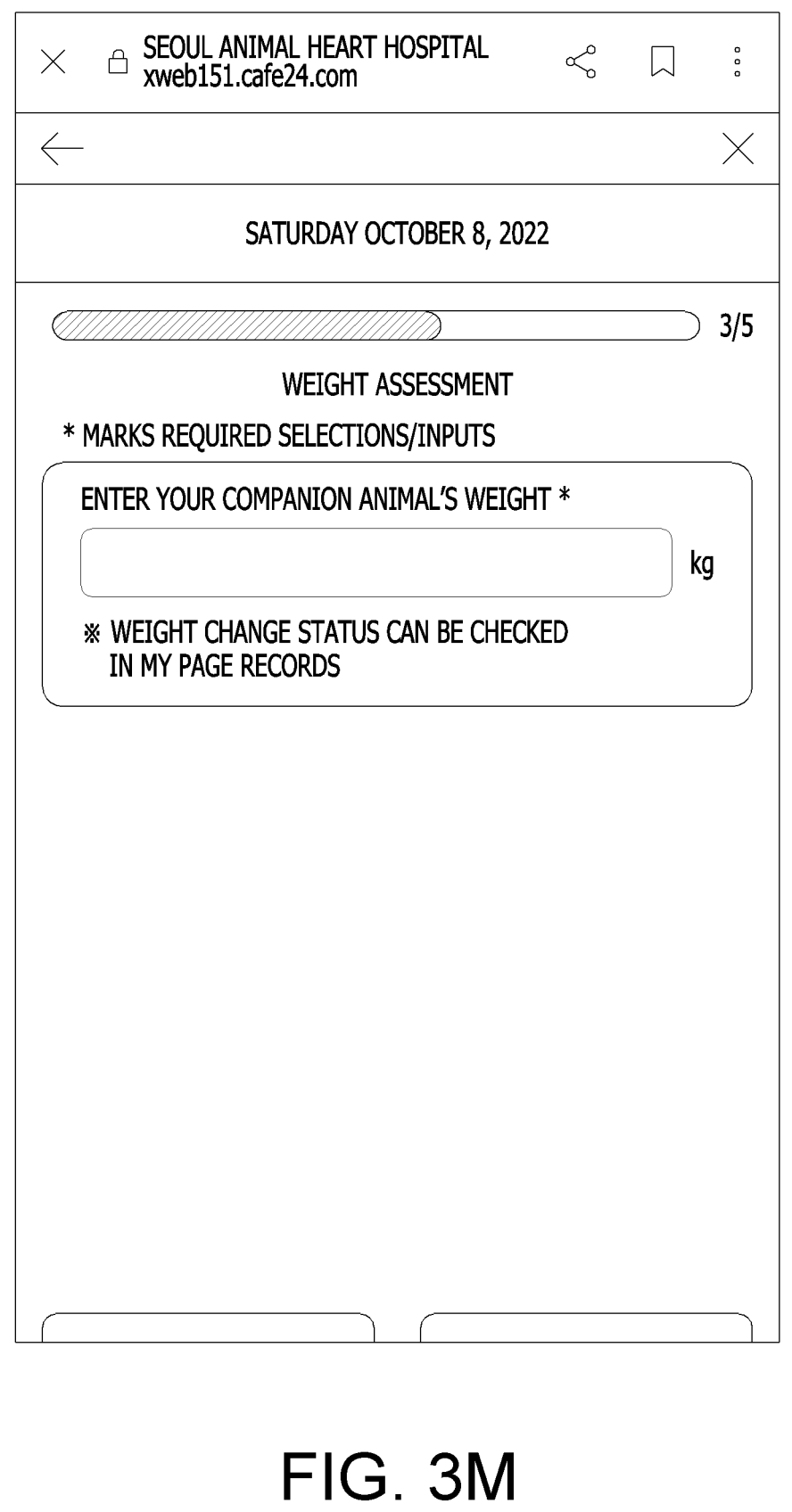

SEOUL ANIMAL HEART HOSPITAL
xweb151.cafe24.com

SATURDAY OCTOBER 8, 2022

3/5

WEIGHT ASSESSMENT

* MARKS REQUIRED SELECTIONS/INPUTS

ENTER YOUR COMPANION ANIMAL'S WEIGHT * kg

※ WEIGHT CHANGE STATUS CAN BE CHECKED IN MY PAGE RECORDS

FIG. 3M

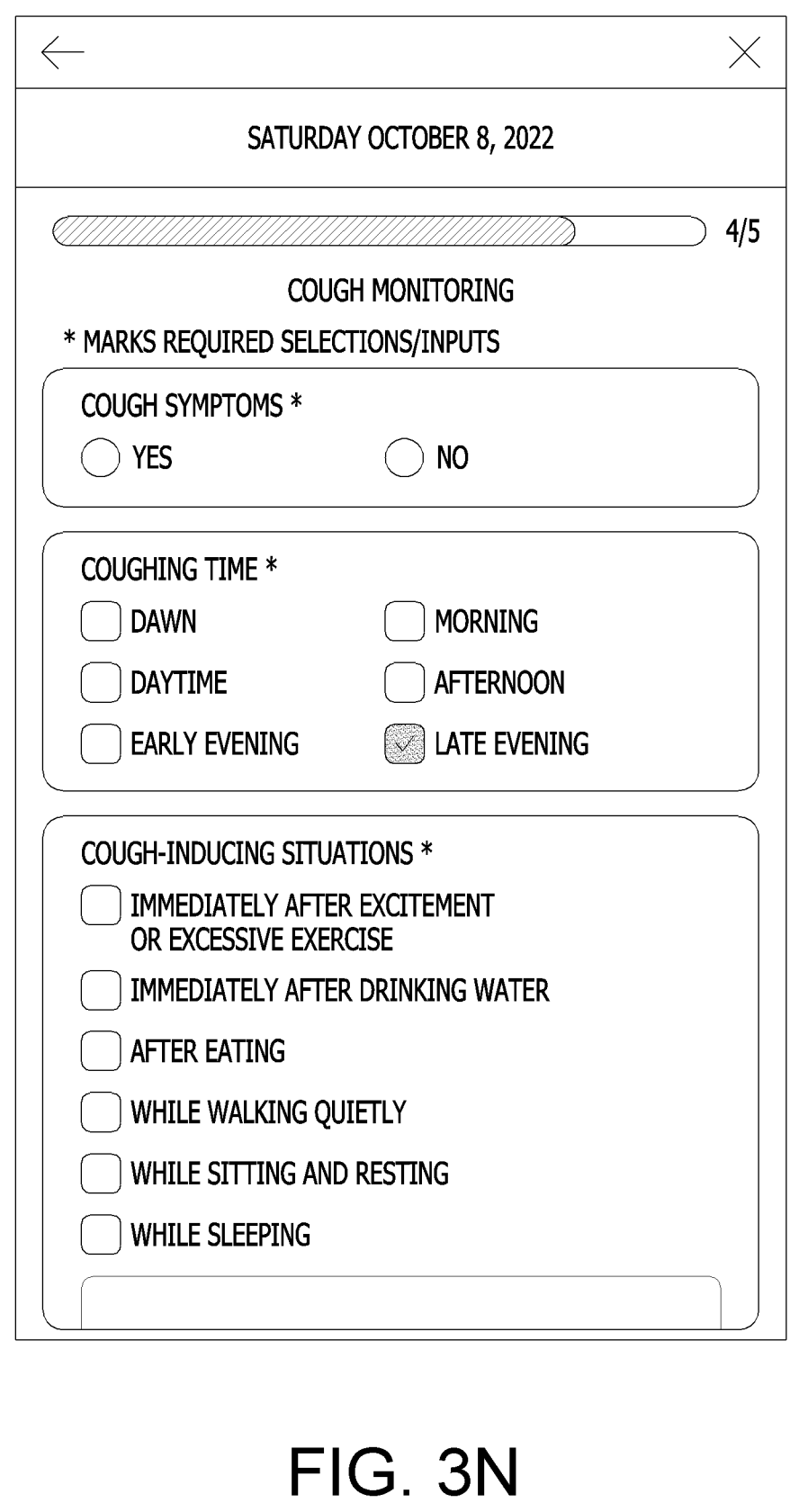

SATURDAY OCTOBER 8, 2022

4/5

COUGH MONITORING

* MARKS REQUIRED SELECTIONS/INPUTS

COUGH SYMPTOMS *

YES NO

COUGHING TIME *

DAWN MORNING

DAYTIME AFTERNOON

EARLY EVENING LATE EVENING

COUGH-INDUCING SITUATIONS *

IMMEDIATELY AFTER EXCITEMENT OR EXCESSIVE EXERCISE

IMMEDIATELY AFTER DRINKING WATER

AFTER EATING

WHILE WALKING QUIETLY

WHILE SITTING AND RESTING

WHILE SLEEPING

FIG. 3N

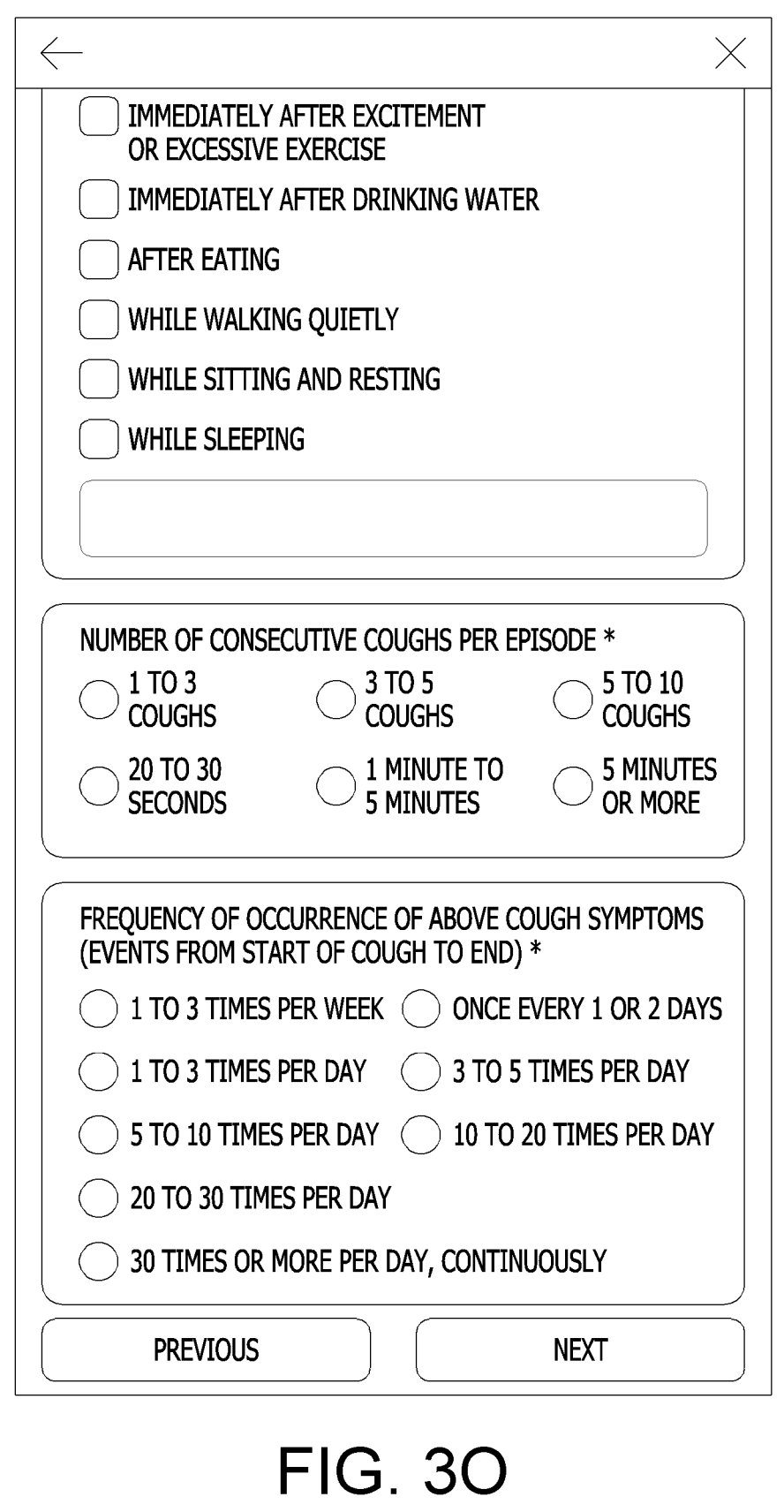

IMMEDIATELY AFTER EXCITEMENT OR EXCESSIVE EXERCISE
IMMEDIATELY AFTER DRINKING WATER
AFTER EATING
WHILE WALKING QUIETLY
WHILE SITTING AND RESTING
WHILE SLEEPING

NUMBER OF CONSECUTIVE COUGHS PER EPISODE *
1 TO 3 COUGHS
3 TO 5 COUGHS
5 TO 10 COUGHS
20 TO 30 SECONDS
1 MINUTE TO 5 MINUTES
5 MINUTES OR MORE

FREQUENCY OF OCCURRENCE OF ABOVE COUGH SYMPTOMS (EVENTS FROM START OF COUGH TO END) *
1 TO 3 TIMES PER WEEK
ONCE EVERY 1 OR 2 DAYS
1 TO 3 TIMES PER DAY
3 TO 5 TIMES PER DAY
5 TO 10 TIMES PER DAY
10 TO 20 TIMES PER DAY
20 TO 30 TIMES PER DAY
30 TIMES OR MORE PER DAY, CONTINUOUSLY

PREVIOUS
NEXT

FIG. 3O

Figure 3P:
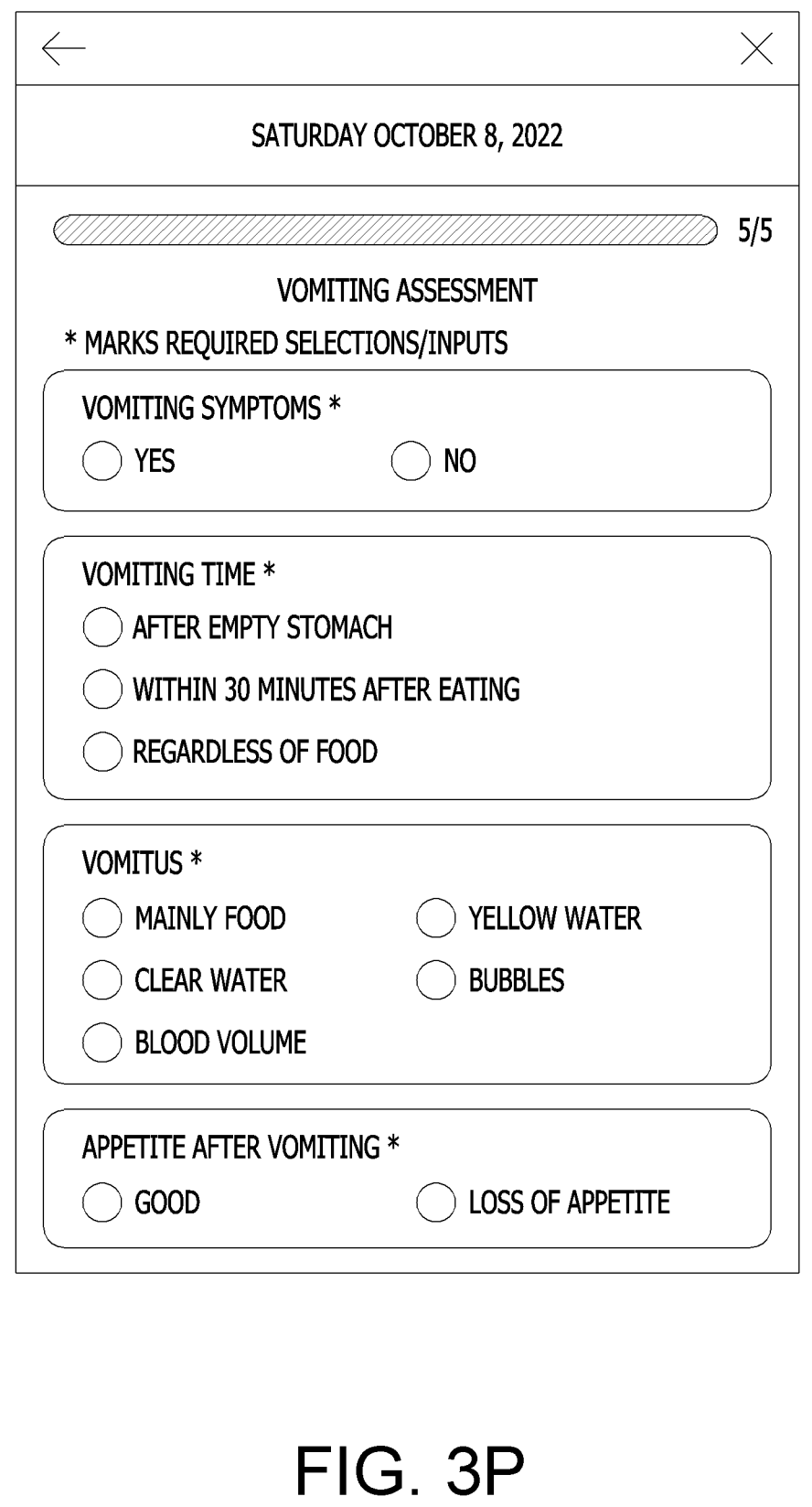

SATURDAY OCTOBER 8, 2022

5/5

VOMITING ASSESSMENT

* MARKS REQUIRED SELECTIONS/INPUTS

VOMITING SYMPTOMS *

YES
NO

VOMITING TIME *

AFTER EMPTY STOMACH
WITHIN 30 MINUTES AFTER EATING
REGARDLESS OF FOOD

VOMITUS *

MAINLY FOOD
YELLOW WATER
CLEAR WATER
BUBBLES
BLOOD VOLUME

APPETITE AFTER VOMITING *

GOOD
LOSS OF APPETITE

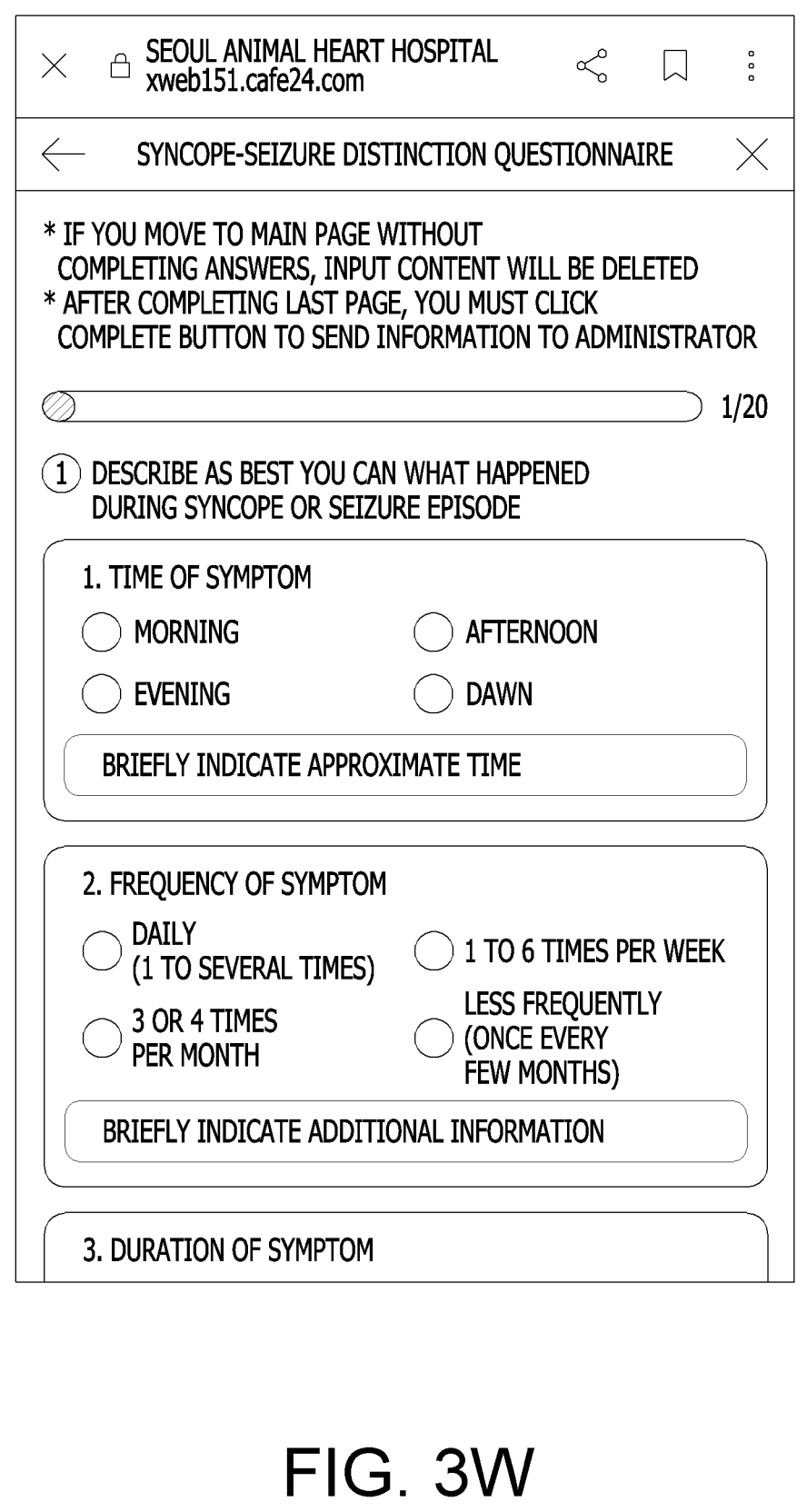

SEOUL ANIMAL HEART HOSPITAL
xweb151.cafe24.com

SYNCOPE-SEIZURE DISTINCTION QUESTIONNAIRE

* IF YOU MOVE TO MAIN PAGE WITHOUT COMPLETING ANSWERS, INPUT CONTENT WILL BE DELETED
* AFTER COMPLETING LAST PAGE, YOU MUST CLICK COMPLETE BUTTON TO SEND INFORMATION TO ADMINISTRATOR

1/20

(1) DESCRIBE AS BEST YOU CAN WHAT HAPPENED DURING SYNCOPE OR SEIZURE EPISODE

1. TIME OF SYMPTOM

MORNING
AFTERNOON
EVENING
DAWN

BRIEFLY INDICATE APPROXIMATE TIME

2. FREQUENCY OF SYMPTOM

DAILY (1 TO SEVERAL TIMES)
1 TO 6 TIMES PER WEEK
3 OR 4 TIMES PER MONTH
LESS FREQUENTLY (ONCE EVERY FEW MONTHS)

BRIEFLY INDICATE ADDITIONAL INFORMATION

3. DURATION OF SYMPTOM

FIG. 3W

Figure 3X:
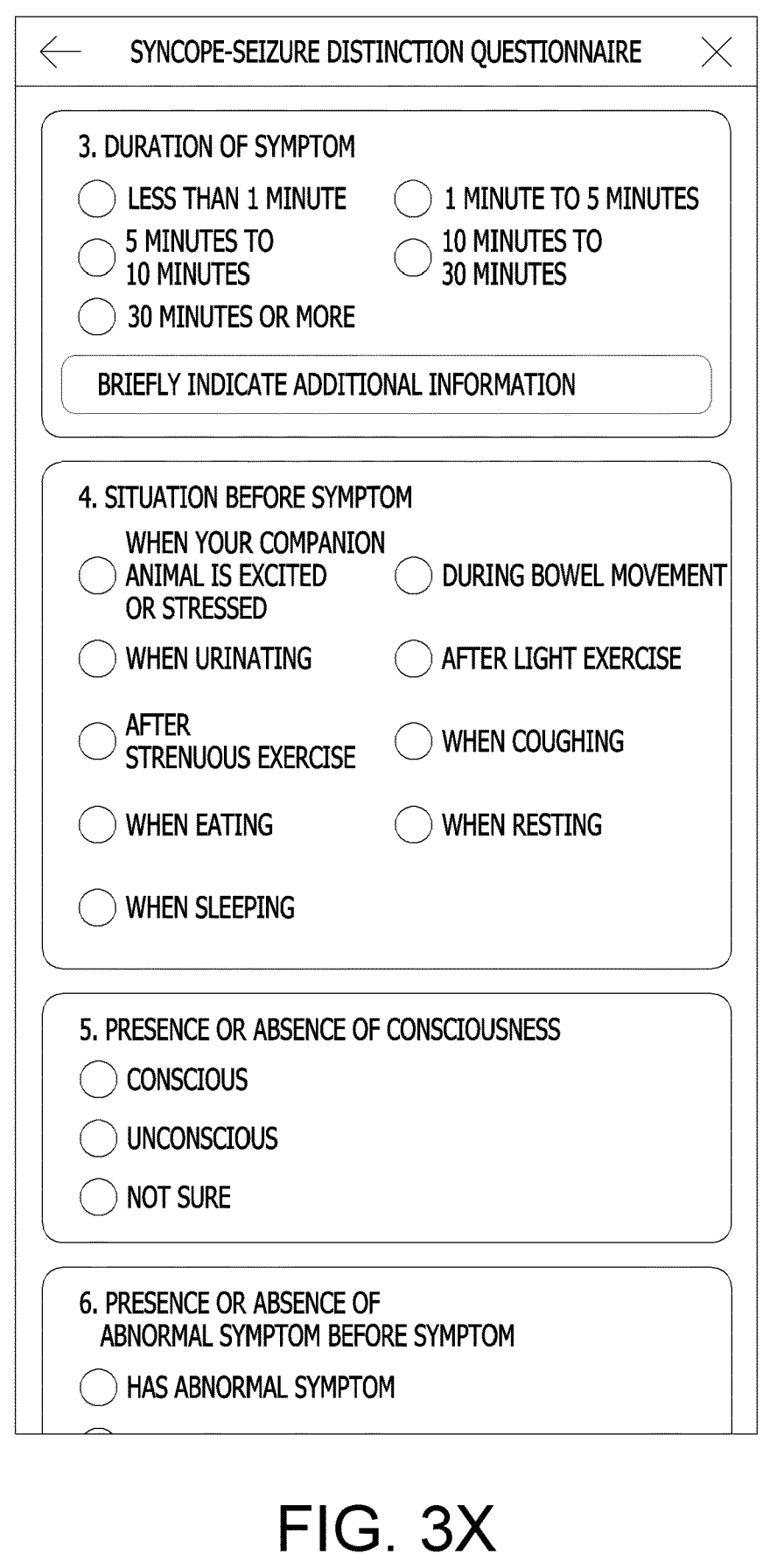

SYNCOPE-SEIZURE DISTINCTION QUESTIONNAIRE

3. DURATION OF SYMPTOM

- LESS THAN 1 MINUTE
- 1 MINUTE TO 5 MINUTES
- 5 MINUTES TO 10 MINUTES
- 10 MINUTES TO 30 MINUTES
- 30 MINUTES OR MORE

BRIEFLY INDICATE ADDITIONAL INFORMATION

4. SITUATION BEFORE SYMPTOM

- WHEN YOUR COMPANION ANIMAL IS EXCITED OR STRESSED
- DURING BOWEL MOVEMENT
- WHEN URINATING
- AFTER LIGHT EXERCISE
- AFTER STRENUOUS EXERCISE
- WHEN COUGHING
- WHEN EATING
- WHEN RESTING
- WHEN SLEEPING

5. PRESENCE OR ABSENCE OF CONSCIOUSNESS

- CONSCIOUS
- UNCONSCIOUS
- NOT SURE

6. PRESENCE OR ABSENCE OF ABNORMAL SYMPTOM BEFORE SYMPTOM

- HAS ABNORMAL SYMPTOM

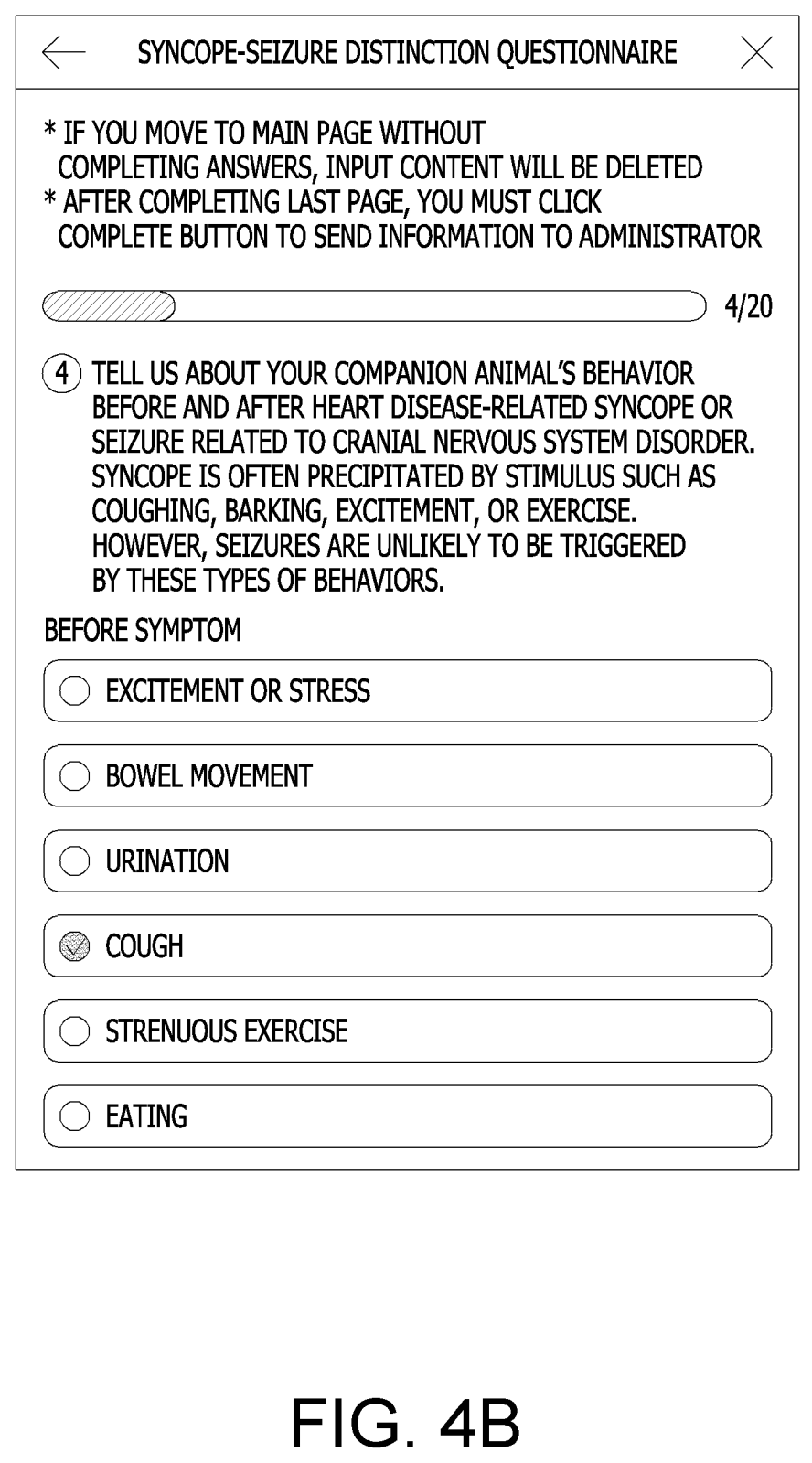

SYNCOPE-SEIZURE DISTINCTION QUESTIONNAIRE

* IF YOU MOVE TO MAIN PAGE WITHOUT COMPLETING ANSWERS, INPUT CONTENT WILL BE DELETED
* AFTER COMPLETING LAST PAGE, YOU MUST CLICK COMPLETE BUTTON TO SEND INFORMATION TO ADMINISTRATOR

4/20

(4) TELL US ABOUT YOUR COMPANION ANIMAL'S BEHAVIOR BEFORE AND AFTER HEART DISEASE-RELATED SYNCOPE OR SEIZURE RELATED TO CRANIAL NERVOUS SYSTEM DISORDER. SYNCOPE IS OFTEN PRECIPITATED BY STIMULUS SUCH AS COUGHING, BARKING, EXCITEMENT, OR EXERCISE. HOWEVER, SEIZURES ARE UNLIKELY TO BE TRIGGERED BY THESE TYPES OF BEHAVIORS.

BEFORE SYMPTOM

- EXCITEMENT OR STRESS
- BOWEL MOVEMENT
- URINATION
- COUGH
- STRENUOUS EXERCISE
- EATING

FIG. 4B

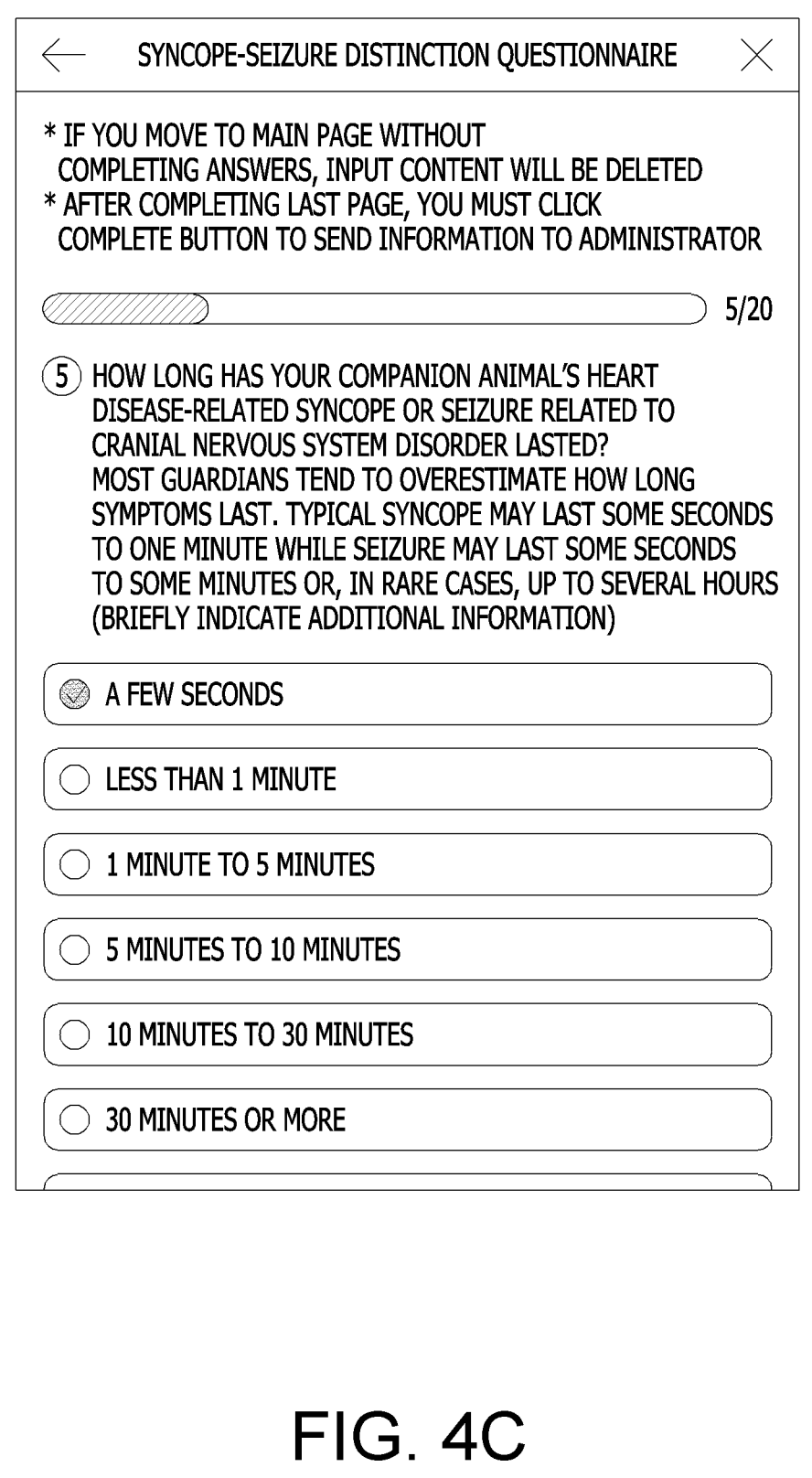

SYNCOPE-SEIZURE DISTINCTION QUESTIONNAIRE

* IF YOU MOVE TO MAIN PAGE WITHOUT COMPLETING ANSWERS, INPUT CONTENT WILL BE DELETED
* AFTER COMPLETING LAST PAGE, YOU MUST CLICK COMPLETE BUTTON TO SEND INFORMATION TO ADMINISTRATOR

5/20

(5) HOW LONG HAS YOUR COMPANION ANIMAL'S HEART DISEASE-RELATED SYNCOPE OR SEIZURE RELATED TO CRANIAL NERVOUS SYSTEM DISORDER LASTED?
MOST GUARDIANS TEND TO OVERESTIMATE HOW LONG SYMPTOMS LAST. TYPICAL SYNCOPE MAY LAST SOME SECONDS TO ONE MINUTE WHILE SEIZURE MAY LAST SOME SECONDS TO SOME MINUTES OR, IN RARE CASES, UP TO SEVERAL HOURS (BRIEFLY INDICATE ADDITIONAL INFORMATION)

- A FEW SECONDS
- LESS THAN 1 MINUTE
- 1 MINUTE TO 5 MINUTES
- 5 MINUTES TO 10 MINUTES
- 10 MINUTES TO 30 MINUTES
- 30 MINUTES OR MORE

FIG. 4C

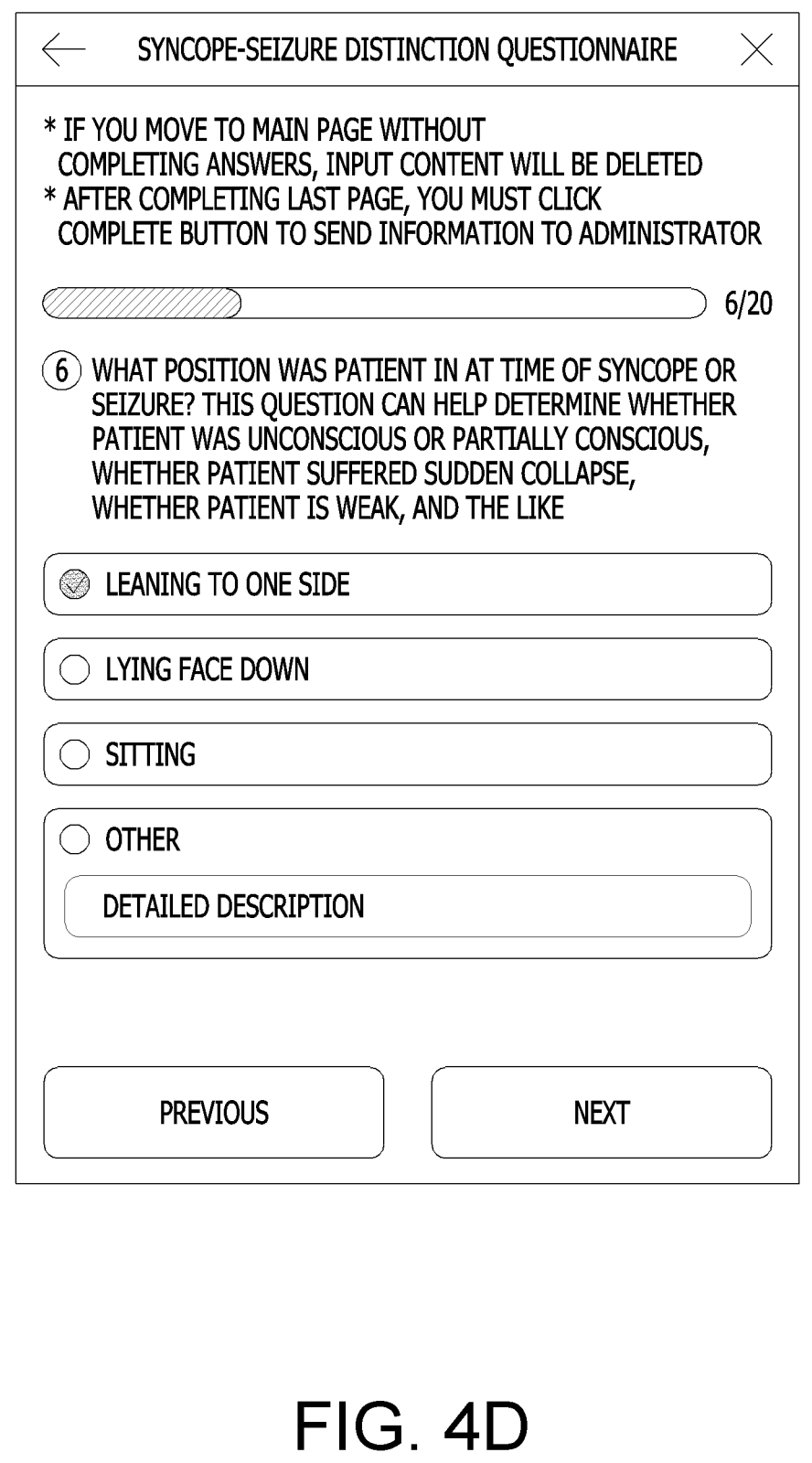

SYNCOPE-SEIZURE DISTINCTION QUESTIONNAIRE

* IF YOU MOVE TO MAIN PAGE WITHOUT COMPLETING ANSWERS, INPUT CONTENT WILL BE DELETED
* AFTER COMPLETING LAST PAGE, YOU MUST CLICK COMPLETE BUTTON TO SEND INFORMATION TO ADMINISTRATOR

6/20

(6) WHAT POSITION WAS PATIENT IN AT TIME OF SYNCOPE OR SEIZURE? THIS QUESTION CAN HELP DETERMINE WHETHER PATIENT WAS UNCONSCIOUS OR PARTIALLY CONSCIOUS, WHETHER PATIENT SUFFERED SUDDEN COLLAPSE, WHETHER PATIENT IS WEAK, AND THE LIKE

LEANING TO ONE SIDE

LYING FACE DOWN

SITTING

OTHER

DETAILED DESCRIPTION

PREVIOUS

NEXT

FIG. 4D

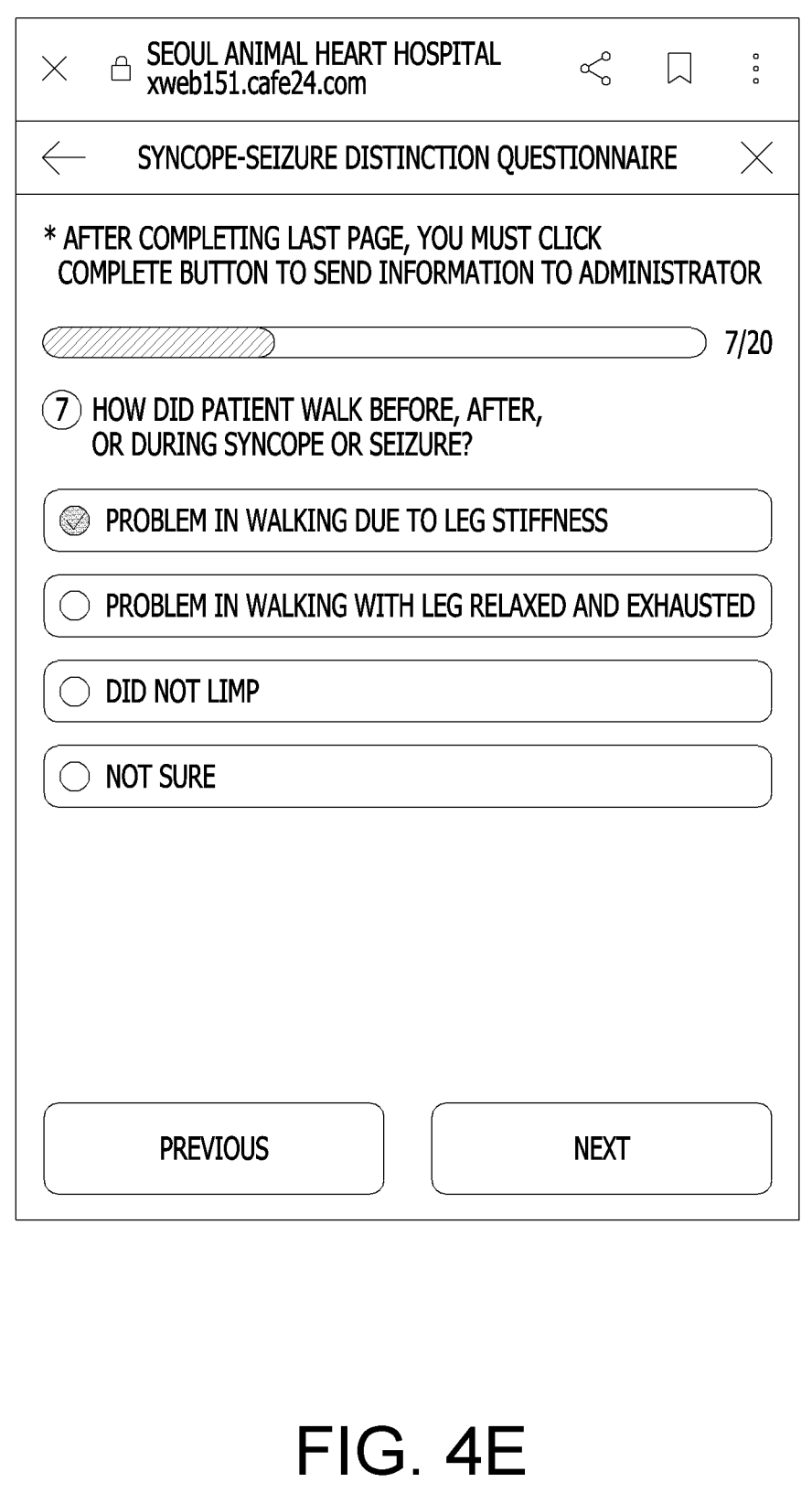

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

7/20

(7) HOW DID PATIENT WALK BEFORE, AFTER, OR DURING SYNCOPE OR SEIZURE?

- PROBLEM IN WALKING DUE TO LEG STIFFNESS
- PROBLEM IN WALKING WITH LEG RELAXED AND EXHAUSTED
- DID NOT LIMP
- NOT SURE

PREVIOUS NEXT

FIG. 4E

Figure 4F:
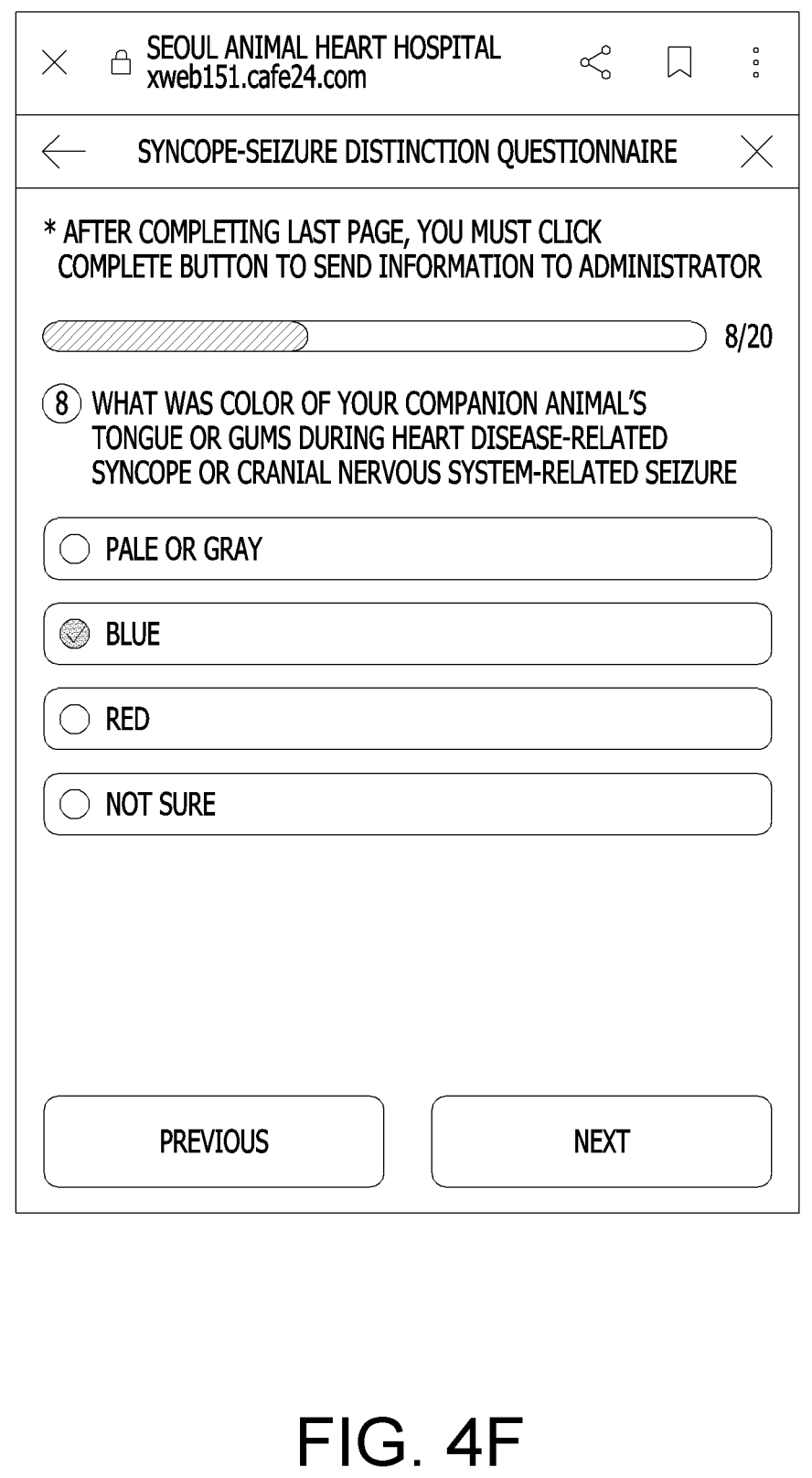

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

8/20

(8) WHAT WAS COLOR OF YOUR COMPANION ANIMAL'S TONGUE OR GUMS DURING HEART DISEASE-RELATED SYNCOPE OR CRANIAL NERVOUS SYSTEM-RELATED SEIZURE

PALE OR GRAY

BLUE

RED

NOT SURE

PREVIOUS

NEXT

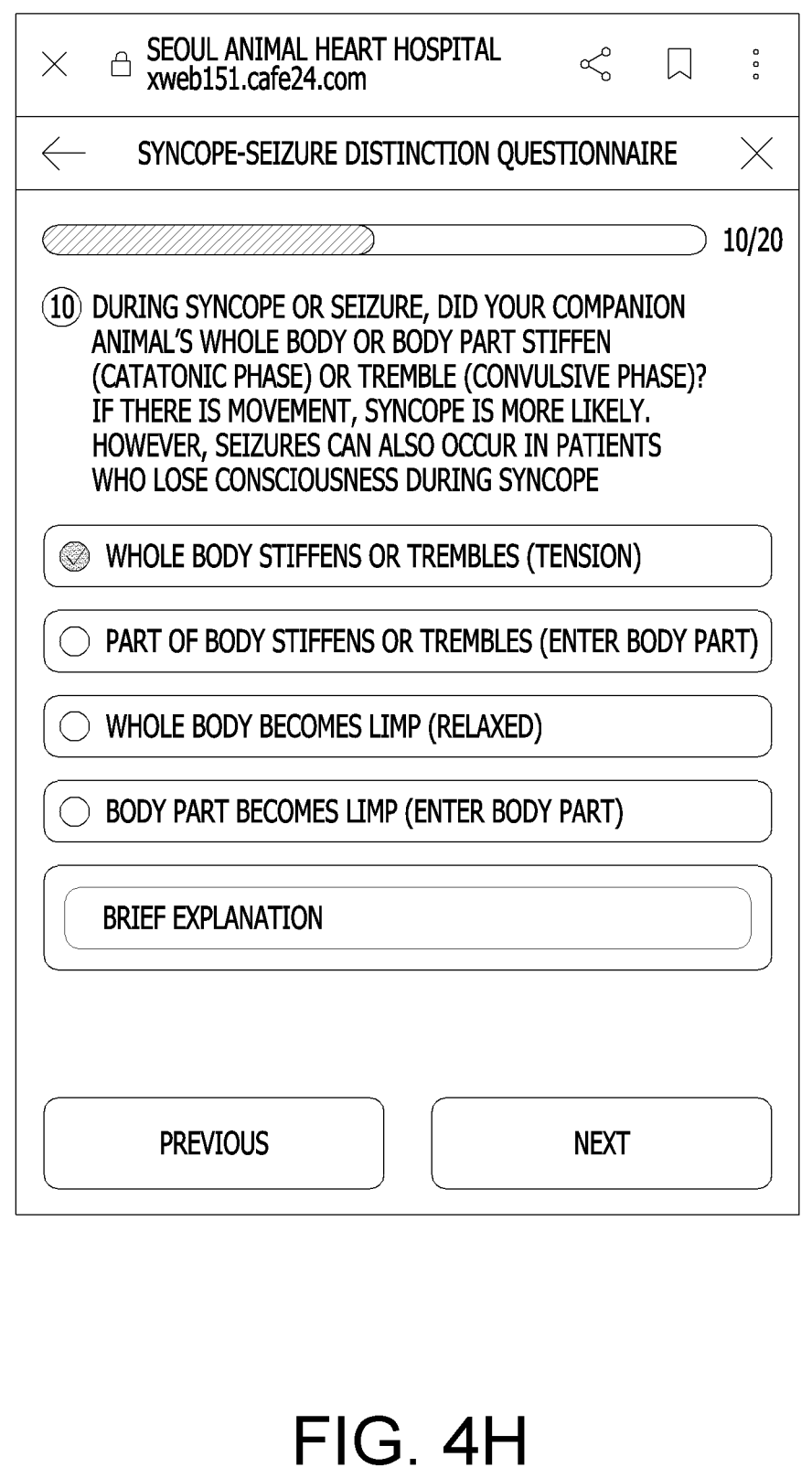

SEOUL ANIMAL HEART HOSPITAL
xweb151.cafe24.com

SYNCOPE-SEIZURE DISTINCTION QUESTIONNAIRE

10/20

(10) DURING SYNCOPE OR SEIZURE, DID YOUR COMPANION ANIMAL'S WHOLE BODY OR BODY PART STIFFEN (CATATONIC PHASE) OR TREMBLE (CONVULSIVE PHASE)? IF THERE IS MOVEMENT, SYNCOPE IS MORE LIKELY. HOWEVER, SEIZURES CAN ALSO OCCUR IN PATIENTS WHO LOSE CONSCIOUSNESS DURING SYNCOPE

WHOLE BODY STIFFENS OR TREMBLES (TENSION)

PART OF BODY STIFFENS OR TREMBLES (ENTER BODY PART)

WHOLE BODY BECOMES LIMP (RELAXED)

BODY PART BECOMES LIMP (ENTER BODY PART)

BRIEF EXPLANATION

PREVIOUS

NEXT

FIG. 4H

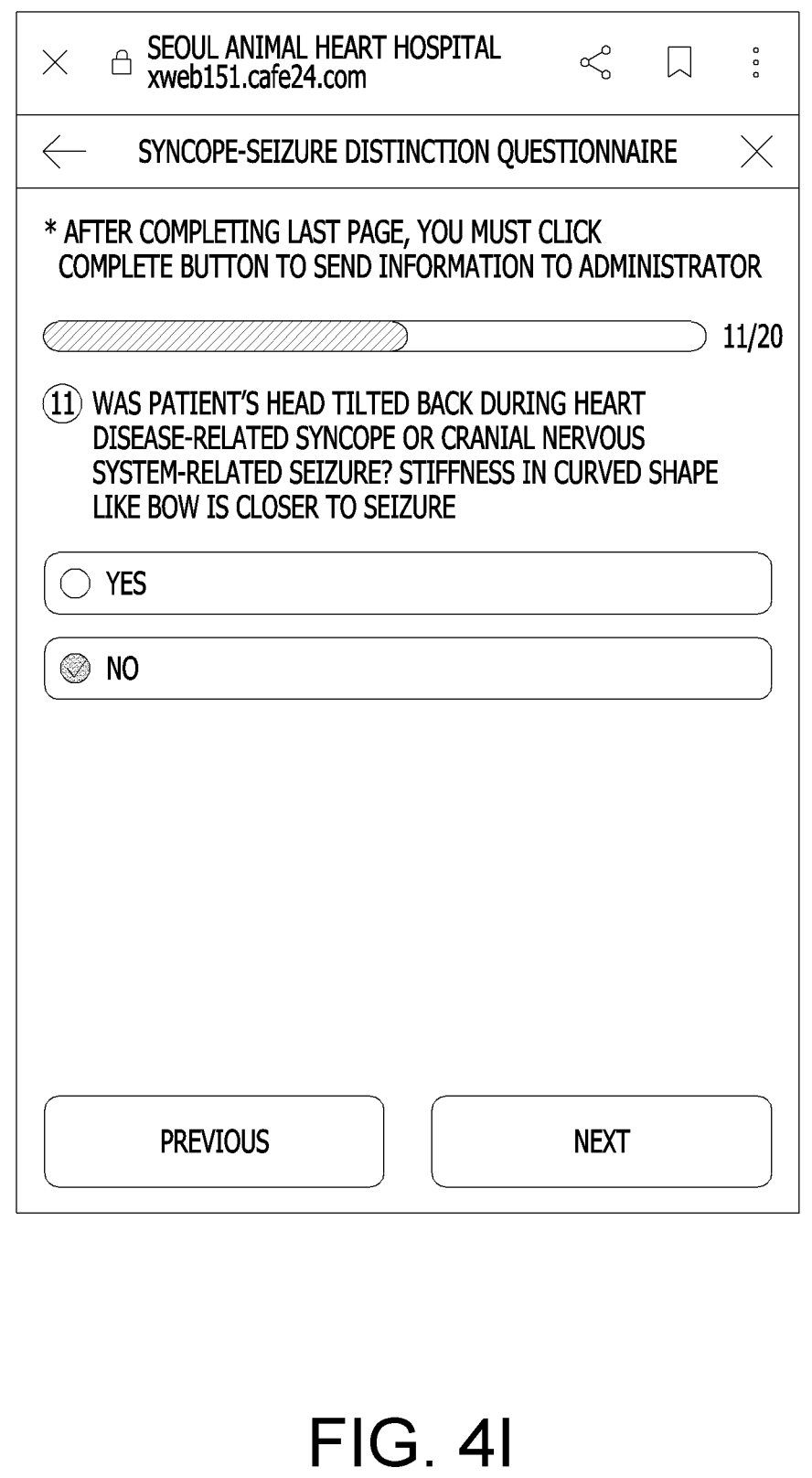

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

11/20

(11) WAS PATIENT'S HEAD TILTED BACK DURING HEART DISEASE-RELATED SYNCOPE OR CRANIAL NERVOUS SYSTEM-RELATED SEIZURE? STIFFNESS IN CURVED SHAPE LIKE BOW IS CLOSER TO SEIZURE

YES

NO

PREVIOUS

NEXT

FIG. 4I

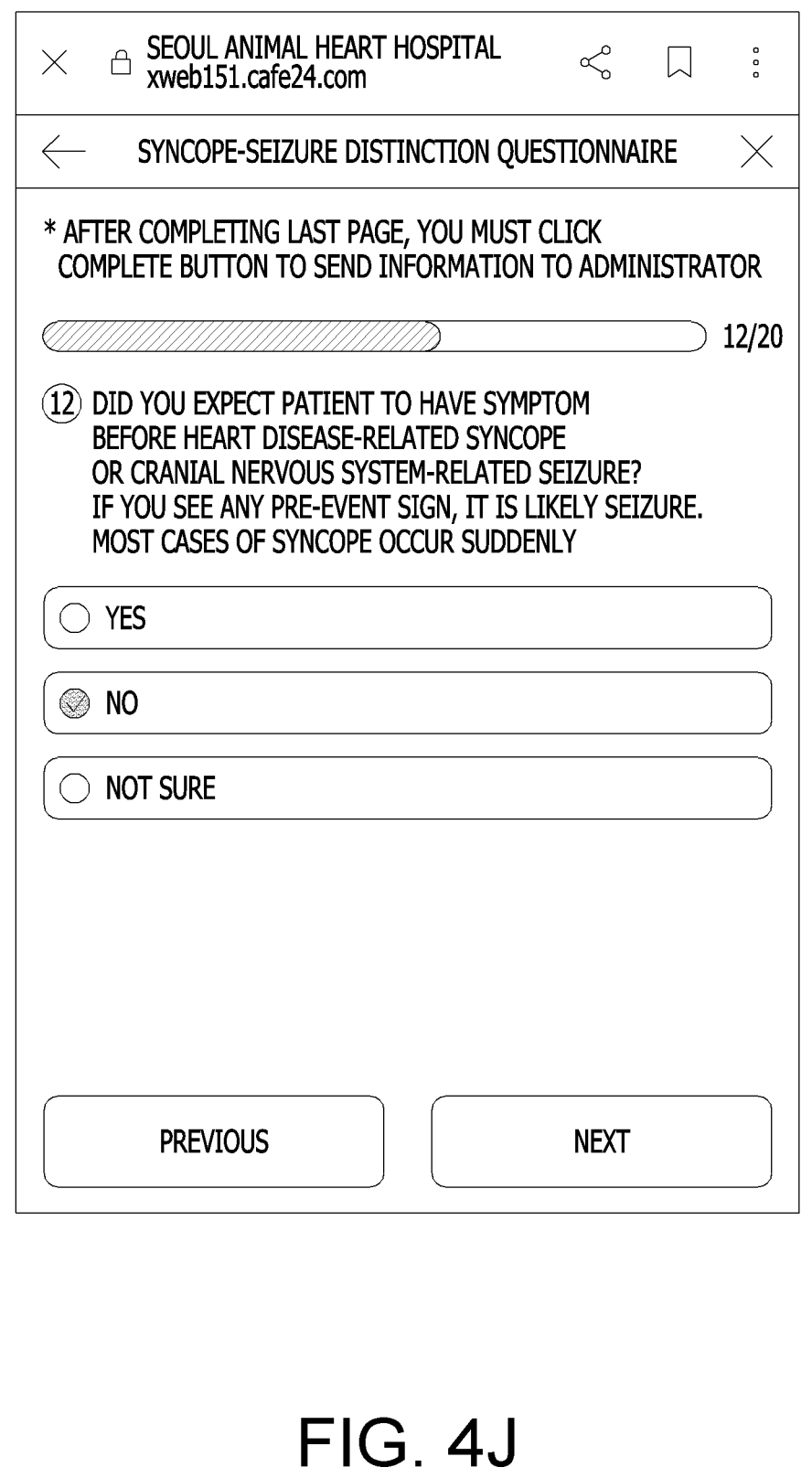

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

12/20

(12) DID YOU EXPECT PATIENT TO HAVE SYMPTOM BEFORE HEART DISEASE-RELATED SYNCOPE OR CRANIAL NERVOUS SYSTEM-RELATED SEIZURE? IF YOU SEE ANY PRE-EVENT SIGN, IT IS LIKELY SEIZURE. MOST CASES OF SYNCOPE OCCUR SUDDENLY

YES

NO

NOT SURE

PREVIOUS

NEXT

FIG. 4J

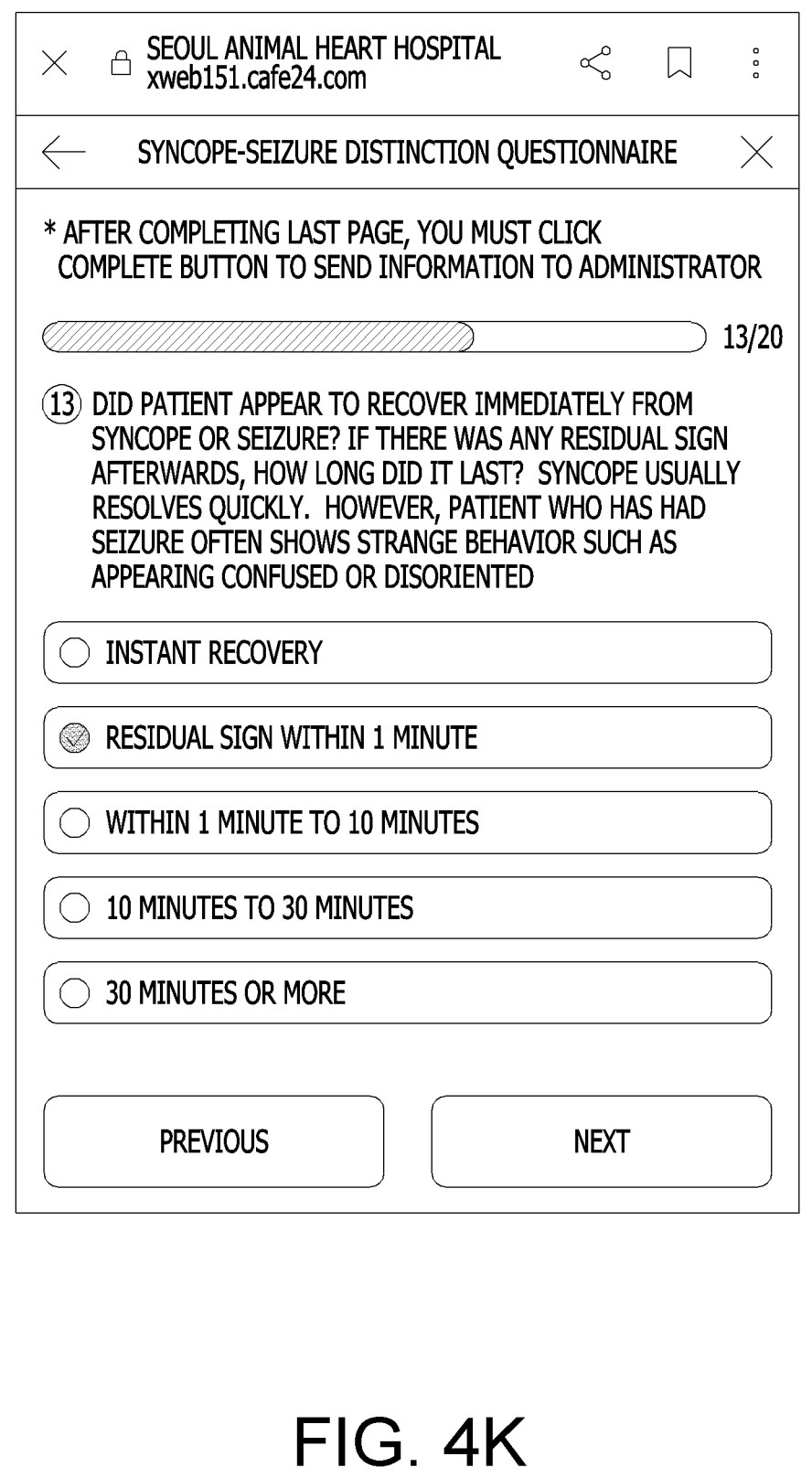

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

13/20

(13) DID PATIENT APPEAR TO RECOVER IMMEDIATELY FROM SYNCOPE OR SEIZURE? IF THERE WAS ANY RESIDUAL SIGN AFTERWARDS, HOW LONG DID IT LAST? SYNCOPE USUALLY RESOLVES QUICKLY. HOWEVER, PATIENT WHO HAS HAD SEIZURE OFTEN SHOWS STRANGE BEHAVIOR SUCH AS APPEARING CONFUSED OR DISORIENTED

INSTANT RECOVERY

RESIDUAL SIGN WITHIN 1 MINUTE

WITHIN 1 MINUTE TO 10 MINUTES

10 MINUTES TO 30 MINUTES

30 MINUTES OR MORE

PREVIOUS

NEXT

FIG. 4K

Figure 4M:
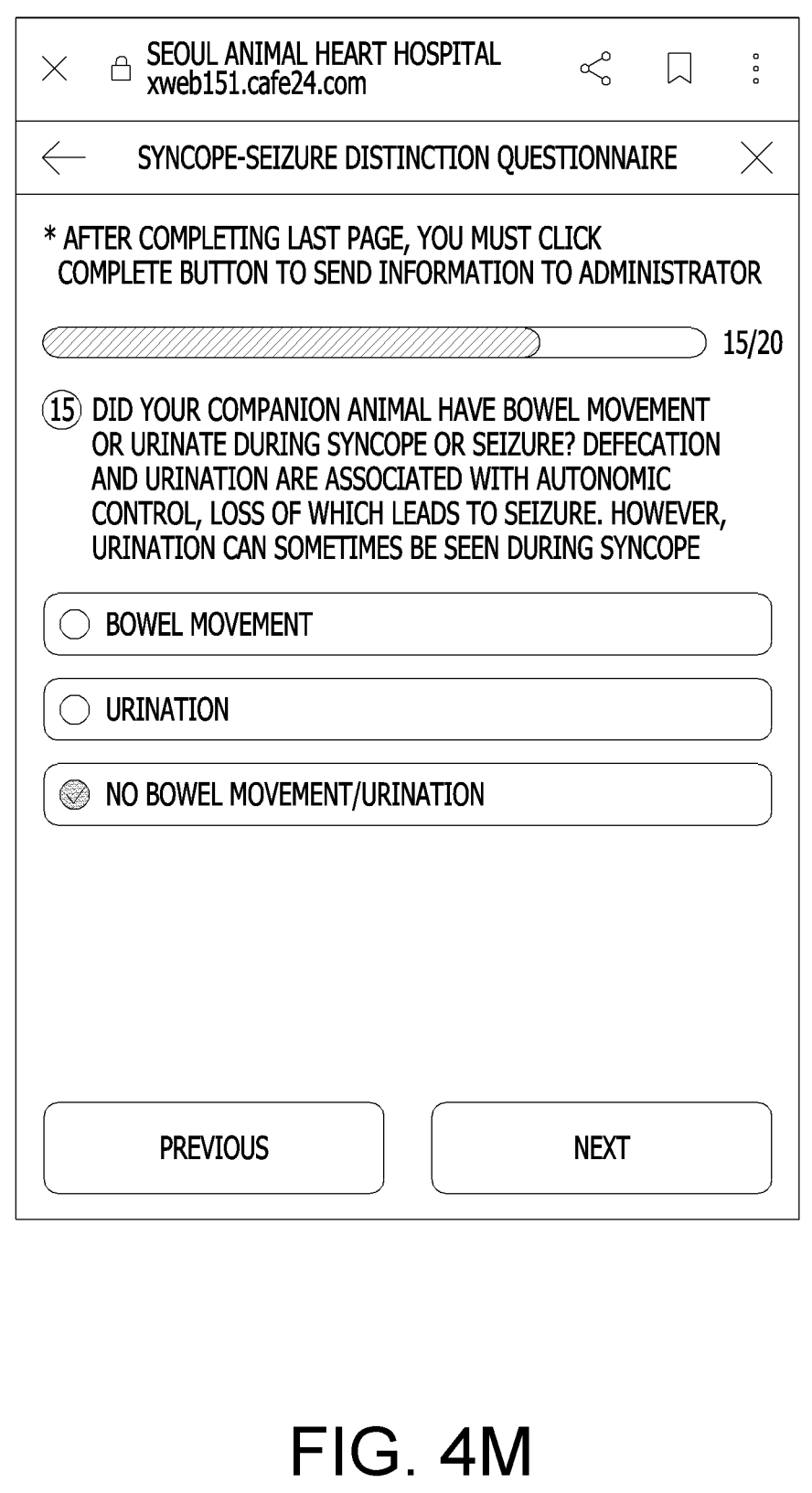

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

15/20

(15) DID YOUR COMPANION ANIMAL HAVE BOWEL MOVEMENT OR URINATE DURING SYNCOPE OR SEIZURE? DEFECATION AND URINATION ARE ASSOCIATED WITH AUTONOMIC CONTROL, LOSS OF WHICH LEADS TO SEIZURE. HOWEVER, URINATION CAN SOMETIMES BE SEEN DURING SYNCOPE

BOWEL MOVEMENT

URINATION

NO BOWEL MOVEMENT/URINATION

PREVIOUS

NEXT

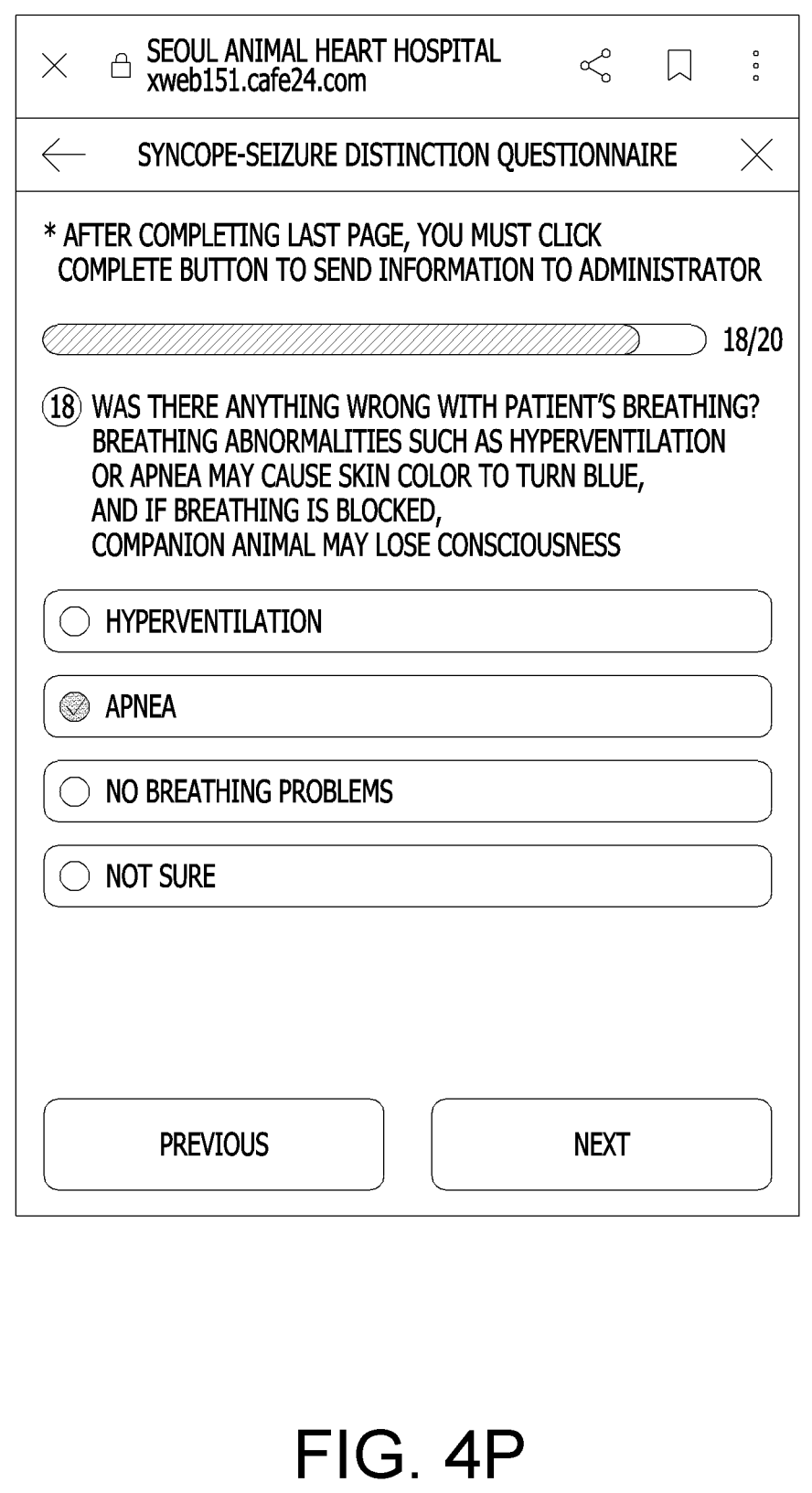

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

18/20

(18) WAS THERE ANYTHING WRONG WITH PATIENT'S BREATHING? BREATHING ABNORMALITIES SUCH AS HYPERVENTILATION OR APNEA MAY CAUSE SKIN COLOR TO TURN BLUE, AND IF BREATHING IS BLOCKED, COMPANION ANIMAL MAY LOSE CONSCIOUSNESS

- HYPERVENTILATION
- APNEA
- NO BREATHING PROBLEMS
- NOT SURE

PREVIOUS NEXT

FIG. 4P

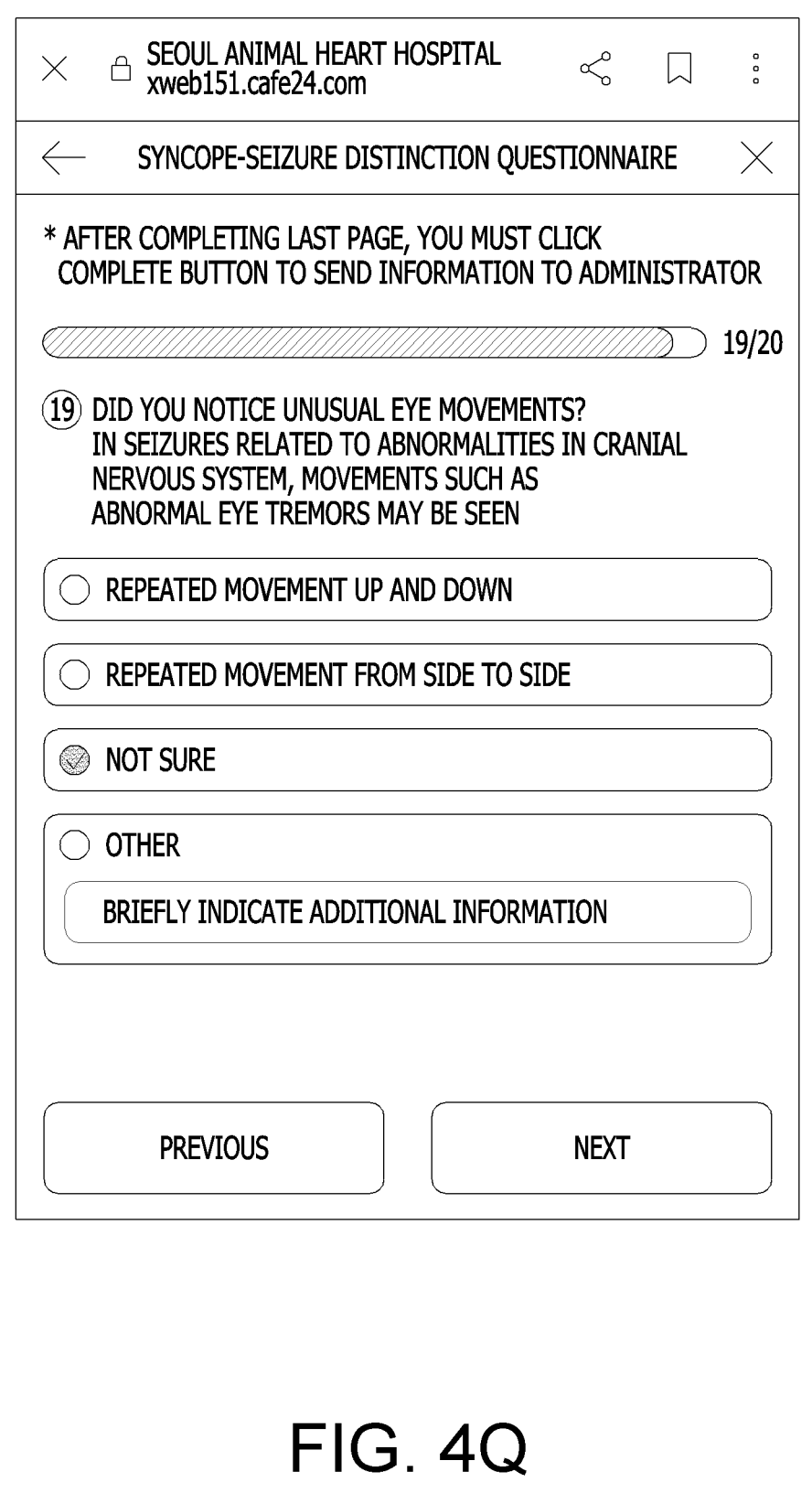

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

19/20

(19) DID YOU NOTICE UNUSUAL EYE MOVEMENTS?
IN SEIZURES RELATED TO ABNORMALITIES IN CRANIAL NERVOUS SYSTEM, MOVEMENTS SUCH AS ABNORMAL EYE TREMORS MAY BE SEEN

- REPEATED MOVEMENT UP AND DOWN
- REPEATED MOVEMENT FROM SIDE TO SIDE
- NOT SURE
- OTHER

BRIEFLY INDICATE ADDITIONAL INFORMATION

PREVIOUS NEXT

FIG. 4Q

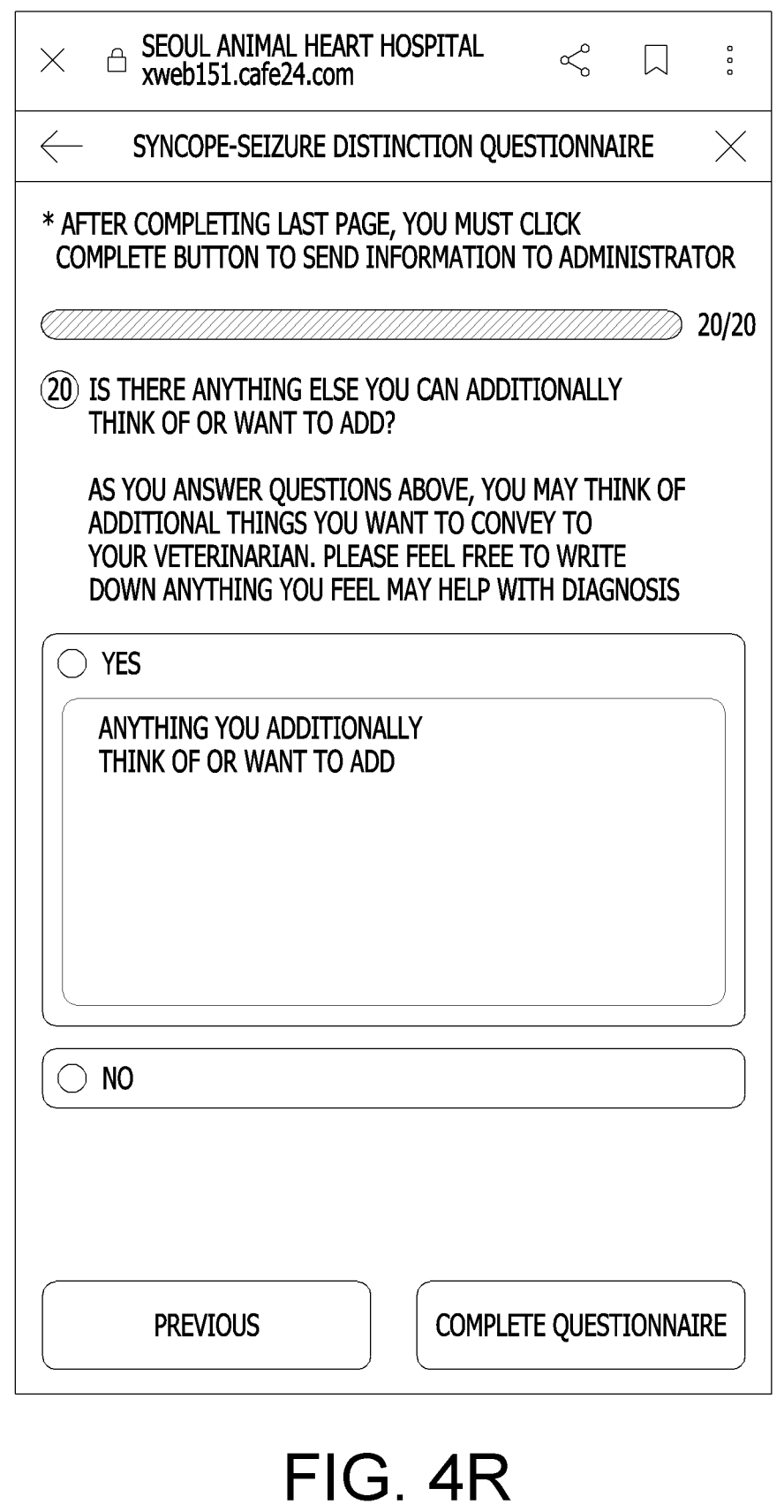

SEOUL ANIMAL HEART HOSPITAL
xweb151.cafe24.com

SYNCOPE-SEIZURE DISTINCTION QUESTIONNAIRE

* AFTER COMPLETING LAST PAGE, YOU MUST CLICK COMPLETE BUTTON TO SEND INFORMATION TO ADMINISTRATOR

20/20

(20) IS THERE ANYTHING ELSE YOU CAN ADDITIONALLY THINK OF OR WANT TO ADD?

AS YOU ANSWER QUESTIONS ABOVE, YOU MAY THINK OF ADDITIONAL THINGS YOU WANT TO CONVEY TO YOUR VETERINARIAN. PLEASE FEEL FREE TO WRITE DOWN ANYTHING YOU FEEL MAY HELP WITH DIAGNOSIS

YES

ANYTHING YOU ADDITIONALLY THINK OF OR WANT TO ADD

NO

PREVIOUS

COMPLETE QUESTIONNAIRE

FIG. 4R

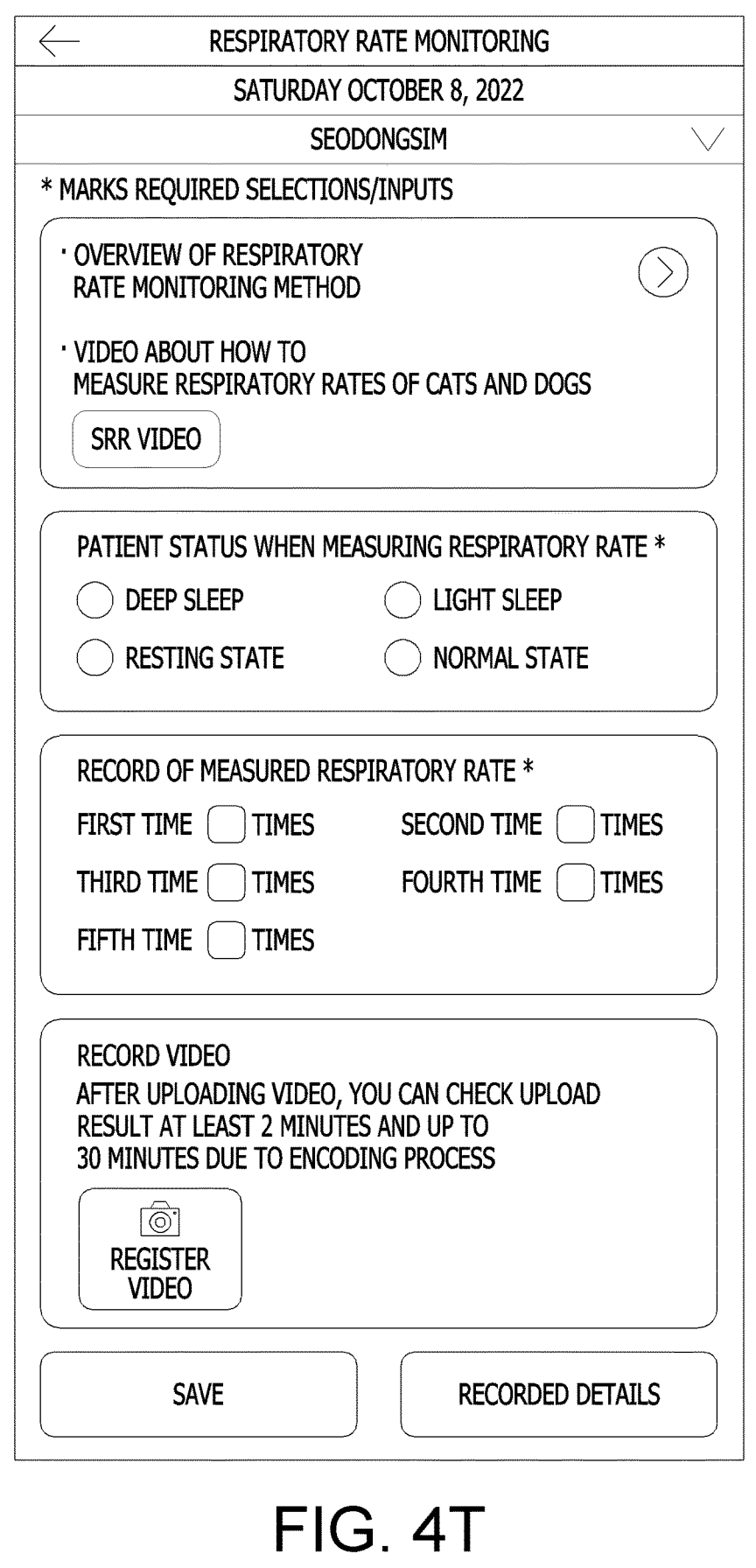

RESPIRATORY RATE MONITORING
SATURDAY OCTOBER 8, 2022
SEODONGSIM
* MARKS REQUIRED SELECTIONS/INPUTS
· OVERVIEW OF RESPIRATORY RATE MONITORING METHOD
· VIDEO ABOUT HOW TO MEASURE RESPIRATORY RATES OF CATS AND DOGS
SRR VIDEO
PATIENT STATUS WHEN MEASURING RESPIRATORY RATE *
DEEP SLEEP
LIGHT SLEEP
RESTING STATE
NORMAL STATE
RECORD OF MEASURED RESPIRATORY RATE *
FIRST TIME TIMES
SECOND TIME TIMES
THIRD TIME TIMES
FOURTH TIME TIMES
FIFTH TIME TIMES
RECORD VIDEO
AFTER UPLOADING VIDEO, YOU CAN CHECK UPLOAD RESULT AT LEAST 2 MINUTES AND UP TO 30 MINUTES DUE TO ENCODING PROCESS
REGISTER VIDEO
SAVE
RECORDED DETAILS

FIG. 4T

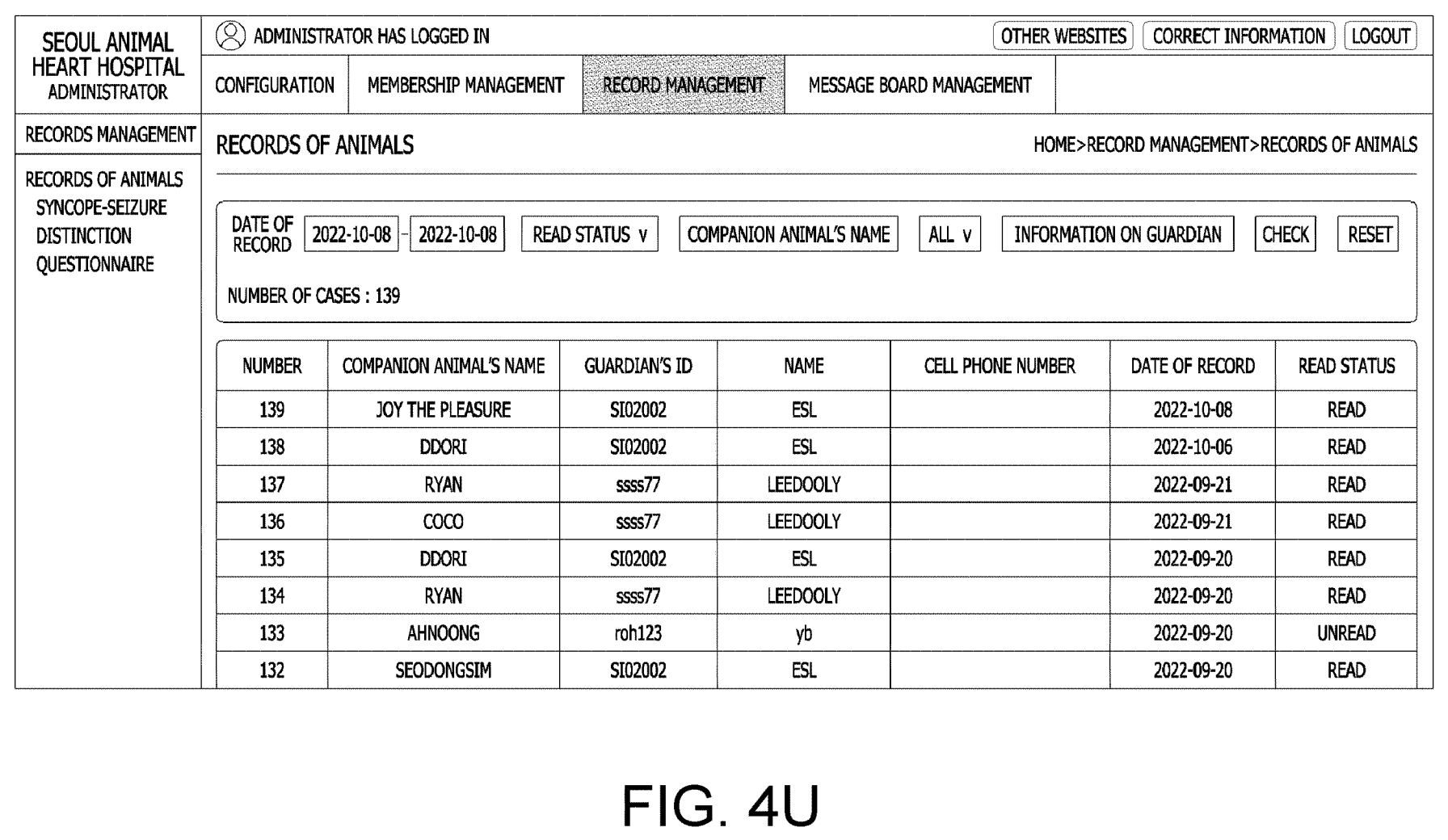

SEOUL ANIMAL HEART HOSPITAL
ADMINISTRATOR

ADMINISTRATOR HAS LOGGED IN

OTHER WEBSITES | CORRECT INFORMATION | LOGOUT

CONFIGURATION | MEMBERSHIP MANAGEMENT | RECORD MANAGEMENT | MESSAGE BOARD MANAGEMENT

RECORDS MANAGEMENT

RECORDS OF ANIMALS
SYNCOPE-SEIZURE
DISTINCTION
QUESTIONNAIRE

RECORDS OF ANIMALS

HOME>RECORD MANAGEMENT>RECORDS OF ANIMALS

DATE OF RECORD 2022-10-08 - 2022-10-08 | READ STATUS v | COMPANION ANIMAL'S NAME | ALL v | INFORMATION ON GUARDIAN | CHECK | RESET

NUMBER OF CASES : 139

| NUMBER | COMPANION ANIMAL'S NAME | GUARDIAN'S ID | NAME | CELL PHONE NUMBER | DATE OF RECORD | READ STATUS |
|---|---|---|---|---|---|---|
| 139 | JOY THE PLEASURE | SI02002 | ESL | | 2022-10-08 | READ |
| 138 | DDORI | SI02002 | ESL | | 2022-10-06 | READ |
| 137 | RYAN | ssss77 | LEEDOOLY | | 2022-09-21 | READ |
| 136 | COCO | ssss77 | LEEDOOLY | | 2022-09-21 | READ |
| 135 | DDORI | SI02002 | ESL | | 2022-09-20 | READ |
| 134 | RYAN | ssss77 | LEEDOOLY | | 2022-09-20 | READ |
| 133 | AHNOONG | roh123 | yb | | 2022-09-20 | UNREAD |
| 132 | SEODONGSIM | SI02002 | ESL | | 2022-09-20 | READ |

FIG. 4U

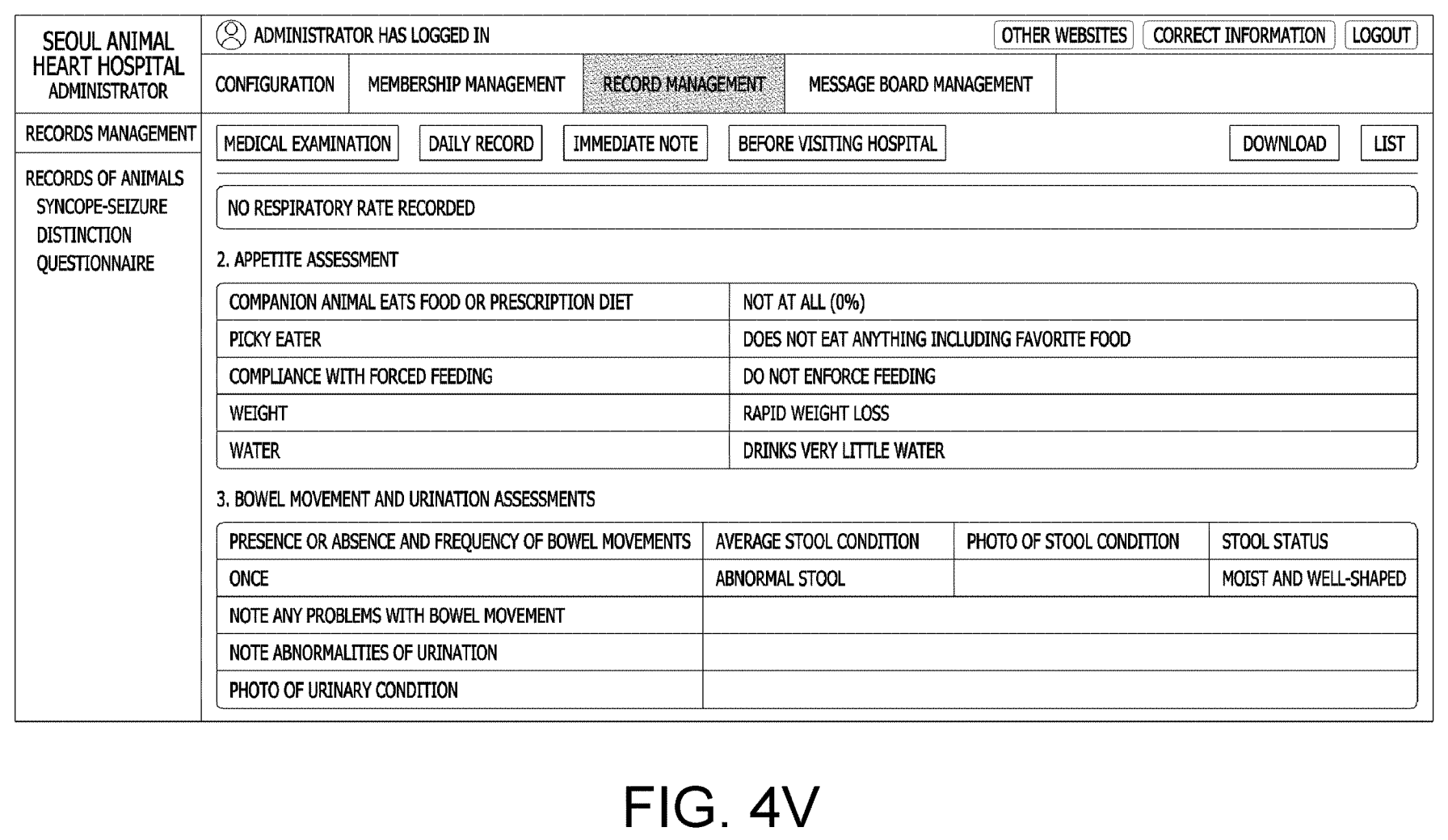

SEOUL ANIMAL HEART HOSPITAL
ADMINISTRATOR

ADMINISTRATOR HAS LOGGED IN

OTHER WEBSITES | CORRECT INFORMATION | LOGOUT

CONFIGURATION | MEMBERSHIP MANAGEMENT | RECORD MANAGEMENT | MESSAGE BOARD MANAGEMENT

RECORDS MANAGEMENT

RECORDS OF ANIMALS
SYNCOPE-SEIZURE DISTINCTION QUESTIONNAIRE

MEDICAL EXAMINATION | DAILY RECORD | IMMEDIATE NOTE | BEFORE VISITING HOSPITAL | DOWNLOAD | LIST

NO RESPIRATORY RATE RECORDED

2. APPETITE ASSESSMENT

| | |
|---|---|
| COMPANION ANIMAL EATS FOOD OR PRESCRIPTION DIET | NOT AT ALL (0%) |
| PICKY EATER | DOES NOT EAT ANYTHING INCLUDING FAVORITE FOOD |
| COMPLIANCE WITH FORCED FEEDING | DO NOT ENFORCE FEEDING |
| WEIGHT | RAPID WEIGHT LOSS |
| WATER | DRINKS VERY LITTLE WATER |

3. BOWEL MOVEMENT AND URINATION ASSESSMENTS

| PRESENCE OR ABSENCE AND FREQUENCY OF BOWEL MOVEMENTS | AVERAGE STOOL CONDITION | PHOTO OF STOOL CONDITION | STOOL STATUS |
|---|---|---|---|
| ONCE | ABNORMAL STOOL | | MOIST AND WELL-SHAPED |
| NOTE ANY PROBLEMS WITH BOWEL MOVEMENT | | | |
| NOTE ABNORMALITIES OF URINATION | | | |
| PHOTO OF URINARY CONDITION | | | |

FIG. 4V

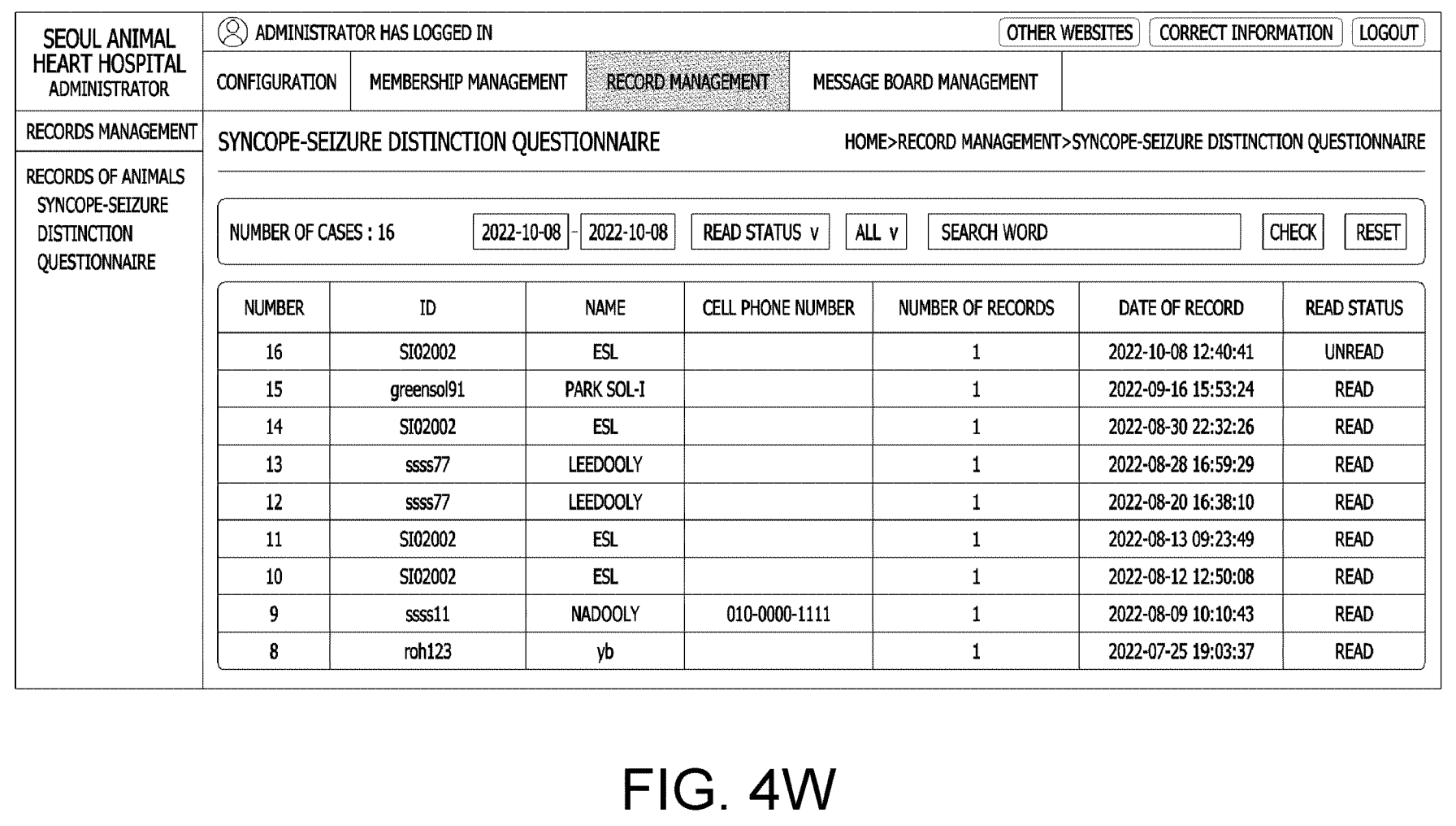

SEOUL ANIMAL HEART HOSPITAL
ADMINISTRATOR

ADMINISTRATOR HAS LOGGED IN

OTHER WEBSITES | CORRECT INFORMATION | LOGOUT

CONFIGURATION | MEMBERSHIP MANAGEMENT | RECORD MANAGEMENT | MESSAGE BOARD MANAGEMENT

RECORDS MANAGEMENT

RECORDS OF ANIMALS
SYNCOPE-SEIZURE DISTINCTION QUESTIONNAIRE

SYNCOPE-SEIZURE DISTINCTION QUESTIONNAIRE

HOME>RECORD MANAGEMENT>SYNCOPE-SEIZURE DISTINCTION QUESTIONNAIRE

NUMBER OF CASES : 16 | 2022-10-08 - 2022-10-08 | READ STATUS v | ALL v | SEARCH WORD | CHECK | RESET

| NUMBER | ID | NAME | CELL PHONE NUMBER | NUMBER OF RECORDS | DATE OF RECORD | READ STATUS |
|---|---|---|---|---|---|---|
| 16 | SI02002 | ESL | | 1 | 2022-10-08 12:40:41 | UNREAD |
| 15 | greensol91 | PARK SOL-I | | 1 | 2022-09-16 15:53:24 | READ |
| 14 | SI02002 | ESL | | 1 | 2022-08-30 22:32:26 | READ |
| 13 | ssss77 | LEEDOOLY | | 1 | 2022-08-28 16:59:29 | READ |
| 12 | ssss77 | LEEDOOLY | | 1 | 2022-08-20 16:38:10 | READ |
| 11 | SI02002 | ESL | | 1 | 2022-08-13 09:23:49 | READ |
| 10 | SI02002 | ESL | | 1 | 2022-08-12 12:50:08 | READ |
| 9 | ssss11 | NADOOLY | 010-0000-1111 | 1 | 2022-08-09 10:10:43 | READ |
| 8 | roh123 | yb | | 1 | 2022-07-25 19:03:37 | READ |

FIG. 4W

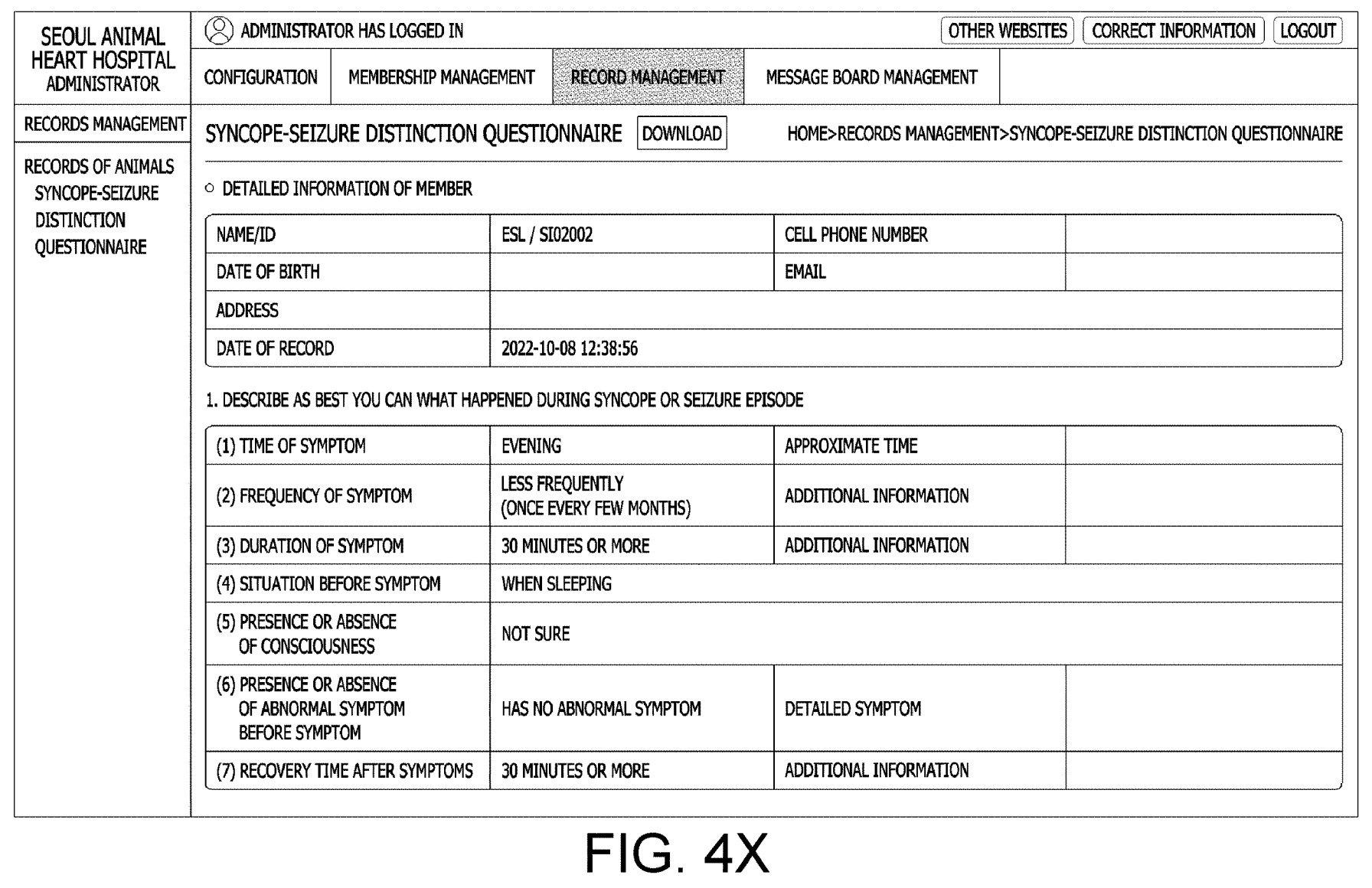

SEOUL ANIMAL HEART HOSPITAL ADMINISTRATOR

ADMINISTRATOR HAS LOGGED IN

OTHER WEBSITES | CORRECT INFORMATION | LOGOUT

CONFIGURATION | MEMBERSHIP MANAGEMENT | RECORD MANAGEMENT | MESSAGE BOARD MANAGEMENT

RECORDS MANAGEMENT

RECORDS OF ANIMALS
SYNCOPE-SEIZURE DISTINCTION QUESTIONNAIRE

SYNCOPE-SEIZURE DISTINCTION QUESTIONNAIRE DOWNLOAD

HOME>RECORDS MANAGEMENT>SYNCOPE-SEIZURE DISTINCTION QUESTIONNAIRE

○ DETAILED INFORMATION OF MEMBER

| NAME/ID | ESL / SI02002 | CELL PHONE NUMBER | |
|---|---|---|---|
| DATE OF BIRTH | | EMAIL | |
| ADDRESS | | | |
| DATE OF RECORD | 2022-10-08 12:38:56 | | |

1. DESCRIBE AS BEST YOU CAN WHAT HAPPENED DURING SYNCOPE OR SEIZURE EPISODE

| (1) TIME OF SYMPTOM | EVENING | APPROXIMATE TIME | |
|---|---|---|---|
| (2) FREQUENCY OF SYMPTOM | LESS FREQUENTLY (ONCE EVERY FEW MONTHS) | ADDITIONAL INFORMATION | |
| (3) DURATION OF SYMPTOM | 30 MINUTES OR MORE | ADDITIONAL INFORMATION | |
| (4) SITUATION BEFORE SYMPTOM | WHEN SLEEPING | | |
| (5) PRESENCE OR ABSENCE OF CONSCIOUSNESS | NOT SURE | | |
| (6) PRESENCE OR ABSENCE OF ABNORMAL SYMPTOM BEFORE SYMPTOM | HAS NO ABNORMAL SYMPTOM | DETAILED SYMPTOM | |
| (7) RECOVERY TIME AFTER SYMPTOMS | 30 MINUTES OR MORE | ADDITIONAL INFORMATION | |

FIG. 4X

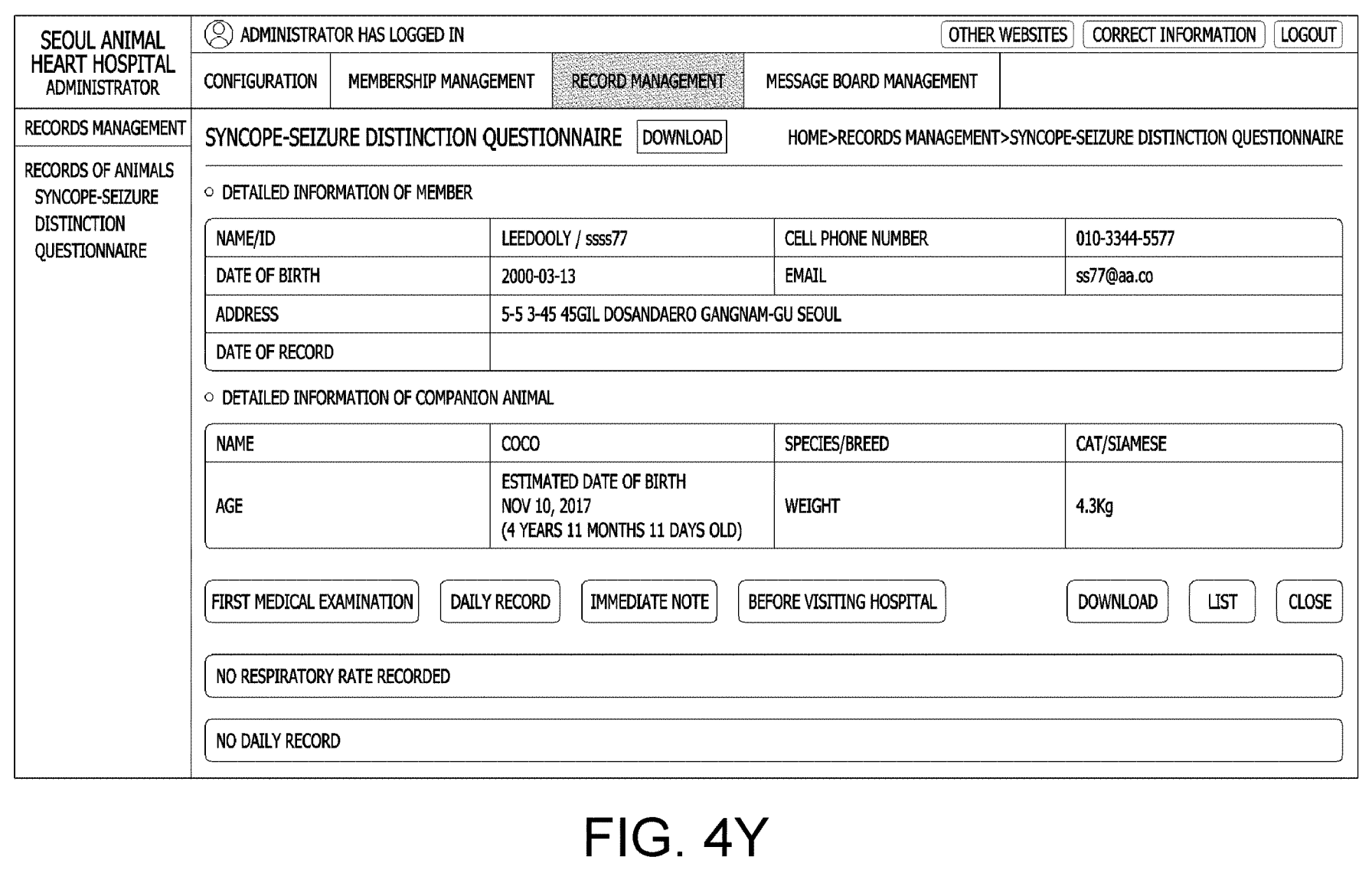

| NAME/ID | LEEDOOLY / ssss77 | CELL PHONE NUMBER | 010-3344-5577 |
|---|---|---|---|
| DATE OF BIRTH | 2000-03-13 | EMAIL | ss77@aa.co |
| ADDRESS | 5-5 3-45 45GIL DOSANDAERO GANGNAM-GU SEOUL | | |
| DATE OF RECORD | | | |

| NAME | COCO | SPECIES/BREED | CAT/SIAMESE |
|---|---|---|---|
| AGE | ESTIMATED DATE OF BIRTH NOV 10, 2017 (4 YEARS 11 MONTHS 11 DAYS OLD) | WEIGHT | 4.3Kg |

FIG. 4Y

| | A | B |
|---|---|---|
| 13 | 111 | |
| 14 | | |
| 15 | 4. PRECAUTIONS DURING DIAGNOSTIC TEST<br>- THINGS TO PAY SPECIAL ATTENTION TO WHEN TREATING PATIENT | |
| 16 | YES | 222 |
| 17 | | |
| 18 | 5. DRUGS CURRENTLY BEING TAKEN | |
| 19 | 1) HEART MEDICINE | YES |
| 20 | 2) DRUGS OTHER THAN HEART MEDICINE | YES |
| 21 | 3) ADDITIONAL INFORMATION ABOUT DRUGS CURRENTLY BEING TAKEN | YES |
| 22 | | |
| 23 | 6. SUPPLEMENTS CURRENTLY BEING TAKEN | |
| 24 | 1) HEART MEDICINE | YES |
| 25 | 2) YOUR COMPANION ANIMAL'S UNDERLYING DISEASE (DISEASE BEING TREATED OTHER THAN HEART DISEASE) | UNDERLYING DISEASE 1 |
| 26 | | |
| 27 | | |

FIG. 4Z

SYSTEM FOR PROVIDING MEDICAL RECORD SERVICE FOR ANIMAL WITH HEART DISEASE

CROSS-REFERENCE TO RELATED APPLICATION

This application claims the priority benefit of Korea application serial no. 10-2022-0141183, filed on Oct. 28, 2022. The entirety of the above-mentioned patent application is hereby incorporated by reference herein and made a part of this specification.

TECHNICAL FIELD

The present invention relates to a system for providing a medical record service for diagnosing a companion animal with a heart disease or internal disease, and more particularly, to a system for recording a health status of a companion animal with a heart disease or internal disease according to preset questions or a preset checklist.

BACKGROUND ART

The companion animal digital healthcare industry is expected to continuously grow in the future due to not only the increase of companion animals caused by the increase in single households and the spread of social media but also adaptation to information and communications technology (ICT). Unlike in the past when a guardian would take a companion animal to a veterinary hospital in person to give the companion animal a medical checkup and treatment, devices for checking health status on the basis of a wearable system, a remote monitoring system, or even artificial intelligence (AI) are being commercialized, and demand for such devices is also increasing. However, it is impossible to diagnose a companion animal with a disease through a diagnostic kit or healthcare device, and in the case of a non-face-to-face service, any treatment beyond simple consultation is not permitted under the current veterinary act. Therefore, various services based on non-face-to-face treatment are failing in commercialization each time, and even companies that provide services only in the United States due to Korean regulations are emerging.

A method of automatically measuring a companion animal's pulse rate or abnormal behavior and providing emergency medical information on the basis of the pulse rate has been researched and developed. In this regard, Korean Patent Application Publication Nos. 2020-0063637 (published on Jun. 5, 2020) and 2022-0026644 (published on Mar. 7, 2022) disclose a configuration in which a user terminal measures a companion animal's pulse rate through a wearable device, transmits the pulse rate to a veterinary hospital, and then receives an analysis result from a veterinary hospital terminal and a configuration in which a wearable device collects health status information of a companion animal, determines whether the companion animal is abnormal, and generates and transmits emergency medical information to a user terminal when the companion animal is determined to be abnormal, respectively.

Here, both are only configurations for checking a companion animal's health on the basis of its pulse rate and providing an analysis result, and it is not possible to rule out the possibility of misdiagnosis of a diagnostic result based on data which is collected without various face-to-face tests and the possibility of errors in diagnosis based on AI judgment. Also, the foregoing configurations are only for finding a disease or abnormality and are not for monitoring a disease which has already been diagnosed. Companion animals with a heart disease or internal disease have many symptoms, such as cough, difficulty breathing, cyanosis, ascites, pleural effusion, weight loss, fainting, syncope, seizures, hindlimb paralysis, and the like that need to be managed and monitored every day. Outside of regular checkups, it is not possible to regularly check and monitor the companion animals, and due to the nature of heart medicine that requires lifelong use once a companion animal takes it, it is not possible to admit the companion animals to a veterinary hospital and monitor the progress of the diseases until the companion animals die. Therefore, it is necessary to research and develop a platform for registering companion animals with a heart disease or internal disease and recording sleeping respiratory rates (SRRs), health statuses, syncope, or seizures of the companion animals.

SUMMARY

Technical Problem

The present invention is directed to providing a system for providing a medical record service for diagnosing a companion animal with a heart disease or internal disease that allows a user terminal to register a companion animal with a heart disease or internal disease and record the companion animal's sleeping respiratory rate (SRR), health status, syncope, or seizures, provides a messenger-type note function for writing a note in real time in an emergency situation, allows the user terminal to record appetite, weight, drinking volume, bowel movement and urination assessments, a weight assessment, cough monitoring, and a vomiting assessment in a health status, allows the user terminal to check and consistently record various symptoms, such as the frequency, times, and durations of syncope or seizures caused by the heart disease, presence or absence of aura symptoms, presence or absence of consciousness at onset, presence or absence of cyanosis, distinction between syncope and seizures, presence or absence of eye movements, and the like, and allows a veterinary hospital terminal to monitor the companion animal and determine whether the companion animal is required to visit the veterinary hospital while checking the records written through the user terminal. However, technical objectives of the present invention are not limited to those described above, and there may be other technical objectives.

Technical Solution

According to an aspect of the present invention, there is provided a server for providing a medical record service for diagnosing a companion animal with a heart disease or internal disease, the server including a user terminal configured to register a companion animal and then answer at least one question and a checklist for noting an abnormality, measuring an SRR, recording a status, and recording syncope and seizures, a veterinary hospital terminal configured to output records written through the user terminal, and a medical record service providing server including a basic information part configured to allow the user terminal to record basic information of the companion animal when the user terminal registers the companion animal, an abnormality note part configured to display and store the abnormality note and a time in a messenger form when the abnormality note is written through the user terminal, an SRR part configured to store time-series changes of the SRR in a log and visualize the time-series changes of the SRR as a graph when the user terminal measures the SRR, and a syncope-seizure distinction part configured to map questions and a checklist for syncope and seizures to a record and answers and store the record and answers mapped to the questions and checklist.

Effects of Invention

According to any one of the solutions described above, with a user terminal, it is possible to register a companion animal with a heart disease or internal disease, record the companion animal's SRR, health status, syncope, or seizures, provide a messenger-type note function for writing a note in real time in an emergency situation, record appetite, a weight, a drinking volume, bowel movement and urination assessments, a weight assessment, cough monitoring, and a vomiting assessment in the health status, check and consistently record various symptoms, such as a frequency, times, and durations of syncope or seizures caused by the heart disease, presence or absence of aura symptoms, presence or absence of consciousness at onset, presence or absence of cyanosis, distinction between syncope and seizures, presence or absence of eye movements, and the like, and with a veterinary hospital terminal, it is possible to monitor the companion animal and determine whether the companion animal is required to visit the veterinary hospital while checking in real time the records written through the user terminal.

DESCRIPTION OF THE EMBODIMENTS

Figure 1:
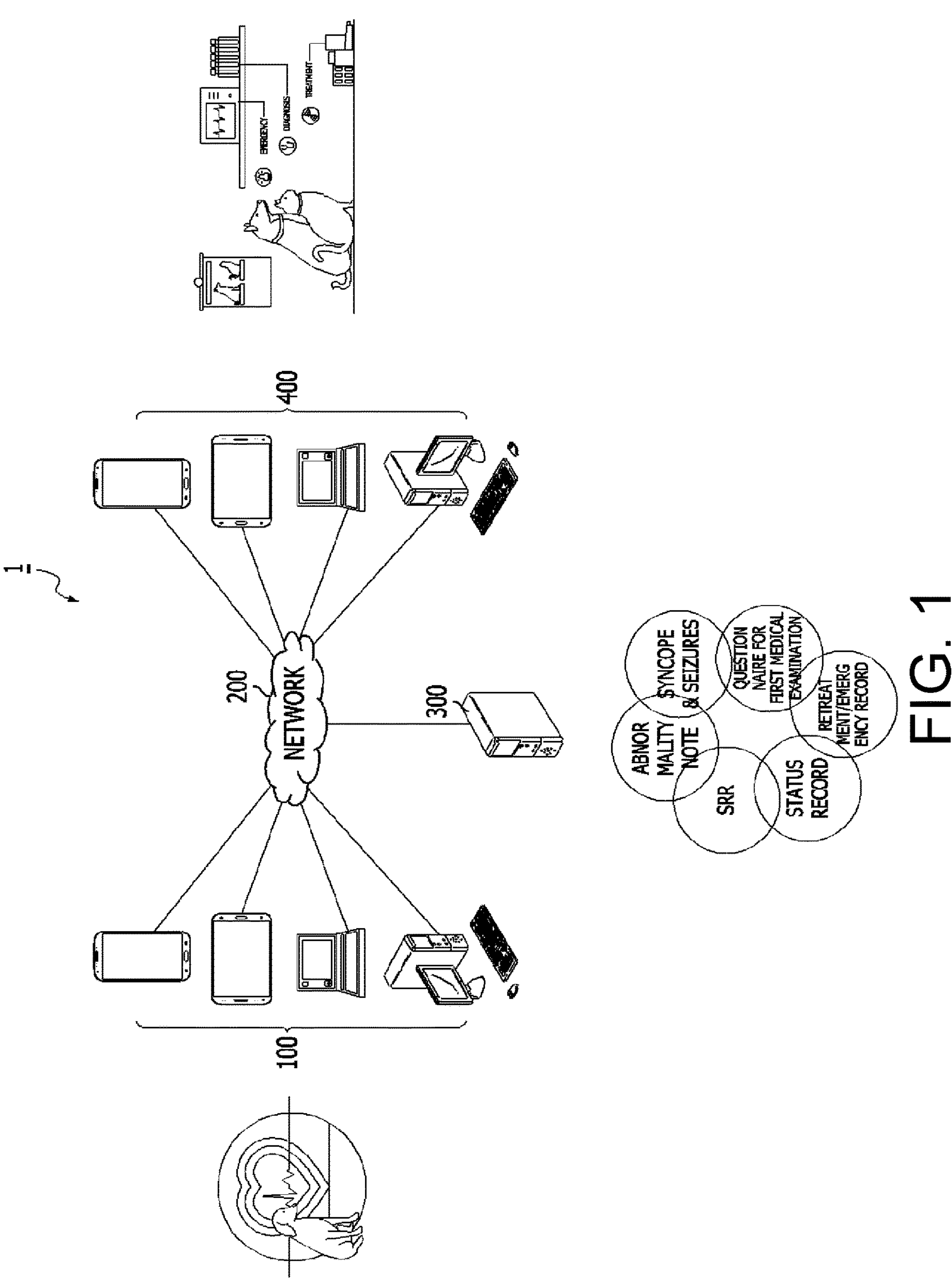
FIG. 1 is a diagram illustrating a system for providing a medical record service for diagnosing a companion animal with a heart disease or internal disease according to an exemplary embodiment of the present invention.

Hereinafter, exemplary embodiments of the present invention will be described in detail so that those of ordinary skill in the art can readily implement the present invention. However, the present invention can be implemented in several different forms and is not limited to the exemplary embodiments described below. To clearly describe the present invention, parts unrelated to description will be omitted in the drawings. Throughout the specification, like reference numerals refer to like elements.

In the specification, when an element is referred to as being "connected" to another element, the elements may be "directly connected" to each other or "electrically connected" to each other with an intervening element therebetween. Also, when a part is referred to as "including" a certain component, other components are not excluded but may be further included unless particularly stated otherwise. It is to be understood that the expression does not preclude the presence or addition of one or more other features, numbers, steps, operations, components, parts, or a combination thereof.

As used throughout the specification, the terms "about," "substantially," and the like are used to indicate a value or a nearby value when unique manufacturing and material tolerances are presented for a described meaning, and the terms are used to prevent unscrupulous infringers from unfairly using the disclosure including accurate or absolute figures for aiding in the understanding of the present invention. The term "step of (doing)" or "step of" used throughout the specification of the present invention does not indicate "step for."

In the specification, a "part" includes a unit implemented by hardware, a unit implemented by software, and a unit implemented using both. In addition, one part may be implemented using two or more pieces of hardware, and two or more parts may be implemented using one piece of hardware. Meanwhile, the meaning of "part" is not limited to software or hardware, and a "part" may be configured to be present in an addressable storage medium or run one or more processors. Therefore, as examples, a "part" includes components such as software components, object-oriented software components, class components, and task components, processes, functions, attributes, procedures, subroutines, segments of program code, drivers, firmware, microcode, a circuit, data, a database, data structures, tables, arrays, and variables. Functions provided in components and "parts" may be combined into a smaller number of components and "parts" or may be subdivided into additional components and "parts." Further, components and "parts" may be implemented to run one or more central processing units (CPUs) in a device or security multimedia card.

In the specification, some operations or functions described as being performed by a terminal, an apparatus, or a device may be performed by a server connected to the terminal, the apparatus, or the device instead. Likewise, some operations or functions described as being performed by a server may be performed by a terminal, an apparatus, or a device connected to the server.

In the specification, some operations or functions described as "mapping" or "matching" a terminal may be construed as "mapping" or "matching" a unique number of the terminal or personal identification information which is identifying data of the terminal.

The present invention will be described in detail below with reference to the accompanying drawings.

FIG. 1 is a diagram illustrating a system for providing a medical record service for diagnosing a companion animal with a heart disease or internal disease according to an exemplary embodiment of the present invention. Referring to FIG. 1, a system 1 for providing a medical record service for diagnosing a companion animal with a heart disease or internal disease may include at least one user terminal 100, a medical record service providing server 300, and at least one veterinary hospital terminal 400. However, the system 1 for providing a medical record service for diagnosing a companion animal with a heart disease or internal disease shown in FIG. 1 is merely an exemplary embodiment, and the present invention is not limited to FIG. 1.

The components of FIG. 1 are generally connected through a network 200. For example, as shown in FIG. 1, the at least one user terminal 100 may be connected to the medical record service providing server 300 through the network 200. The medical record service providing server 300 may be connected to the at least one user terminal 100 and the at least one veterinary hospital terminal 400 through the network 200. Also, the at least one veterinary hospital terminal 400 may be connected to the medical record service providing server 300 through the network 200.

The network is a communication structure in which nodes, such as a plurality of terminals and servers, may exchange information. Examples of the network include a local area network (LAN), a wide area network (WAN), the Internet (World Wide Web (WWW)), a wired or wireless data communication network, a public switched telephone network (PSTN), a wired or wireless television (TV) communication network, and the like. Examples of a wireless data communication network include, but are not limited to, a third generation (3G) network, a fourth generation (4G) network, a fifth generation (5G) network, a Third Generation Partnership Project (3GPP) network, a Fifth Generation Partnership Project (5GPP) network, a Long Term Evolution (LTE) network, a World Interoperability for Microwave Access (WiMAX) network, Wi-Fi, the Internet, a LAN, a wireless LAN, a WAN, a personal area network (PAN), a radio frequency (RF) network, a Bluetooth network, a near-field communication (NFC) network, a satellite broadcasting network, an analog broadcasting network, a digital multimedia broadcasting network, and the like.

The phrase "at least one" is defined to include the singular and the plural. Even when the phrase "at least one" is not used, each component may be singular or plural in number and may represent the singular or plural. Each component may be provided as a single component or a plurality of components depending on embodiments.

The at least one user terminal 100 may be a guardian's terminal for registering a companion animal using a webpage, an app page, a program, or an application related to the medical record service for diagnosing a companion animal with a heart disease or internal disease and inputting an answer to at least one question or checklist.

Here, the at least one user terminal 100 may be implemented as a computer that may access a server or terminal at a remote place through a network. The computer may be, for example, a navigation device, a notebook computer, a desktop computer, or a laptop computer, or the like on which a web browser is installed. The at least one user terminal 100 may be implemented as a terminal that may access a server or terminal at a remote place through a network. The at least one user terminal 100 is, for example, a wireless communication device with portability and mobility and may be any type of handheld wireless communication device such as a navigation device, a personal communication system (PCS) device, a Global System for Mobile Communication (GSM) device, a personal digital cellular (PDC) device, a personal handyphone system (PHS) device, a personal digital assistant (PDA) device, an International Mobile Telecommunication (IMT)-2000 device, a code division multiple access (CDMA)-2000 device, a wideband CDMA (W-CDMA) device, a wireless broadband Internet (WiBro) terminal, a smartphone, a smartpad, a tablet personal computer (PC), or the like.

The medical record service providing server 300 may be a server that provides the webpage, the app page, the program, or the application related to the medical record service for diagnosing a companion animal with a heart disease or internal disease. The medical record service providing server 300 may be a server that provides a menu for recording an abnormality note, a sleeping respiratory rate (SRR), a status, retreatment/emergency, a questionnaire for first medical examination, and syncope and seizures. Also, the medical record service providing server 300 may be a server that transmits data input through the user terminal 100 to the veterinary hospital terminal 400 of a veterinary hospital selected by a user.

The medical record service providing server 300 may be implemented as a computer that may access a server or terminal at a remote place through a network. Here, the computer may be, for example, a navigation device, a notebook computer, a desktop computer, or a laptop computer on which a web browser is installed, or the like.

The at least one veterinary hospital terminal 400 may be a veterinary hospital terminal for using the webpage, the app page, the program, or the application related to the medical record service for diagnosing a companion animal with a heart disease or internal disease. Also, the at least one veterinary hospital terminal 400 may be a terminal that outputs a response received from the user terminal 100 through the medical record service providing server 300 in real time.

The at least one veterinary hospital terminal 400 may be implemented as a computer that may access a server or terminal at a remote place through a network. Here, the computer may be, for example, a navigation device, a notebook computer, a desktop computer, or a laptop computer on which a web browser is installed, or the like. The at least one veterinary hospital terminal 400 may be implemented as a terminal that may access a server or terminal at a remote place through a network. The at least one veterinary hospital terminal 400 is, for example, a wireless communication device with portability and mobility and may be any type of handheld wireless communication device such as a navigation device, a PCS device, a GSM device, a PDC device, a PHS device, a PDA device, an IMT-2000 device, a CDMA-2000 device, a W-CDMA device, a WiBro terminal, a smartphone, a smartpad, a tablet PC, or the like.

Figure 2:
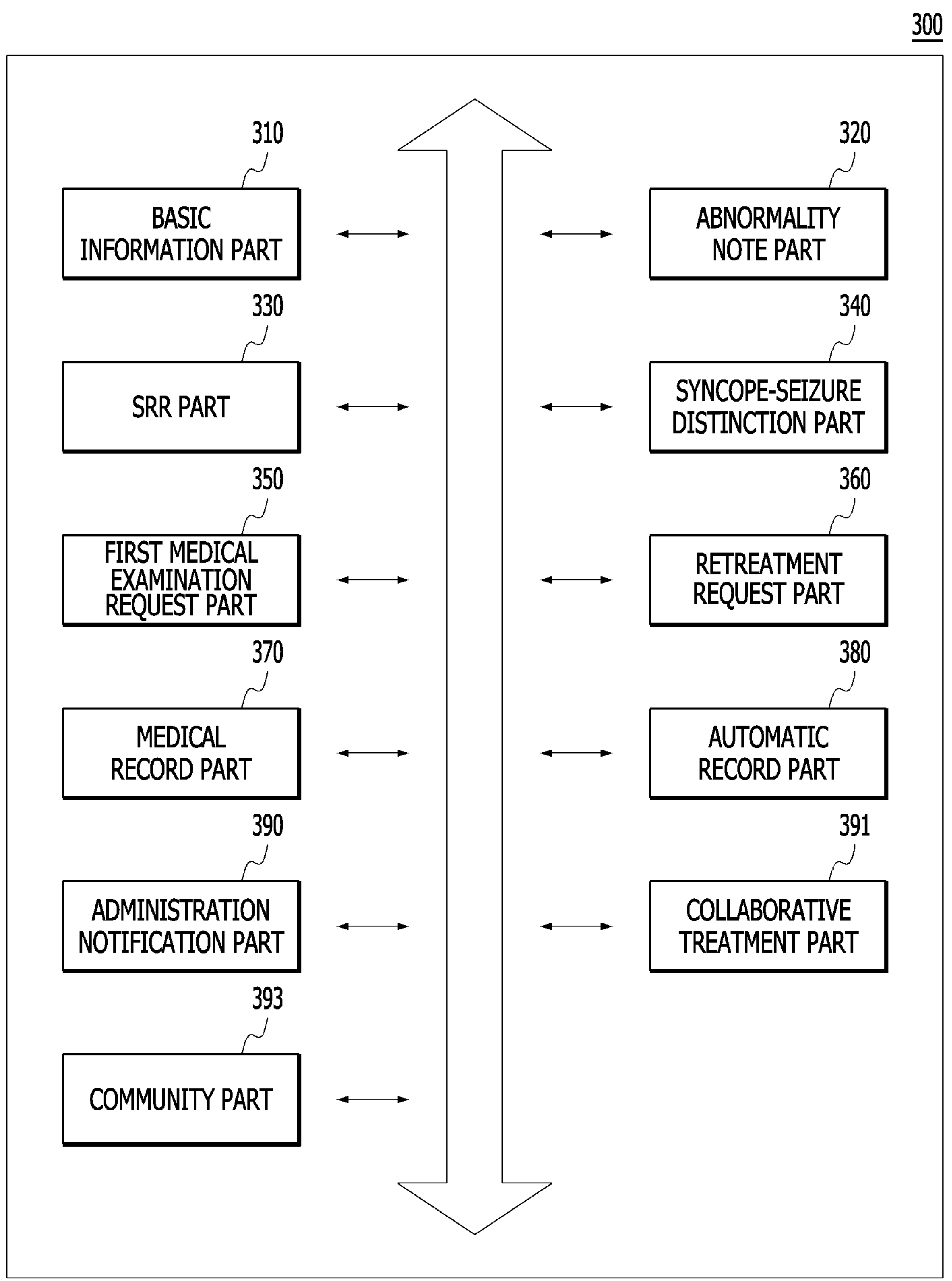
FIG. 2 is a block diagram illustrating a medical record service providing server included in the system of FIG. 1.
Figure 3A:
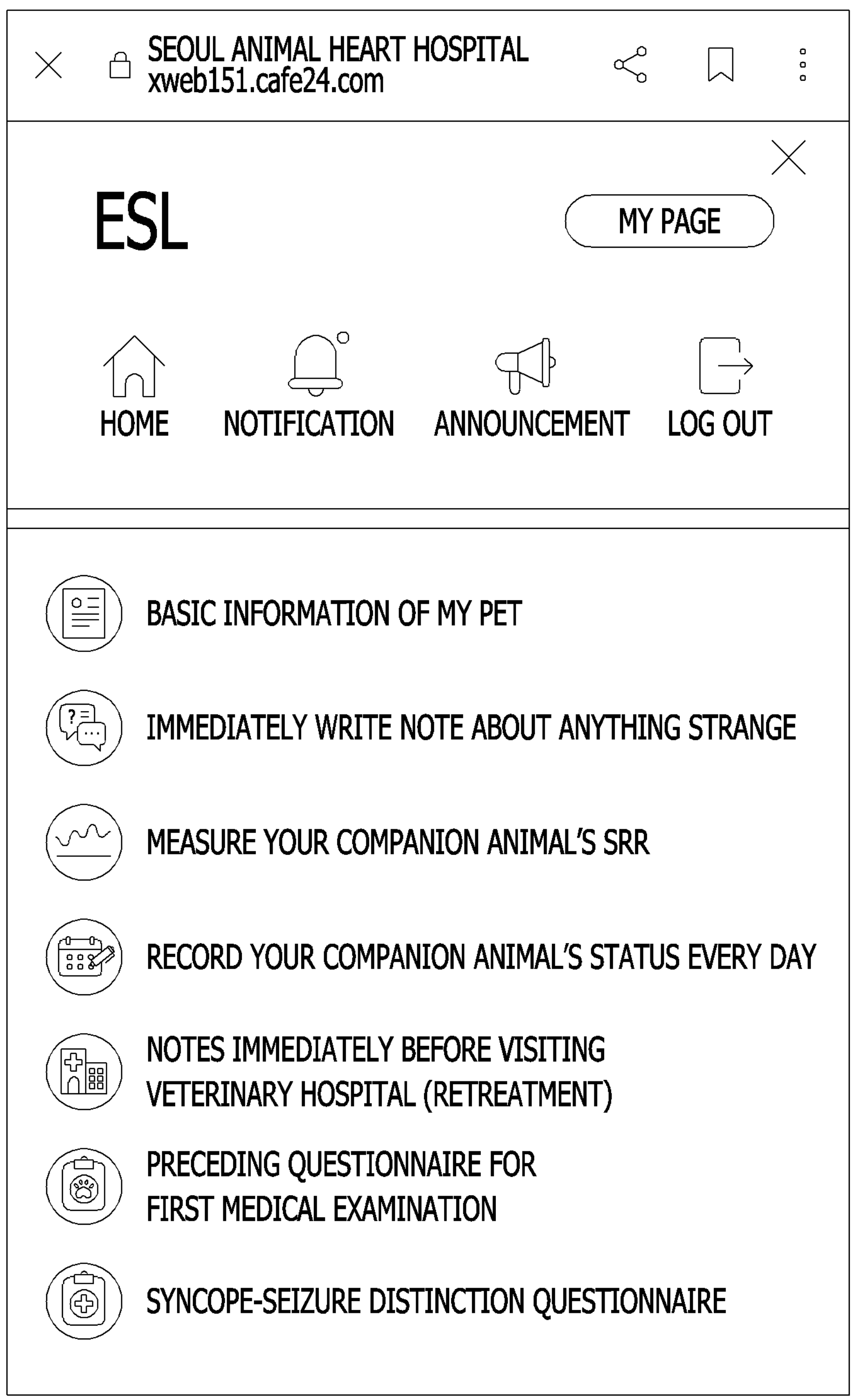
FIGS. 3A to 3Z and 4A to 4Z are diagrams illustrating an exemplary embodiment in which a medical record service for diagnosing a companion animal with a heart disease or internal disease according to an exemplary embodiment of the present invention is implemented.
Figure 3D:
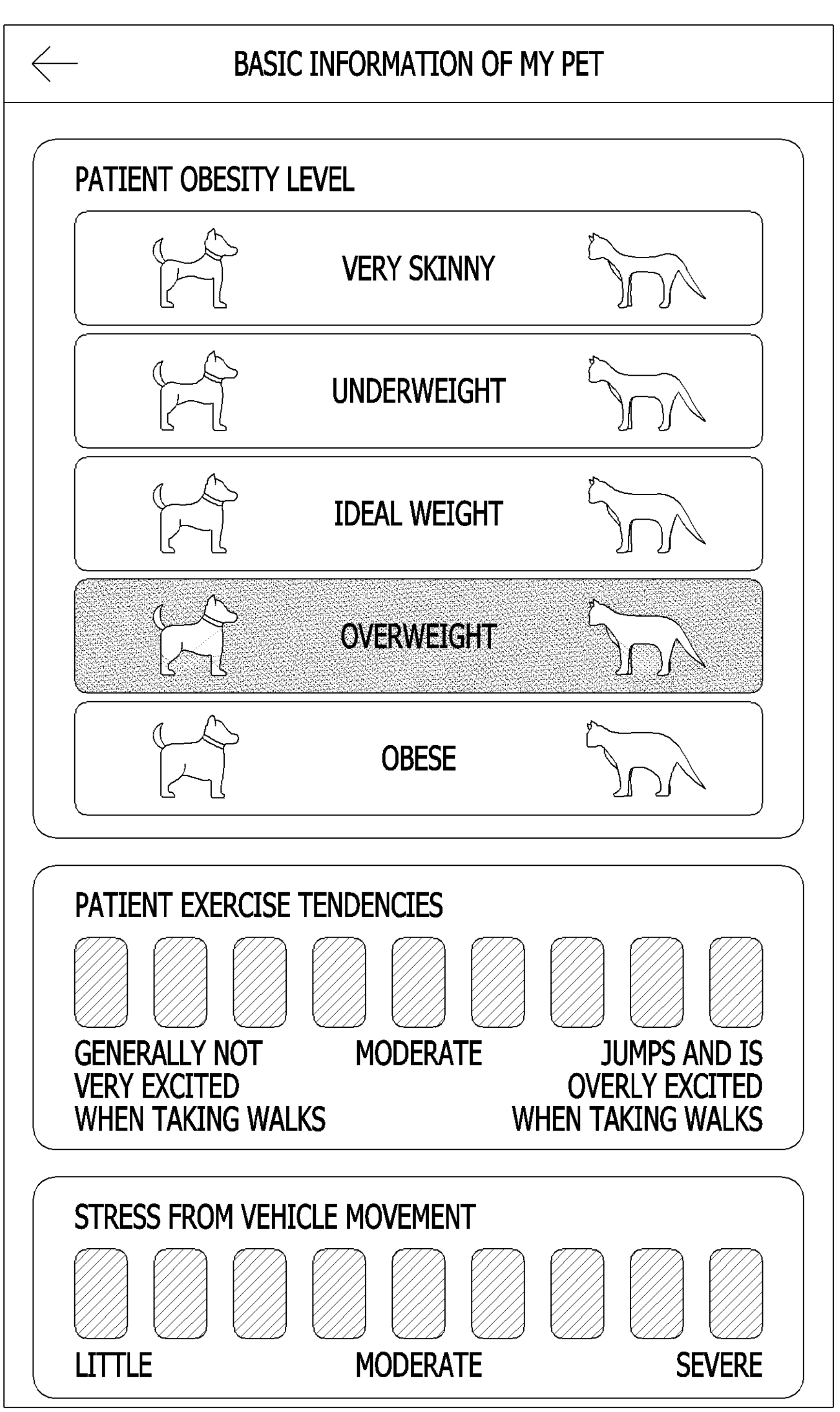
Figure 3E:
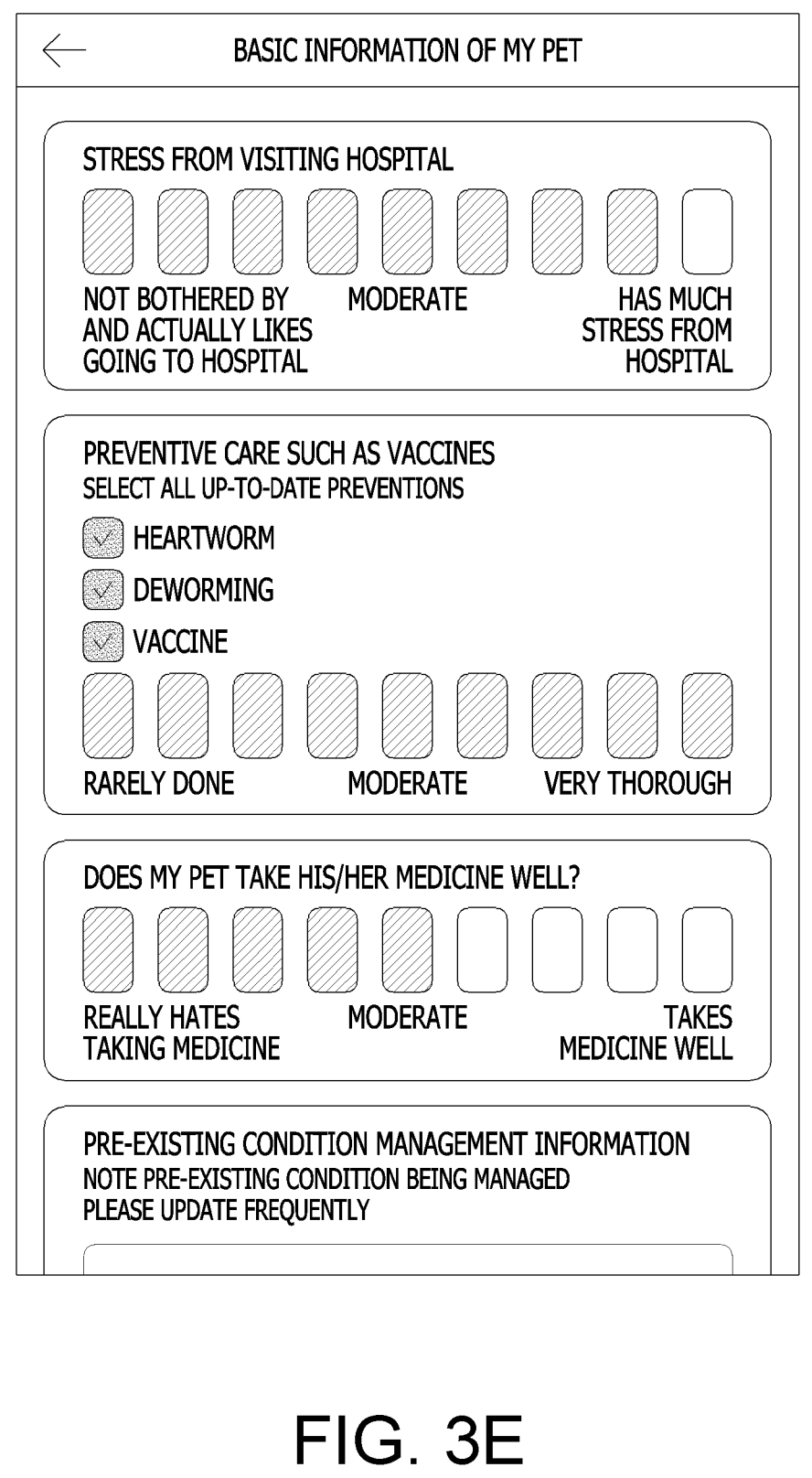
Figure 3G:
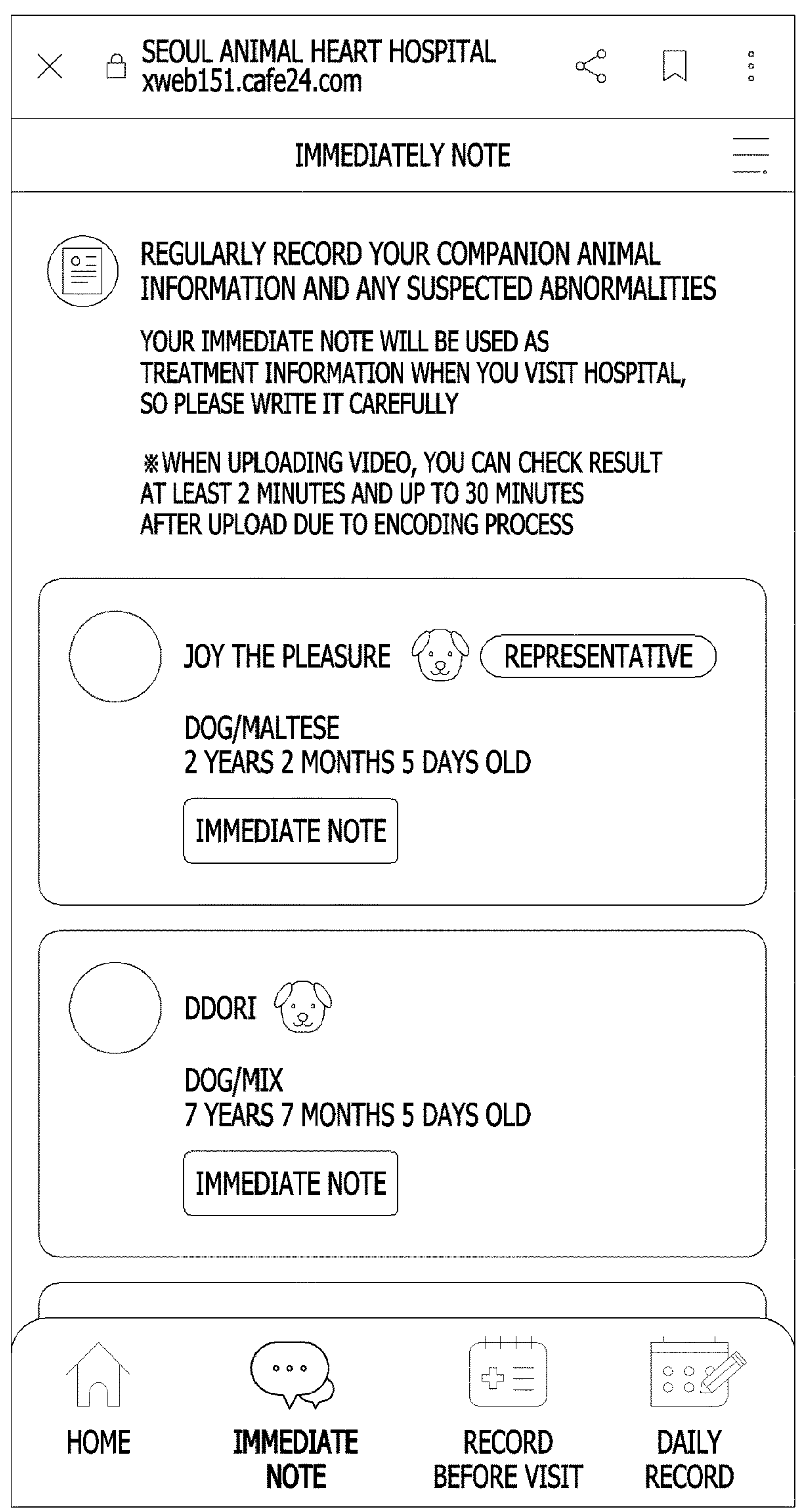
Figure 3H:
Figure 3I:
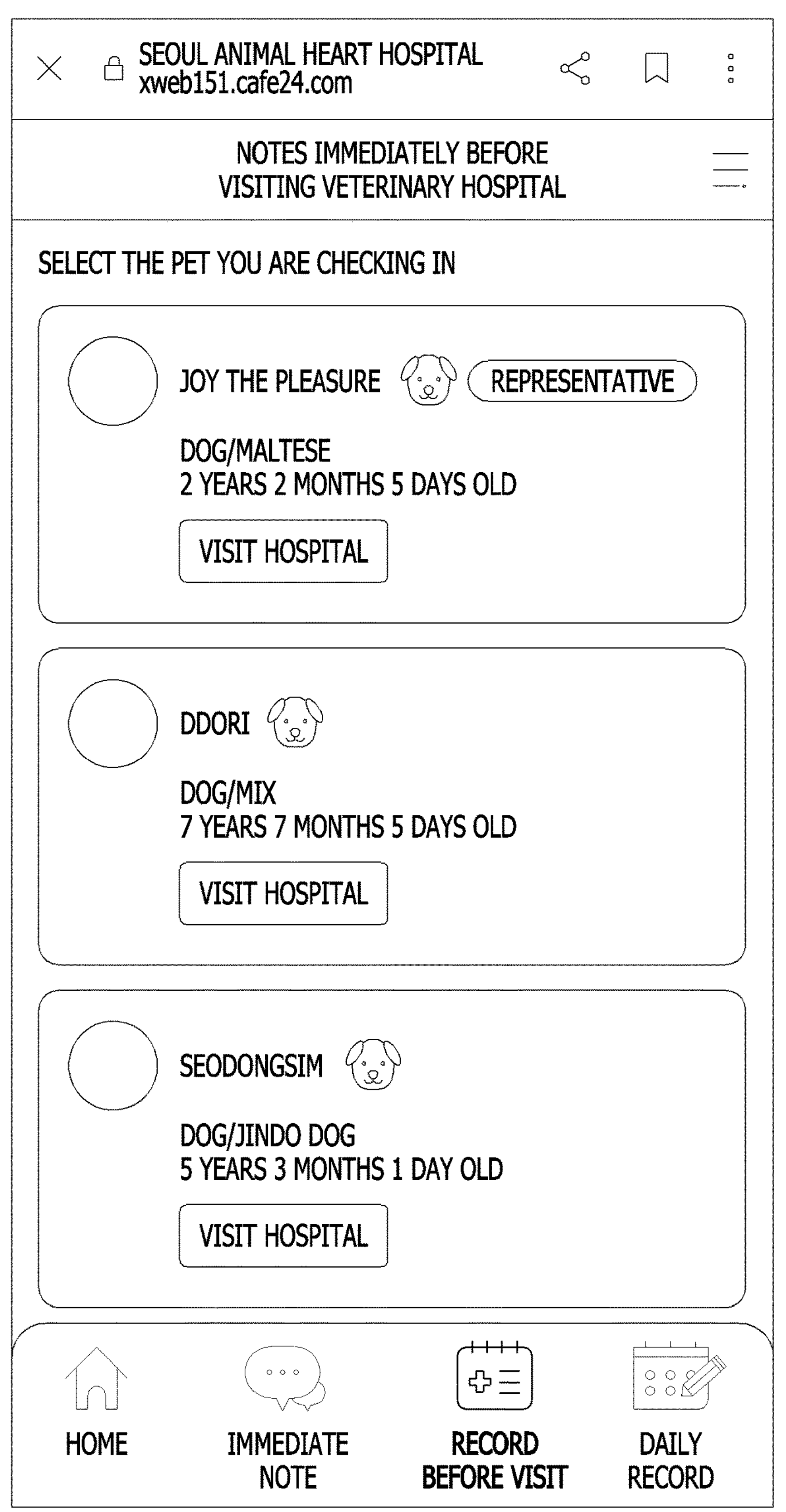
Figure 3K:
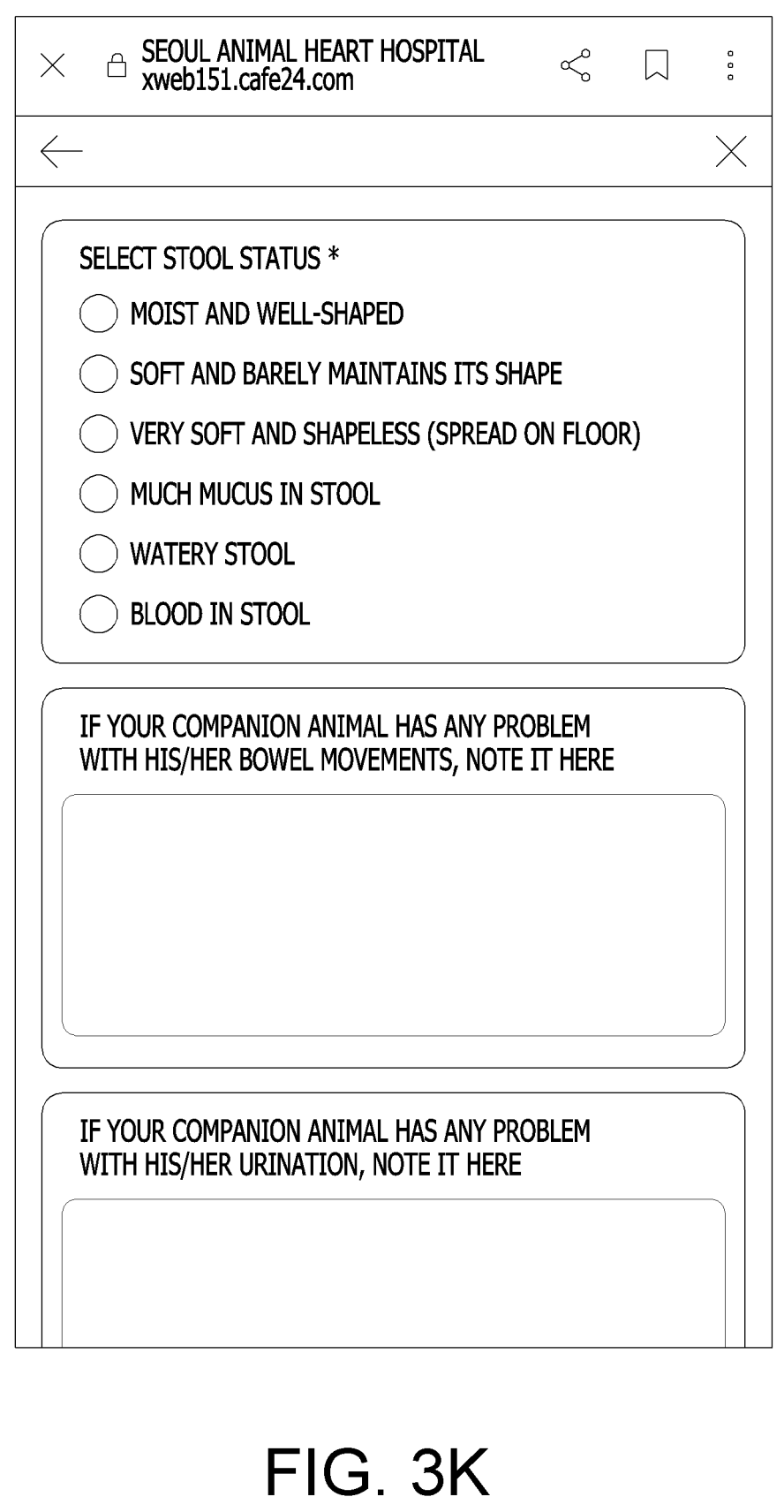
Figure 3L:
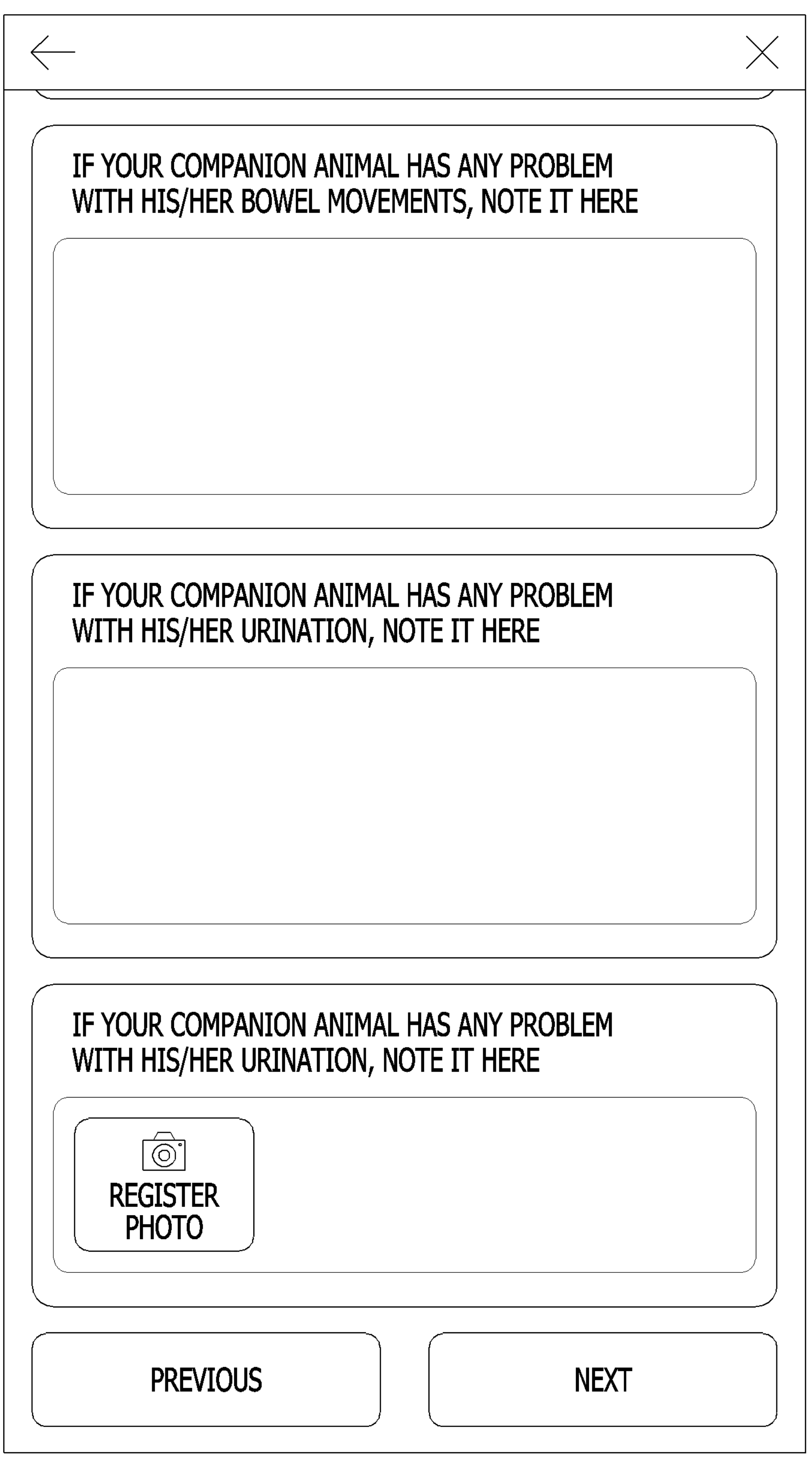
Figure 3Q:
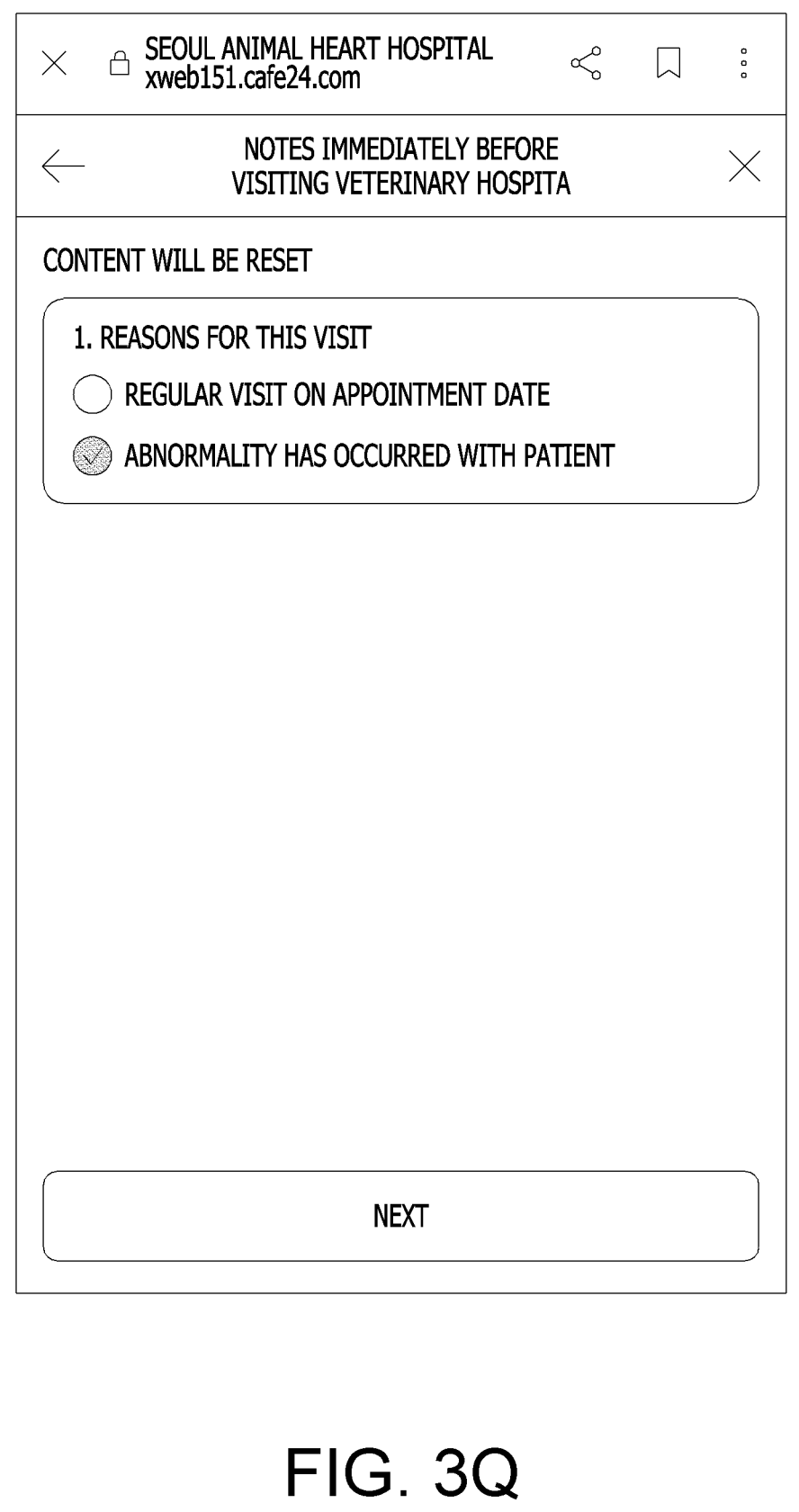
Figure 3R:
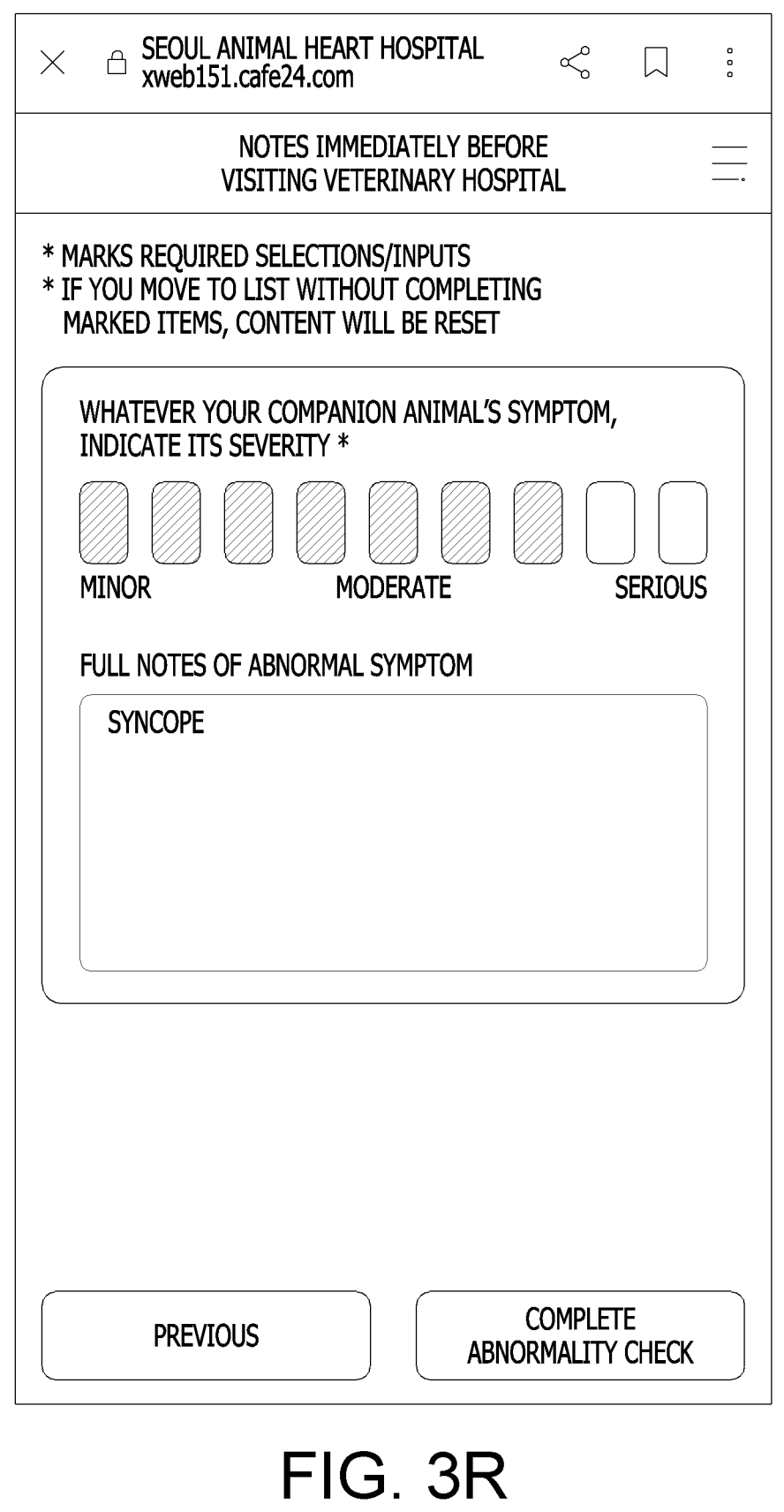
Figure 3S:
Figure 3T:
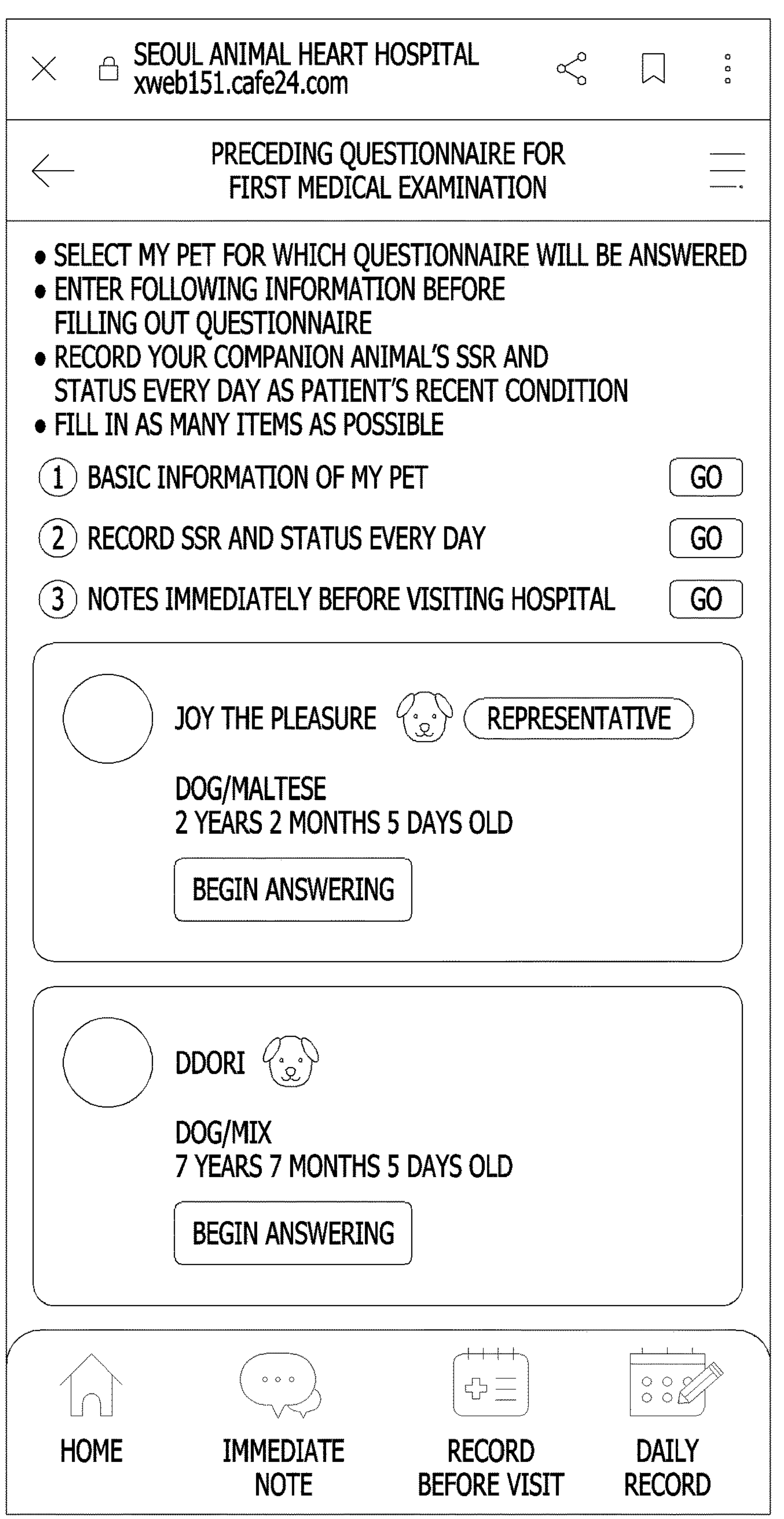
Figure 4A:
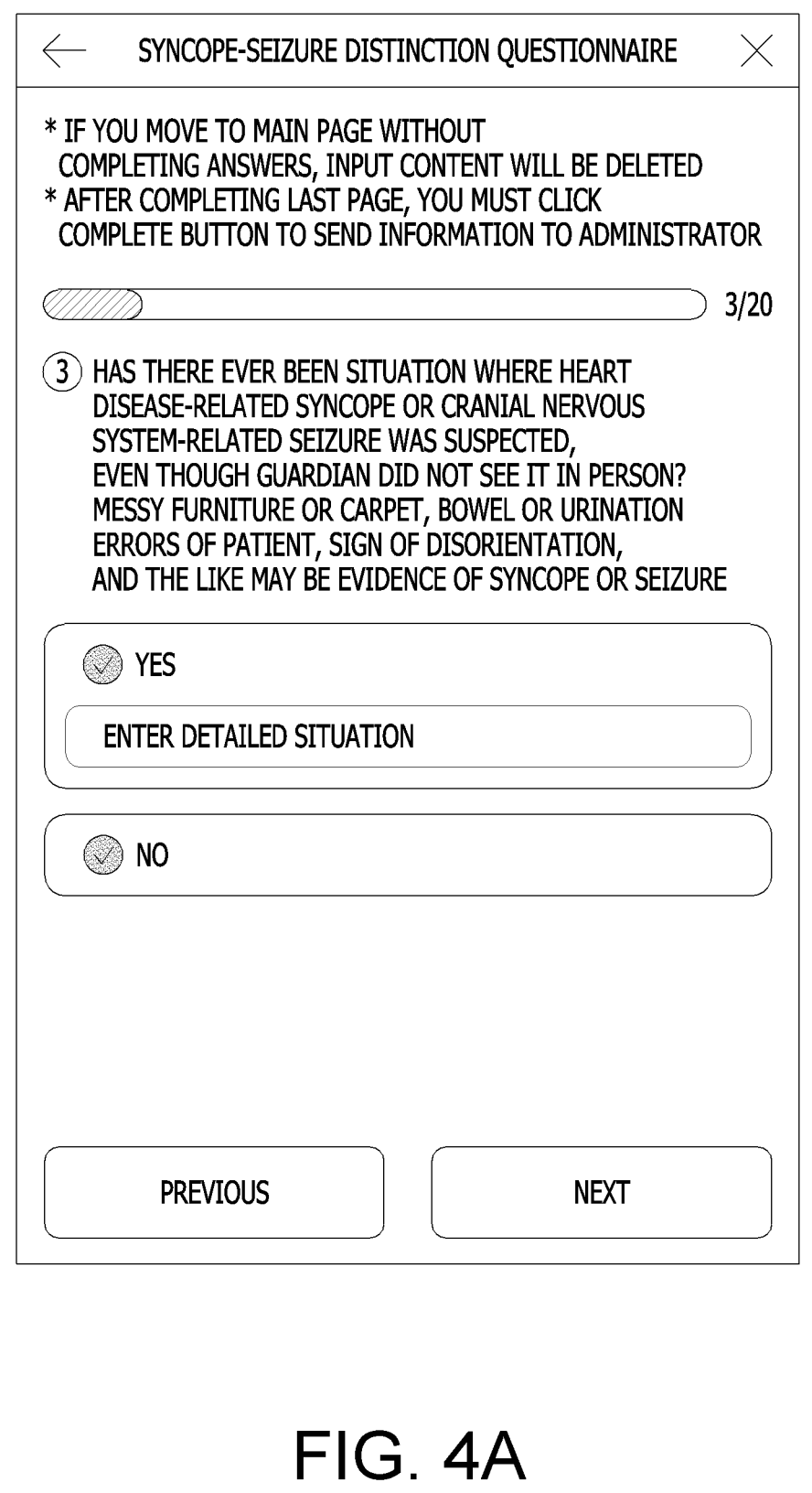
Figure 4G:
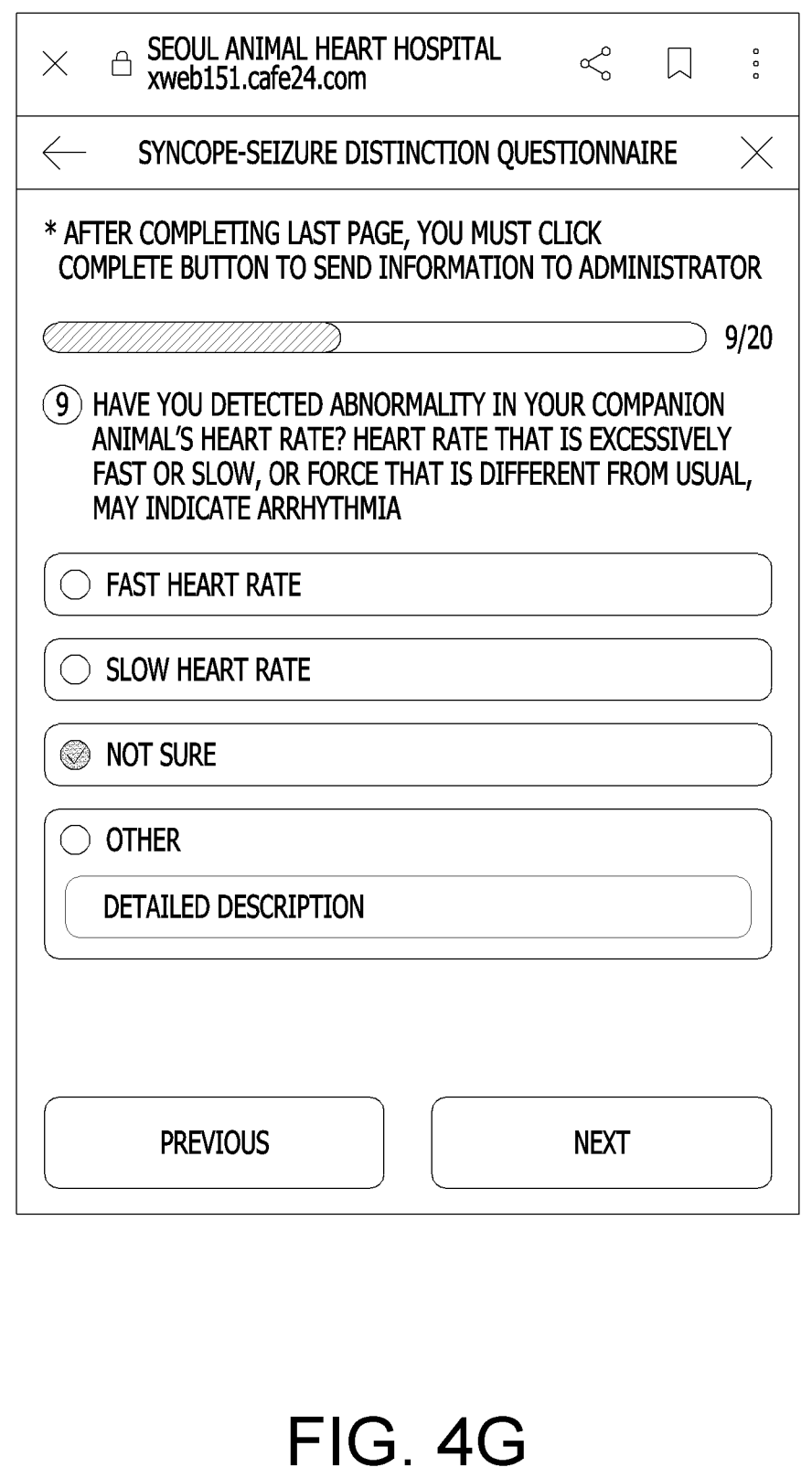
Figure 4L:
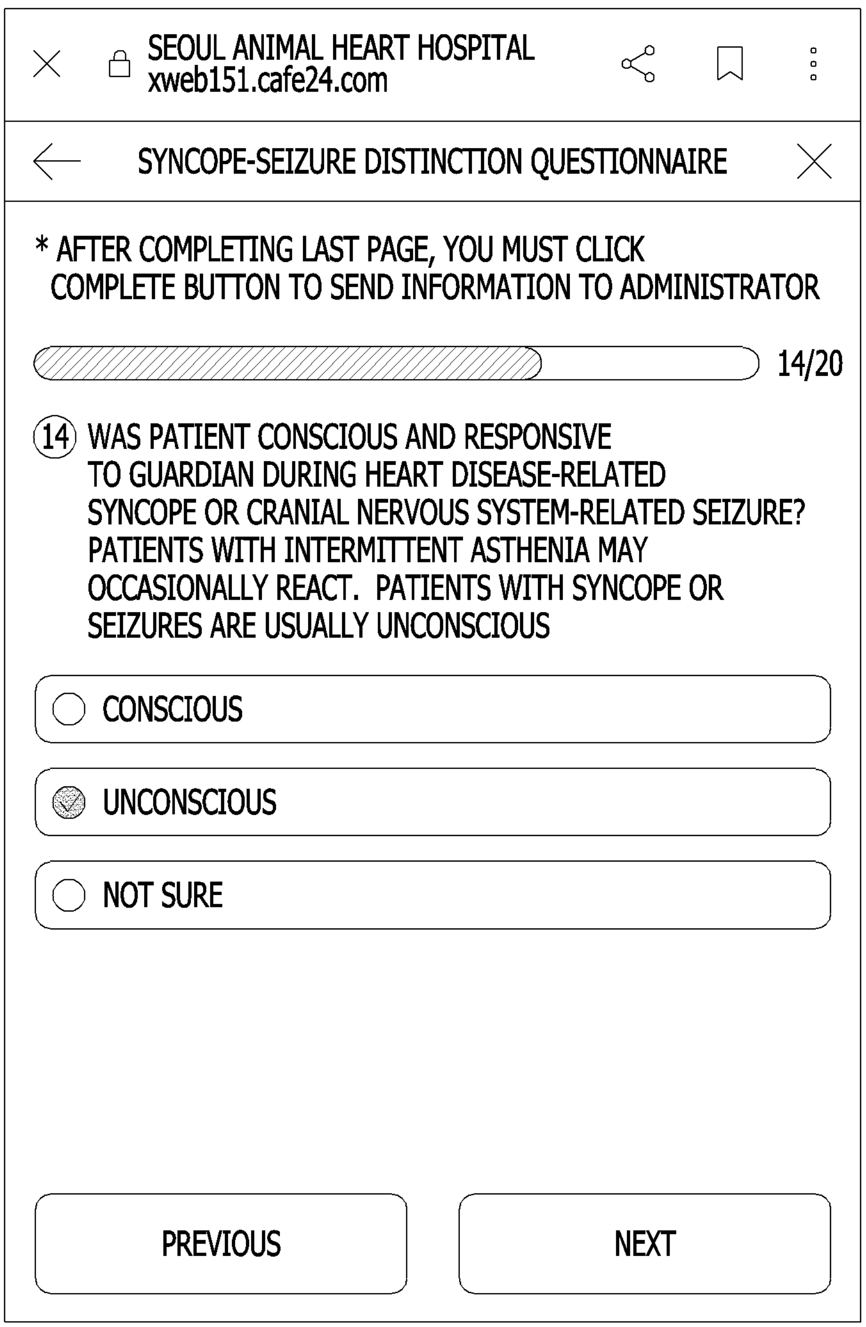

FIG. 2 is a block diagram illustrating a medical record service providing server included in the system of FIG. 1, and FIGS. 3 and 4 are diagrams illustrating an exemplary embodiment in which a medical record service for diagnosing a companion animal with a heart disease or internal disease according to an exemplary embodiment of the present invention is implemented.

Referring to FIG. 2, the medical record service providing server 300 may include a basic information part 310, an abnormality note part 320, an SRR part 330, a syncope-seizure distinction part 340, a first medical examination request part 350, a retreatment request part 360, a medical record part 370, an automatic record part 380, an administration notification part 390, a collaborative treatment part 391, and a community part 393.

When the medical record service providing server 300 according to the exemplary embodiment of the present invention or another server (not shown) interoperating therewith transmits the application, the program, the app page, the webpage, or the like related to the medical record service for diagnosing a companion animal with a heart disease or internal disease to the at least one user terminal 100 and the at least one veterinary hospital terminal 400, the at least one user terminal 100 and the at least one veterinary hospital terminal 400 may install or open the application, the program, the app page, the webpage, or the like related to the medical record service for diagnosing a companion animal with a heart disease or internal disease. Also, the service program may be run on the at least one user terminal 100 and the at least one veterinary hospital terminal 400 using a script executed on a web browser. Here, the web browser is a program that allows use of the web (WWW) service by receiving and displaying hypertext written in hypertext markup language (HTML). For example, the web browser is Netscape, Explorer, Chrome, or the like. Also, the application is an application program on a terminal. For example, the application is an app executed on a mobile terminal (smartphone).

A basic configuration of a platform according to an exemplary embodiment of the present invention may divide a basic medical status of a companion animal, which is observable and recordable by a guardian at home, into basic medical observation and special observation. Since it is difficult for the guardian to observe the companion animal in person, an intuitive user interface/user experience (UI/UX) is configured to easily record things to be observed by the guardian, that is, basic health items and special observation items according to a disease, such as a heart disease or the like, in the form of questions and answers, notes, photography, image uploading, and the like. The recorded companion animal data is directly transmitted to the platform of the present invention, and the transmitted data is accumulated by date as a history log and stored in a database and may also be output in the Excel format. Accordingly, a veterinarian can output the record and obtain information, which is observable at home, on the animal patient's basic health or progression of a special disease such as a heart disease.

The information is very helpful for the veterinarian in diagnosing the animal patient. People speak when they are sick, but most animals are unable to express their pain in the early or middle stages of diseases. In many cases where a guardian recognizes his or her companion animal's condition and brings it to a veterinary hospital, the companion animal is in the terminal stage in which it is difficult to do anything. Accordingly, a medical life record of an animal patient has a significant meaning. According to the personal information protection act, medical records of people are first-grade records, but those of animals are not. In terms of medicine, knowing as much as possible about an animal's basic life is very helpful for a veterinarian in monitoring health of the animal patient who is unable to speak and treating the animal patient. Therefore, the platform of the present invention receives basic information and disease information, cumulatively stores the received information, and allows access to a medical record history when an animal patient visits any veterinary hospital. Further, the present invention allows prediction of a disease and disorder based on big data and artificial intelligence (AI), and thus it is possible to construct a platform for detecting a disorder or disease in an early stage.

Referring to FIG. 2, when a companion animal is registered through the user terminal, the basic information part 310 may allow recording of basic information of the companion animal. The companion animal's species, age, adoption route, weight, defecation and urination, vaccination status, sex, neutering status, obesity level, exercise tendency, vehicle movement stress, hospital stress, medication stress, and existing disease management information may be input. Also, the user terminal 100 may be provided to further check additional disease information such as information on the circulatory system, the cranial nervous system, the musculoskeletal system, a skin disease, the digestive system, the hepatobiliary system, and the like.

When an abnormality note is written through the user terminal 100, the abnormality note part 320 may display and store a time in a messenger form. In the platform of the present invention, a user is supposed to write a record every day or periodically, but there are cases where the user cannot write a record by stages, for example, an emergency case or urgent case where it is necessary to immediately write a record. Accordingly, when the user selects an abnormality note item of "immediately note anything strange," a messenger-type window may be output, providing an interface for recording a conversation in a messenger form. The recorded data may be output in an administrator mode of the veterinary hospital terminal 400 shown in FIGS. 4U to 4X.

When an SRR is measured through the user terminal 100, the SRR part 330 may store time-series changes of the SRR in a log and visualize the time-series changes of the SRR as a graph. Here, the SRR is obtained by counting breaths of the sleeping companion animal per minute, and one count is made every cycle that the abdomen or chest rises and falls with inhalation and exhalation. In the case of a companion animal that has a heart disease and takes a heart medicine, it is very important to measure the SRR. When the SRR is in a preset stable range, for example, 18 to 22 per minute, there is a very low possibility of difficulty breathing such as pulmonary edema, and otherwise, there is a possibility of difficulty breathing or syncope. Therefore, an SRR is called home chest radiation, and its importance is very high. For example, when the SRR continuously increases up to X % or more, this may indicate that there has been a change in the overall body condition of the companion animal, and when the SRR decreases by 2% or more, it is necessary to check whether the heart medicine, such as a diuretic, is not being excessively used.

Accordingly, when the user clicks the item "measure the SRR please" in the menu of FIG. 3A, the SRR part 330 may output a timer for counting down to 60 seconds on a screen of the user terminal 100 and aid the user in concentrating on counting the numbers. When it is difficult for the user to count the numbers and the user clicks the item "measure the SRR please," the SRR part 330 may cause the user terminal 100 to display a video capturing screen (no sound), capture a video for one minute, and then immediately upload the video. Here, inhalation and exhalation may be automatically counted using a deep-learning-based AI algorithm because rises and falls of the abdomen or chest can be analyzed through object recognition. Alternatively, in the case of a smartphone with a depth camera or two or more cameras, the SRR may be calculated by measuring changes in the depth of the chest or abdomen, or the depth may be measured using a technique employing a red green blue-depth (RGB-D) camera or multiple cameras as a depth camera. Otherwise, rises and falls of the chest may be measured using a skeleton algorithm to find one cycle, and the number of breaths may be automatically recorded for 60 seconds. All the user has to do is press a capture button and image the companion animal for one minute.

When syncope or a seizure is recorded, the syncope-seizure distinction part 340 may map questions and a checklist regarding syncope and seizures to the record and answers and store the record and answers mapped to the questions and checklist. The user terminal 100 may answer at least one question and the checklist for recording an abnormality note, an SRR, a status, and syncope and seizures. The veterinary hospital terminal 400 may output records written through the user terminal 100 in real time. As shown in FIGS. 3W to 4R, the at least one question and the checklist for recording syncope and seizures make it possible to identify syncope or a seizure through 20 stages and record what kind of symptom has occurred in detail. For example, as shown in FIGS. 3W to 4R, questions and a checklist may be about times, a frequency, and durations of syncope or seizures, a situation before the symptom, presence or absence of consciousness at onset, presence or absence of an abnormal symptom before the symptom, a recovery time after the symptom, whether the situation is suspected to be syncope or a seizure, whether there is stiffness or relaxation, the color of the gums, whether the pulse rate is abnormal, whether the companion animal is bending in a bow shape, whether there has been an aura symptom, whether defecation or urination has occurred, whether the companion animal is making a sound, whether the companion animal is drooling, whether the companion animal is suffering from hyperventilation or apnea, and presence or absence of eye movements, but the questions and checklist may vary depending on embodiments. Also, the questions and checklist are not limited thereto and do not exclude anything not listed above.

When a veterinary hospital is selected for treatment through the user terminal 100, the first medical examination request part 350 may provide a preceding medical questionnaire for first medical examination to the user terminal 100 and transmit medical questionnaire response data input through the user terminal 100 to the veterinary hospital terminal 400 of the veterinary hospital selected through the user terminal 100.

When retreatment at a veterinary hospital where the companion animal has been treated is requested through the user terminal 100, the retreatment request part 360 may transmit a preceding medical questionnaire for retreatment to the user terminal 100 and transmit medical questionnaire response data input through the user terminal 100 to the veterinary hospital terminal 400 of the veterinary hospital selected through the user terminal 100.

The medical record part 370 may transmit an electronic medical record (EMR) made through the veterinary hospital terminal 400 to the user terminal 100 and allow a diagnosed disease code and a prescribed prescription drug list from the veterinary hospital terminal 400 to be checked through the user terminal 100. Various vaccine certificates are necessary for the user to go abroad with the companion animal, and it is necessary to embed an animal registration chip in the companion animal so that the user may come back with the companion animal. In the event of a transfer or regional assignment, it may be necessary to change veterinary hospitals. Here, when the record is kept at the veterinary hospital, the companion animal with the heart disease is examined or identified again from the beginning because there is no record at the new veterinary hospital. In this case, the companion animal's stress index may rise rapidly, which may cause very poor prognosis for the companion animal with the heart disease. Even in the case of people, EMRs were not shared among hospitals, which was problematic. Currently, the National Health Insurance Service, the Health Insurance Review and Assessment Service, the National Tax Service, and the like are providing EMRs due to the Three Data Acts related to MyData. Since the acts do not apply to companion animals, the user terminal 100 is allowed to manage the diagnosed disease code and prescribed prescription drug list from the veterinary hospital terminal 400 that are input to the platform of the present invention, and an edge cloud platform or distributed computing cloud platform may be used for this purpose.

When at least one wearable device interoperates with the user terminal 100, the automatic record part 380 may fill in whether there is syncope or a seizure, whether there is a sound during syncope or a seizure, a body temperature, a pulse rate, and a respiratory rate, which are collected from an acceleration sensor, a microphone, a pulse rate sensor, a temperature sensor, and a respiratory rate sensor of the at least one wearable device, with the answers to the at least one question and checklist. The wearable device may be woken up by the acceleration sensor due to acceleration that is caused within a preset range when the companion animal collapses from syncope or a seizure and record and transmit whether there is syncope or a seizure, whether there is a sound during syncope or a seizure, a body temperature, a pulse rate, and a respiratory rate to the user terminal 100. However, in the case of a companion animal with a heart disease, even a little stress or excitement may cause difficulty breathing and even syncope in severe cases. Accordingly, it is necessary to equip the companion animal with the wearable device with as little stress as possible. To this end, smart clothes may be used.

For example, a single-walled carbon nano tube (SWCNT) coating material may be processed into various forms and implemented as a fabric sensor to measure motions, or a pulse rate, a respiratory rate, and also an electromyogram (EMG) may be sensed through Medical Sensor Systems of the Fraunhofer Institute or sensors built into the entire clothing of Athos, which is an American smart sports clothing brand, and a device called Athos Core. However, unlike humans, companion animals' skin is covered with fur. Accordingly, accuracy can be increased by placing multiple sensors in parts which show highest accuracy due to little or no fur, for example, the armpits between the arms and chest. To record a respiratory rate, inductive plethysmography, strain gauge plethysmography, capacitive plethysmography, piezoelectric plethysmography, or the like may be used. Among them, strain gauge plethysmography may employ a strain gauge sensor to measure a respiratory rate. The strain gauge sensor is a sensor of which a resistance varies depending on applied force. A gauge converts force, pressure, tension, weight, and the like into changes in electrical resistance, and then the resistance is measured. When external force is applied to a stationary object, stress and strain appear as a result. In this case, the stress is defined as internal resistance of the object, and the strain is defined as displacement and deformation that occur.

Inductive plethysmography is a respiration measurement method for measuring changes in inductance according to volume changes that occur during breathing by equipping a companion animal with sensors on the chest and abdomen. The sensor is configured in a belt shape with zigzag-shaped conducting wires. An inductive fabric sensor employing inductive plethysmography may be used, and heart activity and respiration may be measured by embroidering silver thread on the fabric. As described above, the strain gauge plethysmography is a respiration measurement method for measuring resistance changes through extension or compression of a sensor according to volume changes that occur during breathing by equipping a companion animal with the belt-type sensor on the chest or abdomen. A breathing period, a breathing signal, and a breathing pattern may be evaluated through analysis of measured data. When strain gauge plethysmography is applied, respiration may be measured using a strain gauge-type fabric sensor coated with a transparent conductive oxide and multi-wall carbon nano tubes (MWCNTs). Also, unlike an existing method of measuring a resistance change value according to a change in the length of the respiration sensor, a resistance value may be measured through a change in the contact surface area of a fabric-based sensor.

Capacitive plethysmography is a respiration measurement method for measuring changes in capacitance according to volume changes that occur during breathing by equipping a companion animal with a belt-type sensor made of conductive fibers and non-conductive fibers on the chest or abdomen. For example, a capacitive textile pressure sensor (TCPS) obtained by combining two types of conductive fibers and three types of non-conductive fibers may be used. Piezoelectric plethysmography is a method of measuring an electrical signal generated between two electrodes when a polymer material is pulled due to volume changes during breathing after a companion animal is equipped with a belt-type sensor made of the piezoelectric polymer material on the chest. A sensor which may measure respiration signals using a polyvinylidene fluoride (PVDF) film, which is a piezoelectric polymer material, may be used. To calculate a respiratory rate from chest or abdominal expansion and contraction using plethysmography, a transducer may be used, and the transducer may be configured on the basis of a force-sensing resistor (FSR) for measuring changes in chest or abdominal circumference.

When medicine is prescribed through the veterinary hospital terminal 400, the administration notification part 390 may cause the user terminal 100 to output a medication time of each prescription drug as an alarm at medication intervals of the prescription drug input through the veterinary hospital terminal 400. According to prescribed drugs, there are various medication intervals such as twelve hours, six hours, four hours, and the like. Since it is not easy for the user to remember all the medication intervals, the user terminal 100 may be set to automatically trigger an alarm at intervals of a prescribed drug.

The collaborative treatment part 391 may cause a single or plurality of veterinary hospital terminals 400 to output records and answers input through the user terminal 100 according to a setting, cause the single or plurality of veterinary hospital terminals 400 to share diagnostic and medical records, and allow sharing of diagnostic, remedial, and treatment data uploaded by the single or plurality of veterinary hospital terminals 400. Here, the veterinary hospital terminal 400 may be singular or plural in number depending on a setting. Employed veterinarians often give up expressing their opinions due to hierarchical order when their opinions conflict with those of their superiors who have personnel authority. Accordingly, a method of uploading a diagnosis code anonymously and sharing opinions about the uploaded diagnosis code may be additionally used. Alternatively, the collaborative treatment part 391 may be set so that the same medical record and chart are viewed, diagnosed, and shared among multiple hospitals rather than within one hospital.

The community part 393 may create at least one community and allow user terminals 100 to share information with each other. Users who register companion animals of like kinds, with like diseases, or with like ages may be allowed to create a community and share information.

In addition, according to an exemplary embodiment of the present invention, companion animal information may be accumulated and linked between hospitals on the basis of a platform such as an electronic health record (EHR). Here, the EHR is a system for sharing medical data in hospital units according to an existing EMR method. The EHR has an advantage that, when any companion animal comes, each medical institution can provide a medical service by combining all medical data of the companion animal. However, currently, patient data is dispersed across hospitals, and it is difficult to integrate the patient data. A method that goes one stage further is a personal health record (PHR). Through a PHR system, medical data of companion animals can be shared among guardians as well as hospitals. At this stage, when a companion animal and its guardian visit a veterinary hospital, medical data is submitted to the hospital or checked on the platform, and a veterinarian can determine the companion animal's condition quickly and efficiently.

Further, the platform according to an exemplary embodiment of the present invention creates big data of accumulated EHRs, generates symptom-disease datasets, and then learns and verifies the symptom-disease datasets through at least one AI algorithm. After that, when a record of a new companion animal which is similar to a pattern accumulated, learned, and verified in advance is input, the platform may predict and detect a disease in an early stage. When the at least one AI algorithm derives a disease from a question of data, whether at least one symptom of the disease corresponds to a symptom in the biological data can be determined on the basis of correlation, and the reliability of a disease prediction can be determined.

Medical diagnosis based on physiological information (biological data) is the oldest method and the most common diagnostic method to date. In the past, physiological information was sampled and used for a relatively short period of time, whereas, due to the development of big data technology and AI technology, physiological information collected over a relatively long period of time is being used for diagnosing diseases with a new perspective and accuracy different from the past. The temporal data collected over a long period of time is called medical time-series data. For example, the characteristics of pulse rates in time-series data are closely related to the prevalence of various diseases. Alternatively, the problem may be identified by collecting time-series data on physiological information and comparing physiological characteristics of each animal patient when the animal is healthy and when the animal has a disease. Accordingly, a model may be generalized by analyzing time-series data labeled with diseases of animal patients through a recurrent neural network (RNN) which is effective in time-series data analysis. Recorded data may be analyzed to predict a disease and used for determining how high the prediction reliability of a disease, that is, the power of predicting a disease, or the accuracy of a diagnosis is.

Since data collected according to an exemplary embodiment of the present invention is time-series data, a time-series data labeling method may be further employed to use deep learning, such as an RNN or long short-term memory (LSTM), specialized in analyzing time-series data. For example, after the data is modeled with a deep learning approach instead of a probabilistic machine learning anomaly detection algorithm, datasets may be generated using deep learning to detect an abnormal resting pulse rate from test data related to a user's baseline and diagnose a heart disease or the like including a pulse rate as a symptom or may be provided when biological data, such as a pulse rate, is necessary for a diagnosable disease. Here, types of diseases are not limited to heart diseases.

An operation process according to the foregoing configuration of the medical record service providing server of FIG. 2 will be described in detail below with examples of FIGS. 3 and 4. However, an exemplary embodiment is any one of various embodiments of the present invention, and the present invention is not limited thereto.

Due to the number of drawings, all screens of the platform of the present invention are not shown in FIGS. 3 and 4, and the following screens are not all screens of the platform of the present invention. Also, an order, an arrangement, a layout, a frame, or the like may vary depending on each embodiment.

When the first item "Basic information of my pet" is clicked in the menu of FIG. 3A, basic information is checked in detail through FIGS. 3B to 3F. Since each user is a layperson rather than an expert, answers to each question may be prepared in advance, and an answer can be input simply by selecting one of the answers. FIG. 3G corresponds to the second item "immediately note anything strange" in the menu of FIG. 3A. As shown in FIG. 3H, an urgent or emergency situation may be immediately noted and then input to a status record or shown to a veterinarian in charge. FIG. 3I corresponds to the fifth item "notes immediately before visiting a veterinary hospital" in the menu of FIG. 3A. As shown in FIGS. 3J to 3P, data that a veterinary hospital is required to know may be uploaded in advance before the companion animal arrives at the veterinary hospital. Since companion animals are not able to speak, questioning and answering between users and veterinarians is important. Not only in emergency and urgent situations but also in non-emergency situations, when questions and answers are provided in advance, a waiting time can be shortened, and treatment efficiency can be increased. When the user and companion animal visit the veterinary hospital due to an abnormality, answers may be provided as shown in FIGS. 3Q to 3S.

Figure 3U:
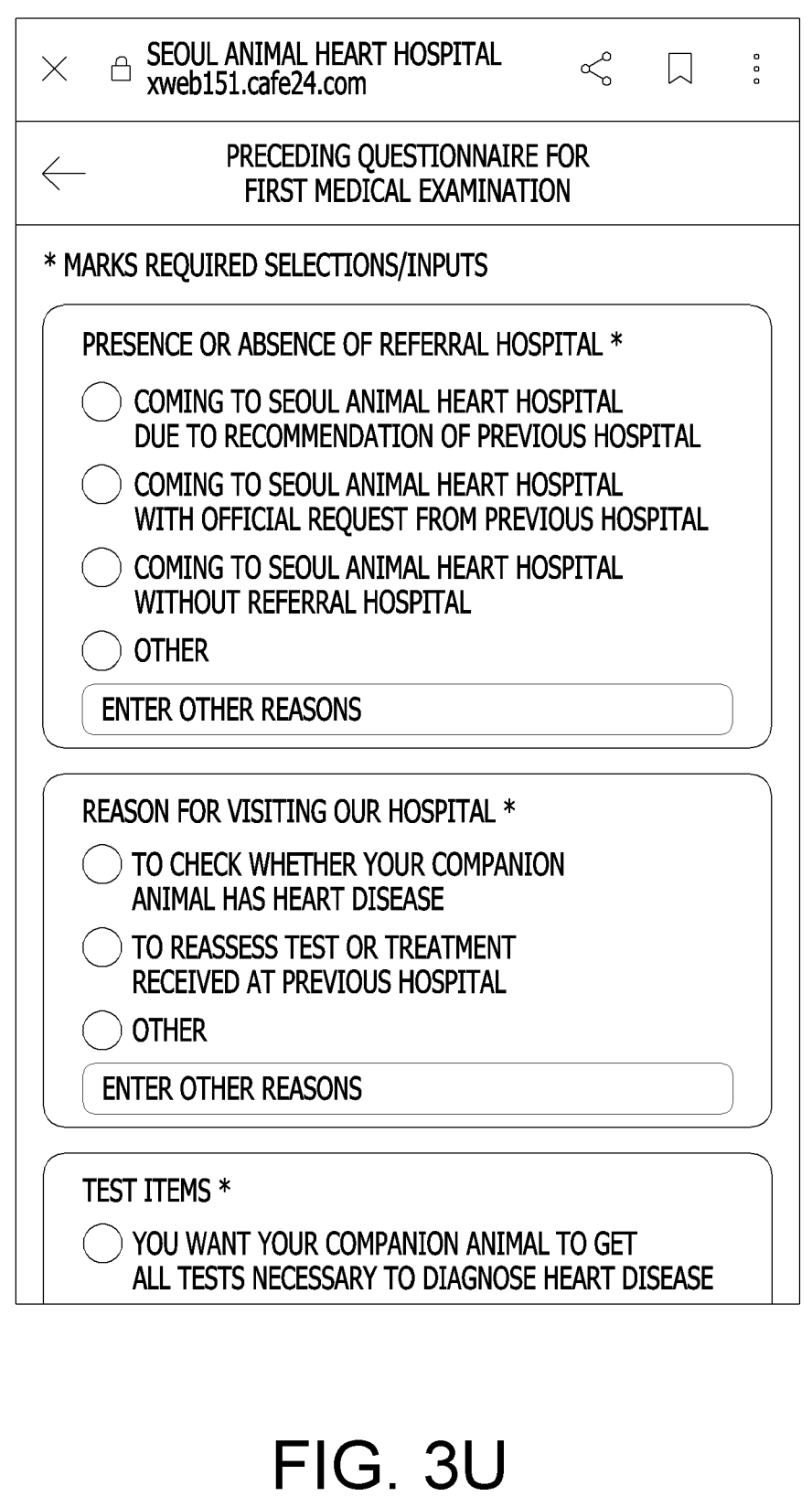
Figure 3V:
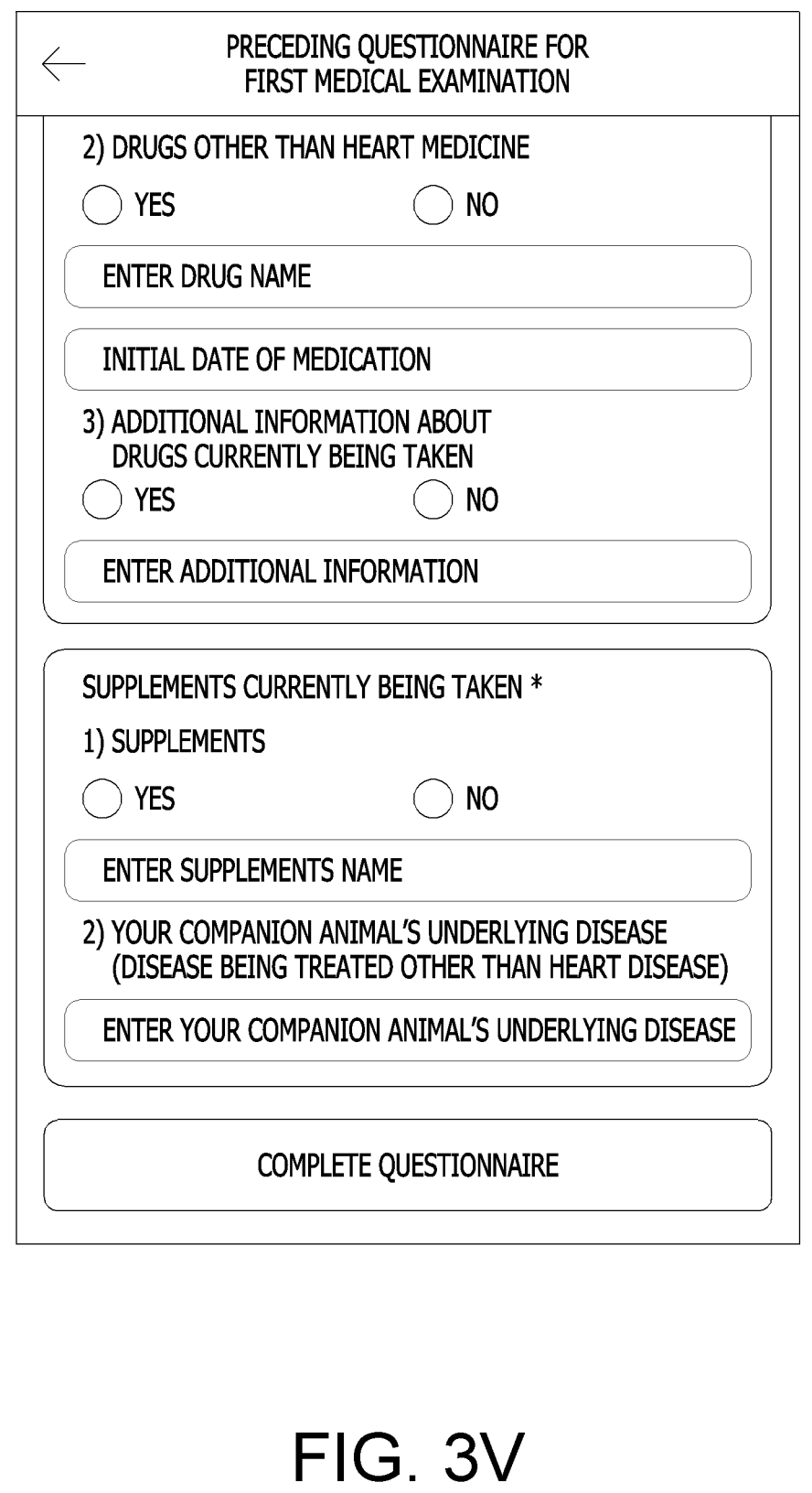
Figure 3Y:
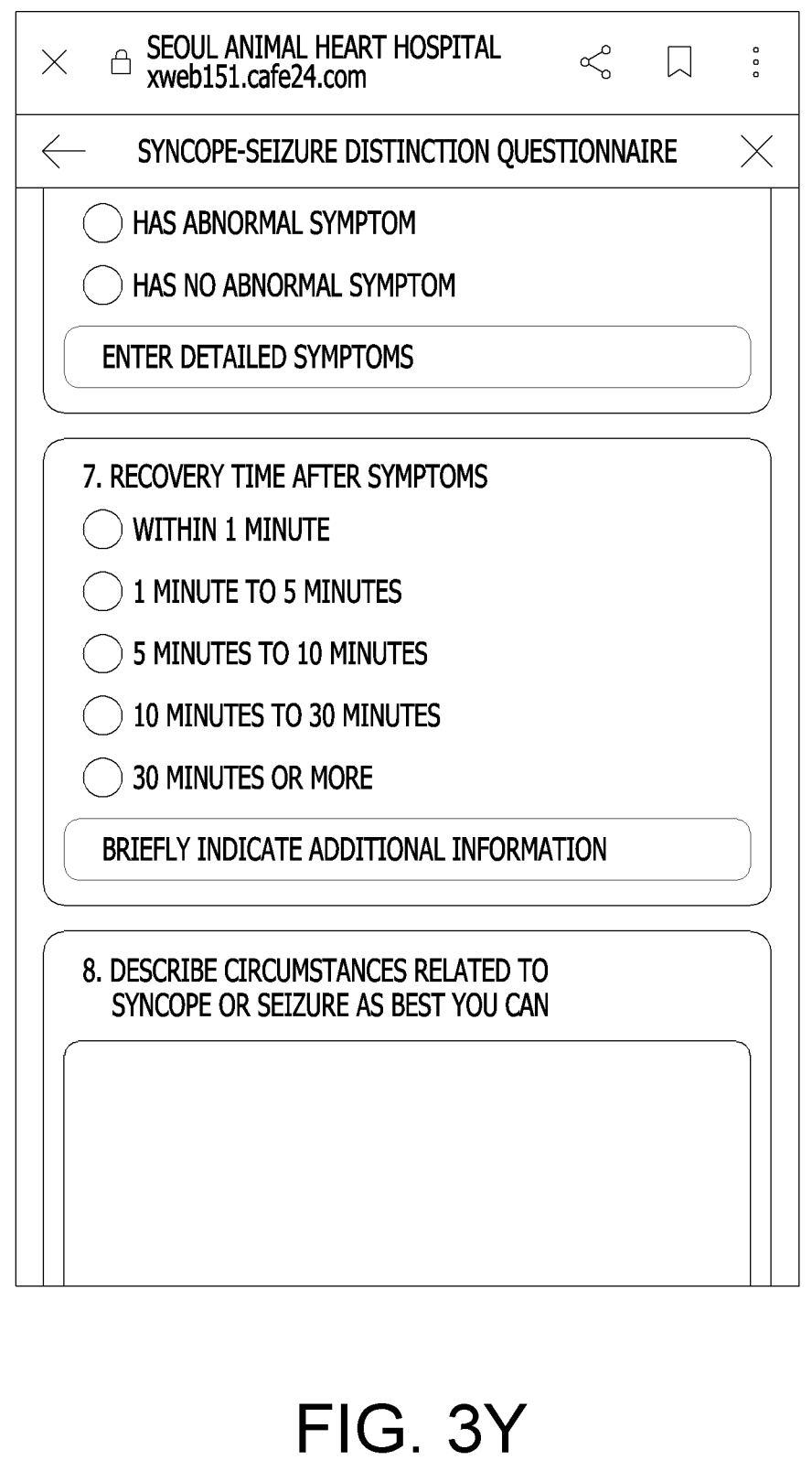
Figure 3Z:
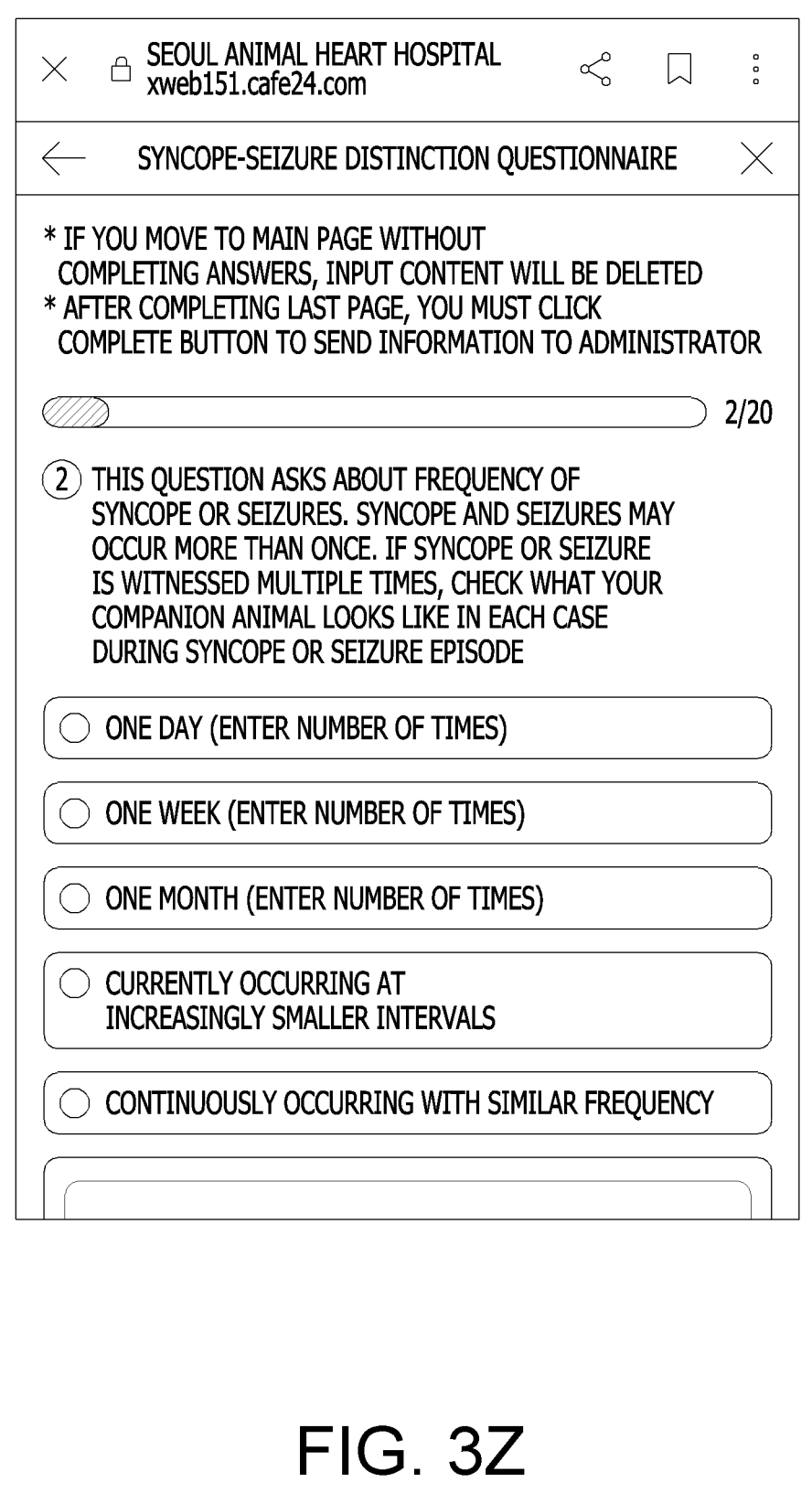
Figure 4N:
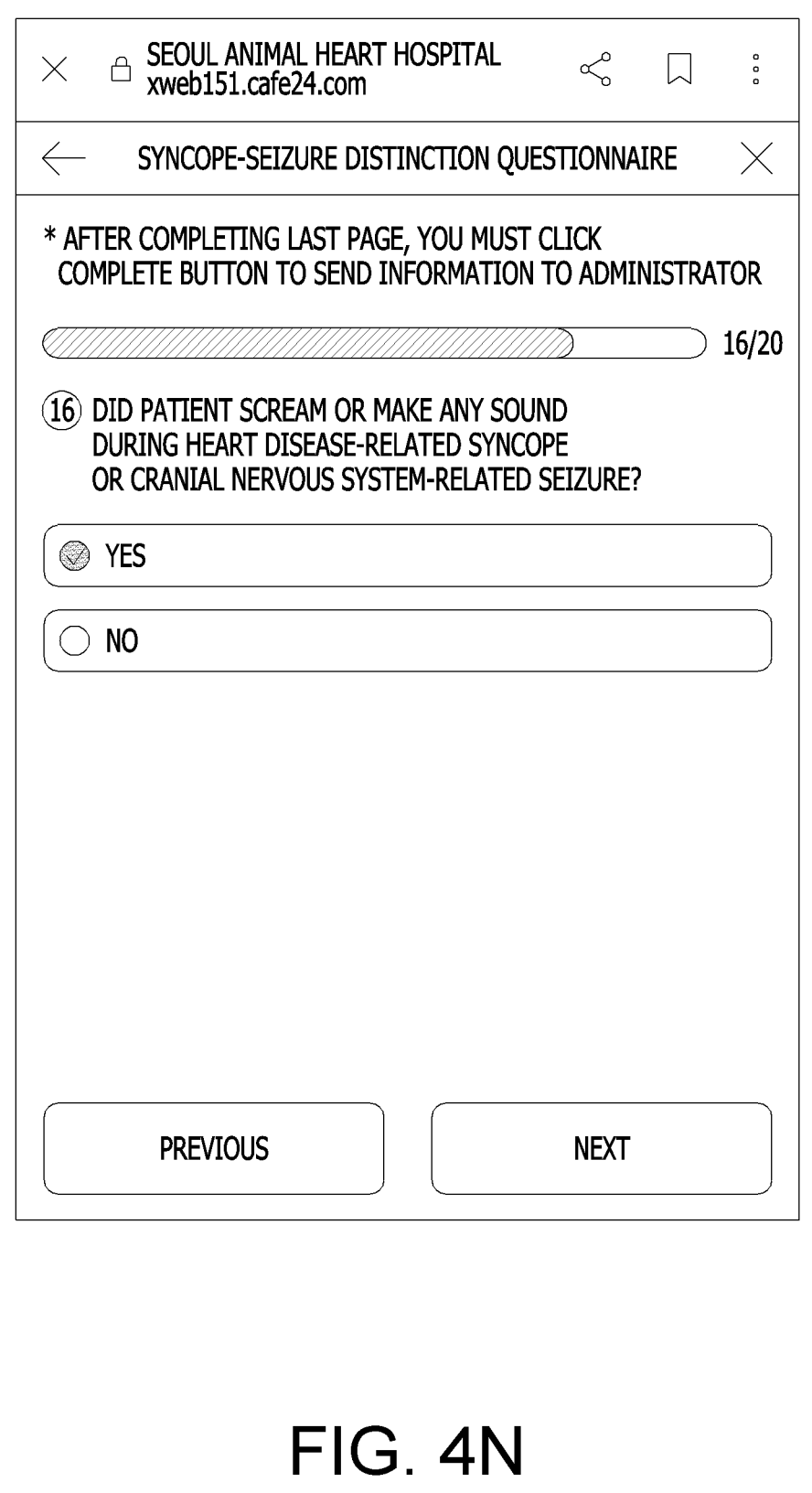
Figure 4O:
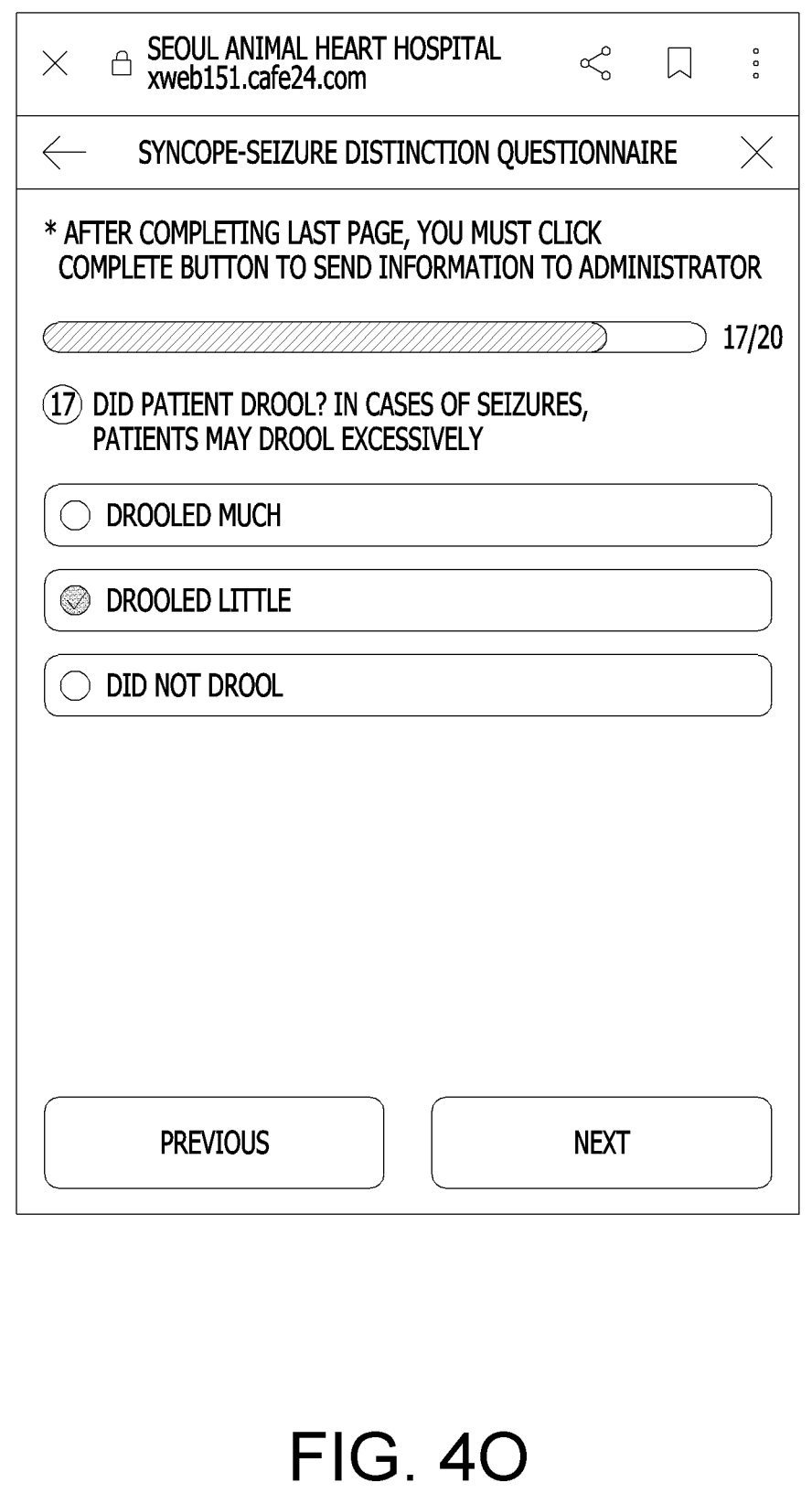
Figure 4S:
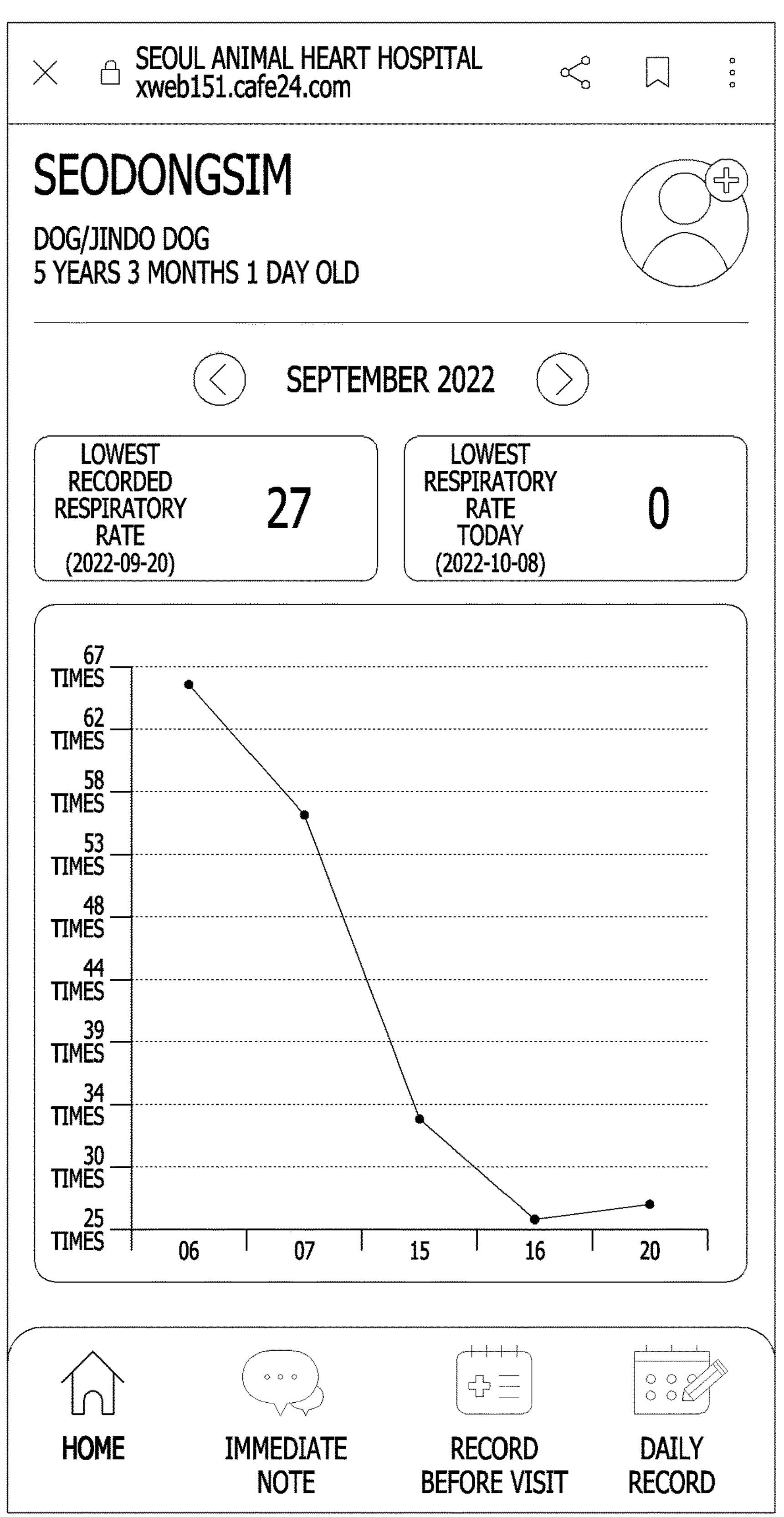

FIG. 3T corresponds to the sixth item "preceding questionnaire for first medical examination" in the menu of FIG. 3A. An interface for answering may be provided as shown in FIGS. 3U and 3V. As described above, FIGS. 3W to 4R correspond to the seventh item "distinction between syncope and seizures." FIGS. 4S and 4T correspond to the third item "measure your companion animal's SRR" in the menu of FIG. 3A. FIG. 4S is a screen that visualizes recording results as a graph, and FIG. 4T is a screen for recording. As shown in FIG. 4T, a video guide link is inserted in connection with how to measure an SRR, and an item is provided to upload a video when it is difficult to insert the link.

Although the fourth item "record your companion animal's status every day" in the menu of FIG. 3A is not illustrated in the drawings, photos are uploaded regarding whether the companion animal eats its food well, whether the companion animal is a picky eater, how the companion animal's compliance with forced feeding is, whether the companion animal is losing or gaining weight or staying the same, whether the companion animal drinks water well, whether the companion animal has bowel movements and how many bowel movements the companion animal has, and whether the average condition of the companion animal's bowel movements is normal. Also, whether the stool is moist and well-shaped, whether the stool is soft and barely maintains its shape, whether the stool is very soft and shapeless, that is, in the form of a spread on the floor, whether there is much mucus in the stool, whether there is blood in the stool, and the like may be checked. In addition, photos may be uploaded regarding how the companion animal's urination is and whether the companion animal has any abnormality during urination. As shown in FIGS. 3N to 3Q, how much the companion animal weighs, whether the companion animal has a cough, and the like may also be checked. FIGS. 4U to 4X may be screens of the veterinary hospital terminal 400, and data transmitted from the user terminal 100 may be output in real time. As shown in FIG. 4Y, in an administrator mode, a record of the user terminal 100 may be downloaded as an Excel file, and as shown in FIG. 4Z, basic information, a first medical examination record, daily records, immediate notes, records before visiting a veterinary hospital, and the like may be separated into tabs and provided in an Excel format to facilitate recognition. The present applicant is preparing an application on this (Dr. Record).

Undescribed details of the method of providing a medical record service for diagnosing a companion animal with a heart disease or internal disease illustrated in FIGS. 2 to 4 are the same as the description of the system for diagnosing a companion animal with a heart disease or internal disease illustrated in FIG. 1 or easily derivable therefrom, and thus the description will be omitted.

Figure 5:
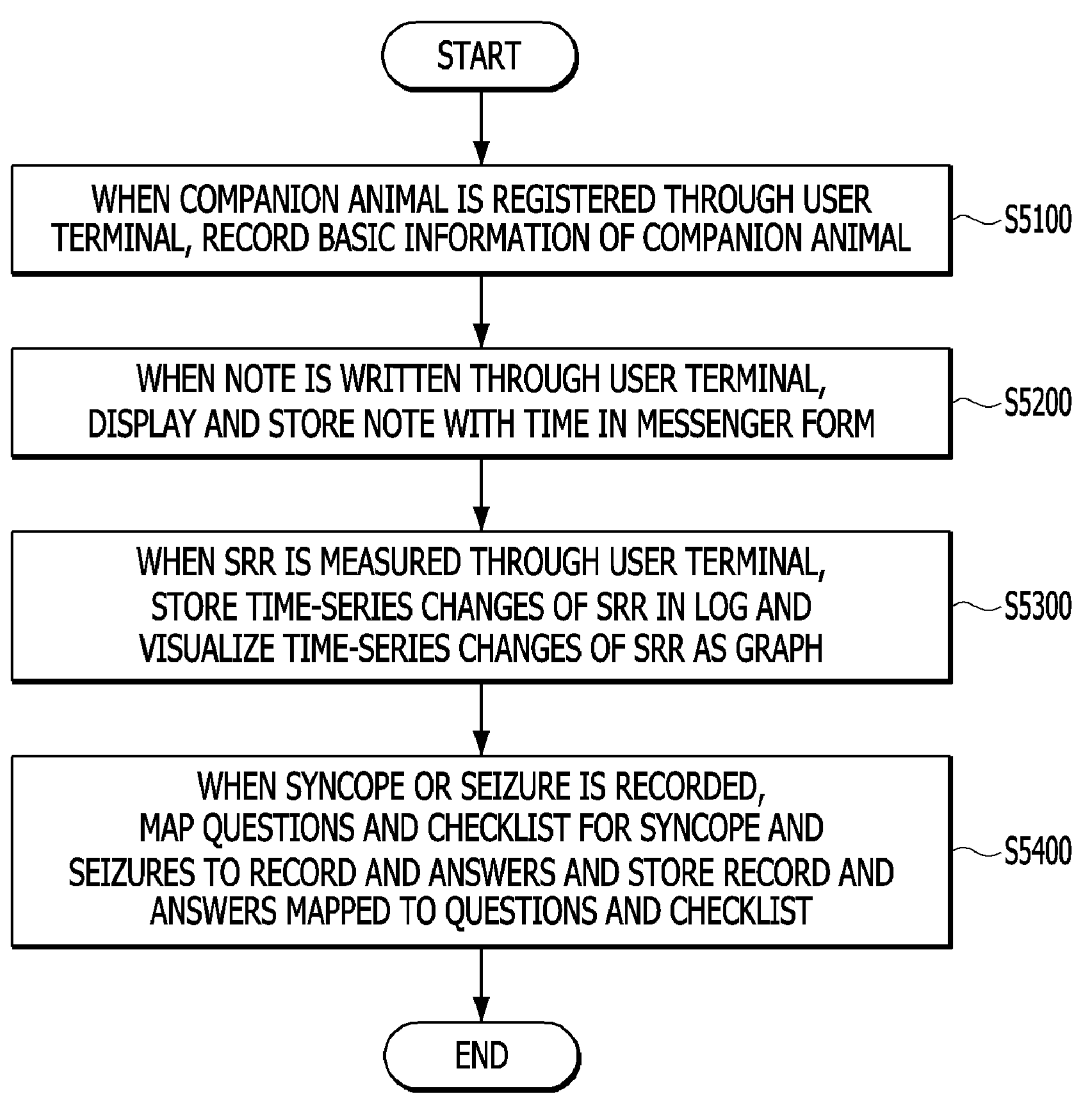
FIG. 5 is a flowchart illustrating a method of providing a medical record service for diagnosing a companion animal with a heart disease or internal disease according to an exemplary embodiment of the present invention.

FIG. 5 is a diagram illustrating a process in which data is transmitted and received between components included in the system for providing a medical record service for diagnosing a companion animal with a heart disease or internal disease according to an exemplary embodiment of the present invention. An example of a process in which data is transmitted and received between components will be described below through FIG. 5. However, the present invention is not limited to the embodiment, and it is apparent to those of ordinary skill in the art that the process in which data is transmitted and received illustrated in FIG. 5 may vary depending on the various embodiments described above.

Referring to FIG. 5, when a user terminal registers a companion animal, a medical record service providing server records basic information of the companion animal (S5100), and when a note is written through the user terminal, the medical record service providing server displays and stores the note with the time in a messenger form (S5200).

Also, when an SRR is measured through the user terminal, the medical record service providing server stores time-series changes of the SRR in a log and visualizes the time-series changes as a graph (S5300). When syncope or a seizure is recorded, the medical record service providing server maps questions and a checklist for syncope and seizures to a record and answers and stores the record and answers mapped to the questions and checklist (S5400).

The sequence of the foregoing operations S5100 to S5400 is only an example, and the present invention is not limited thereto. In other words, the sequence of the foregoing operations S5100 to S5400 may be changed, and some of the operations may be simultaneously performed or omitted.

Undescribed details of the method of providing a medical record service for diagnosing a companion animal with a heart disease or internal disease illustrated in FIG. 5 are the same as the description of the system and method for diagnosing a companion animal with a heart disease or internal disease illustrated in FIGS. 1 to 4 or easily derivable therefrom, and thus the description will be omitted.

The method of providing a medical record service for diagnosing a companion animal with a heart disease or internal disease according to an exemplary embodiment illustrated in FIG. 5 may be implemented in the form of a recording medium including computer-executable instructions such as an application or program module executed by a computer. The computer-readable medium may be any available medium that is accessed by a computer and may be any one of volatile and non-volatile media and detachable and non-detachable media. The computer-readable medium may any computer storage medium. The computer storage media include volatile and non-volatile media and detachable and non-detachable media that are implemented using any method or technology for storing information such as data structures, program modules, or other data.

The above-described method of providing a medical record service for diagnosing a companion animal with a heart disease or internal disease according to an exemplary embodiment of the present invention may be executed by an application (which may include a program included in a platform, an operating system (OS), or the like basically installed on a terminal) basically installed on a terminal or may be executed by an application (i.e., a program) installed on a master terminal personally by a user through an application providing server such as an application store server, a web server related to the application or a corresponding service. In this regard, the above-described method of providing a medical record service for diagnosing a companion animal with a heart disease or internal disease according to an exemplary embodiment of the present invention may be implemented as an application (i.e., a program) basically installed or personally installed by a user on a terminal and recorded on a computer-readable recording medium such as a terminal or the like.

The above description of the present invention is illustrative, and those skilled in the technical field to which the present invention pertains should understand that the present invention can be easily modified into other specific forms without changing the technical spirit or essential features of the present invention. Therefore, the exemplary embodiments described above are to be understood as illustrative and not limiting in all aspects. For example, each component described as a single part may be implemented in a distributed manner, and components described as being distributed may also be implemented in a combined form.

The scope of the present invention is represented by the following claims rather than the detailed description above, and all modifications and alterations derived from meanings and the scope of the claims and equivalents thereto are construed as falling within the scope of the present invention.

INDUSTRIAL APPLICABILITY

A platform according to an exemplary embodiment of the present invention can not only be used in preventive health care, such as basic health care and vaccines, and special disease management, such as for a heart disease, but can also be expanded to all disease areas such as a liver disease, a skin disease, or the like.

What is claimed is:

1. A system for providing a medical record service for diagnosing a companion animal with a heart disease or internal disease, the system comprising:

a camera;

a user terminal configured to register a companion animal and then answer at least one question and a checklist for noting an abnormality, measuring a sleeping respiratory rate (SRR), recording a status, and recording syncope and seizures, wherein the user terminal includes a display displaying a user interface having at least one icon;

a wearable device worn on the companion animal and automatically enabled to detect and transmit a sound, a body temperature, a pulse rate, or a respiratory rate to the user terminal in response to an acceleration change detected by an accelerator included in the wearable device, wherein the wearable device further includes a microphone detecting the sound made by the companion animal, a temperature sensor detecting the body temperature of the companion animal, a pulse rate sensor detecting the pulse rate of the companion animal, and a respiratory rate sensor detecting the respiratory rate of the companion animal, a plurality of veterinary hospital terminals configured to output records written through the user terminal; and a medical record service providing server including a basic information part configured to allow the user terminal to record basic information of the companion animal when the user terminal registers the companion animal, an abnormality note part configured to display and store the abnormality note and a time in a messenger form when the abnormality note is written through the user terminal, an SRR part configured to store time-series changes of the SRR in a log and visualize the time-series changes of the SRR as a graph when the user terminal measures the SRR, an automatic record part that records the sound, the body temperature, the pulse rate, and the respiratory rate of the companion animal which are detected and received from the user terminal in response to a detection of the acceleration change, and a syncope-seizure distinction part configured to map questions and a checklist for syncope and seizures to a record and answers and store the record and answers mapped to the questions and checklist, wherein, in response to an touch operation being performed on the at least one icon of the user interface being displayed on the display of the user terminal, the camera is enabled to capture a video of the companion animal, and then the SRR part calculates the SRR of the companion animal by analyzing the video captured for a preset period of time to check whether an SRR of a companion animal that has a heart disease and takes a heart medicine continuously increases up to a preset value or more or decreases down to another preset value or less by automatically measuring changes in a depth of a chest or abdomen of the companion animal using a skeleton algorithm to find one cycle through object recognition, and the number of breaths may be automatically recorded for the preset period, wherein the veterinary hospital terminals are further configured to transmit diagnosis and a prescription of prescription drug, wherein the medical record includes the basic information, the abnormality note, the SRR and the record and the answers for the syncope and seizures, and wherein the user terminal is further configured to automatically set and trigger an alarm at a medication time of the prescribed prescription drug based on the prescription of the prescription drug, wherein the veterinary hospital terminals include a first veterinary hospital terminal and a second veterinary hospital terminal disposed at different veterinary hospital with respect to the first veterinary hospital terminal, and the second veterinary hospital terminal is configured to access the medical record service providing server to obtain the medical record transmitted by the first veterinary hospital terminal through the user terminal, so as to quickly and effectively diagnose a condition of the companion animal based on the medical record of the companion animal recorded in the medical record service providing.

2. The system of claim 1, wherein the at least one question and the checklist for recording syncope and seizures include times, a frequency, and durations of syncope or seizures, a situation before a symptom, presence or absence of consciousness at onset, presence or absence of an abnormal symptom before the symptom, a recovery time after the symptom, whether a situation is suspected to be syncope or a seizure, whether there is stiffness or relaxation, a color of gums, whether a pulse rate is abnormal, whether the companion animal is bending in a bow shape, whether there has been an aura symptom, whether defecation or urination has occurred, whether the companion animal is making a sound, whether the companion animal is drooling, whether the companion animal is suffering from hyperventilation or apnea, and presence or absence of eye movements.

3. The system of claim 1, wherein, when the user terminal selects a veterinary hospital and requests treatment, the medical record service providing server provides a questionnaire for first medical examination to the user terminal and transmits questionnaire answer data input through the user terminal to the veterinary hospital terminal of a veterinary hospital selected through the user terminal.

4. The system of claim 3, wherein the medical record service providing server further comprises a retreatment request part configured to, when the user terminal requests retreatment at the veterinary hospital where the companion animal has been treated earlier, transmit a preceding questionnaire for retreatment to the user terminal and transmit the preceding questionnaire for retreatment answered through the user terminal to the veterinary hospital terminal of the veterinary hospital selected through the user terminal.

5. The system of claim 1, wherein the medical record service providing server further comprises a medical record part configured to transmit an electronic medical record (EMR) written through the veterinary hospital terminal to the user terminal and allow a diagnosed disease code and a prescribed prescription drug list from the veterinary hospital terminal to be checked through the user terminal.

6. The system of claim 1, wherein the medical record service providing server further comprises an automatic record part configured to, when the wearable device interoperates with the user terminal, fill in whether there is syncope or a seizure, whether there is a sound during syncope or a seizure, a body temperature, a pulse rate, and a respiratory rate, which are collected from an acceleration sensor, a microphone, a pulse rate sensor, a temperature sensor, and a respiratory rate sensor of the wearable device, with the answers to the at least one question and the checklist.

7. The system of claim 6, wherein the wearable device is woken up by the acceleration sensor due to acceleration that is caused within a preset range when the companion animal collapses from syncope or a seizure and records and transmits whether there is syncope or a seizure, whether there is a sound during syncope or a seizure, the body temperature, the pulse rate, and the respiratory rate to the user terminal.

8. The system of claim 1, wherein the medical record service providing server further comprises a collaborative treatment part configured to output the record and answers input through the user terminal to one or more of the plurality of veterinary hospital terminals and share diagnostic, remedial, and treatment data uploaded by the one or more of the plurality of veterinary hospital terminals among the plurality of veterinary hospital terminals.

9. The system of claim 1, wherein the medical record service providing server further comprises a community part configured to create at least one community and allow user terminals to share information with each other.

* * * * *